United States Patent
Dotson et al.

(10) Patent No.: US 9,546,182 B2
(45) Date of Patent: Jan. 17, 2017

(54) TRICYCLIC PI3K INHIBITOR COMPOUNDS AND METHODS OF USE

(71) Applicant: Genentech, Inc., South San Francisco, CA (US)

(72) Inventors: Jennafer Dotson, Belmont, CA (US); Robert Andrew Heald, Harlow (GB); Timothy Heffron, Burlingame, CA (US); Graham Elgin Jones, Harlow (GB); Sussie Lerche Krintel, Harlow (GB); Neville James McLean, Harlow (GB); Chudi Ndubaku, San Francisco, CA (US); Alan G. Olivero, Half Moon Bay, CA (US); Laurent Salphati, San Francisco, CA (US); Lan Wang, Foster City, CA (US); BinQuing Wei, Belmont, CA (US)

(73) Assignee: Genentech, Inc., South San Francisco (*) Notice: Subject to any disclaimer, the term of this patent is extended or adjusted under 35 U.S.C. 154(b) by 0 days.

(21) Appl. No.: 14/524,204

(22) Filed: Oct. 27, 2014

(65) Prior Publication Data

US 2015/0079081 A1 Mar. 19, 2015

Related U.S. Application Data

(62) Division of application No. 13/326,524, filed on Dec. 15, 2011, now Pat. No. 8,883,799.

(60) Provisional application No. 61/423,694, filed on Dec. 16, 2010.

(51) Int. Cl.

| | | |
|---|---|---|
| C07D 471/14 | (2006.01) | |
| C07D 471/22 | (2006.01) | |
| C07D 487/14 | (2006.01) | |
| C07D 498/14 | (2006.01) | |
| C07D 491/14 | (2006.01) | |
| C07D 495/14 | (2006.01) | |
| A61K 31/5377 | (2006.01) | |
| A61K 31/5383 | (2006.01) | |
| A61K 31/5386 | (2006.01) | |
| A61K 39/395 | (2006.01) | |
| C07D 491/147 | (2006.01) | |
| C07D 498/20 | (2006.01) | |
| A61K 39/00 | (2006.01) | |

(52) U.S. Cl.
CPC ......... *C07D 498/14* (2013.01); *A61K 31/5377* (2013.01); *A61K 31/5383* (2013.01); *A61K 31/5386* (2013.01); *A61K 39/3955* (2013.01); *C07D 487/14* (2013.01); *C07D 491/14* (2013.01); *C07D 491/147* (2013.01); *C07D 495/14* (2013.01); *C07D 498/20* (2013.01); *A61K 2039/505* (2013.01); *C07D 471/14* (2013.01); *C07D 471/22* (2013.01)

(58) Field of Classification Search
CPC ... C07D 471/04; C07D 471/22; C07D 487/04; C07D 413/00; C07D 265/00; C07D 498/00
See application file for complete search history.

(56) References Cited

U.S. PATENT DOCUMENTS

| | | |
|---|---|---|
| 3,016,378 A | 1/1962 | Roch |
| 4,146,716 A | 3/1979 | Cox et al. |
| 4,704,381 A | 11/1987 | Schaumann et al. |
| 4,714,764 A | 12/1987 | Sato et al. |
| 4,728,644 A | 3/1988 | Yuki et al. |
| 4,740,230 A | 4/1988 | Takematsu et al. |
| 4,818,761 A | 4/1989 | Sato et al. |
| 4,932,998 A | 6/1990 | Takematsu et al. |
| 5,332,744 A | 7/1994 | Chakravarty et al. |

(Continued)

FOREIGN PATENT DOCUMENTS

| | | |
|---|---|---|
| EP | 1277738 A1 | 1/2003 |
| GB | 2431156 A | 4/2007 |

(Continued)

OTHER PUBLICATIONS

Andricopulo et al., "Structure-activity relationships for a collection of structurally diverse inhibitors of purine nucleoside" Chem Pharm Bull 49(1):10-7 (2001).
Bourguignon et al., "9-Benzyladenines: Potent and selective cAMP phosphodiesterase inhibitors" J Med Chem. 40(12):1768-70 (1997).
Breshears et al., "Purines. VIII. Aminolysis of certain chlorosubstituted purines" Jour. Amer. Chem. Soc. 81:3789-92 (Jul. 20, 1959).
Cerna et al., "Direct C—H arylation of purines: development of methodology and its use in regioselective synthesis of 2,6,8-trisubstituted purines" Org Lett 8(23):5389-92 (2006).
Che et al., "Synthesis of novel pyrimidine fused 8-membered heterocycles via iminium ion cyclization reactions" J Org Chem. 73(3):1147-9 (2008).

(Continued)

*Primary Examiner* — Samira Jean-Louis
(74) *Attorney, Agent, or Firm* — Louis C. Cullman; Brian J. Novak; Nigel Robert Lokan

(57) ABSTRACT

Tricyclic PI3k inhibitor compounds of Formula I with anti-cancer activity, anti-inflammatory activity, or immuno-regulatory properties, and more specifically with PI3 kinase modulating or inhibitory activity are described. Methods are described for using the tricyclic PI3K inhibitor compounds of Formula I for in vitro, in situ, and in vivo diagnosis or treatment of mammalian cells, organisms, or associated pathological conditions.

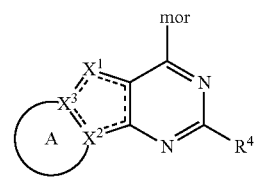

Formula I compounds include stereoisomers, geometric isomers, tautomers, and pharmaceutically acceptable salts thereof. The dashed lines indicate an optional double bond, and at least one dashed line is a double bond. The substituents are as described.

8 Claims, No Drawings

(56) References Cited

U.S. PATENT DOCUMENTS

| | | | |
|---|---|---|---|
| 5,866,702 | A | 2/1999 | Mackman et al. |
| 6,608,053 | B2 | 8/2003 | Hayakawa et al. |
| 6,696,437 | B1 | 2/2004 | Lubisch et al. |
| 6,743,919 | B2 | 6/2004 | Koya et al. |
| 6,949,644 | B2 | 9/2005 | Ding et al. |
| 7,037,915 | B2 | 5/2006 | Hayakawa et al. |
| 7,122,665 | B2 | 10/2006 | Sun et al. |
| 7,138,402 | B2 | 11/2006 | Kasibhatla et al. |
| 7,750,002 | B2 | 7/2010 | Shuttleworth et al. |
| 7,776,856 | B2 | 8/2010 | Shuttleworth et al. |
| 7,781,433 | B2 | 8/2010 | Chuckowree et al. |
| 7,846,929 | B2 | 12/2010 | Folkes et al. |
| 7,888,352 | B2 | 2/2011 | Bayliss et al. |
| 7,893,059 | B2 | 2/2011 | Castanedo et al. |
| 7,893,060 | B2 | 2/2011 | Hancox et al. |
| 8,153,639 | B2 | 4/2012 | Chuckowree et al. |
| 8,158,624 | B2 | 4/2012 | Castanedo et al. |
| 8,158,625 | B2 | 4/2012 | Castanedo et al. |
| 8,158,626 | B2 | 4/2012 | Castanedo et al. |
| 8,168,633 | B2 | 5/2012 | Hancox et al. |
| 8,173,650 | B2 | 5/2012 | Castanedo et al. |
| 8,293,736 | B2 | 10/2012 | Li et al. |
| 2003/0139427 | A1 | 7/2003 | Castelhano et al. |
| 2003/0191312 | A1 | 10/2003 | Ding et al. |
| 2003/0236271 | A1 | 12/2003 | Hayakawa et al. |
| 2004/0019058 | A1 | 1/2004 | Bridger et al. |
| 2004/0198725 | A1 | 10/2004 | Sun et al. |
| 2005/0153989 | A1 | 7/2005 | Grotzfeld et al. |
| 2005/0165029 | A1 | 7/2005 | Patel et al. |
| 2005/0187217 | A1 | 8/2005 | Wilson et al. |
| 2005/0187389 | A1 | 8/2005 | Milanov et al. |
| 2005/0239806 | A1 | 10/2005 | Mehta et al. |
| 2006/0074124 | A1 | 4/2006 | Napper et al. |
| 2008/0039459 | A1 | 2/2008 | Folkes et al. |
| 2008/0058297 | A1 | 3/2008 | Ono et al. |
| 2008/0076758 | A1 | 3/2008 | Folkes et al. |
| 2008/0090861 | A1 | 4/2008 | Barrett et al. |
| 2008/0207611 | A1 | 8/2008 | Shuttleworth et al. |
| 2008/0233127 | A1 | 9/2008 | Bursavich et al. |
| 2008/0269210 | A1 | 10/2008 | Castanedo et al. |
| 2008/0269239 | A1 | 10/2008 | Harris et al. |
| 2009/0318411 | A1 | 12/2009 | Castanedo et al. |
| 2010/0069357 | A1 | 3/2010 | Bergeron et al. |
| 2010/0130492 | A1 | 5/2010 | Nakayama et al. |
| 2010/0130496 | A1 | 5/2010 | Goldsmith et al. |
| 2010/0216988 | A1 | 8/2010 | Alonso et al. |
| 2010/0305084 | A1 | 12/2010 | Castanedo et al. |
| 2010/0305096 | A1 | 12/2010 | Castanedo et al. |
| 2010/0331305 | A1 | 12/2010 | Bergeron et al. |
| 2011/0021496 | A1 | 1/2011 | Hancox et al. |
| 2011/0172216 | A1 | 7/2011 | Dotson et al. |
| 2011/0178117 | A1 | 7/2011 | Converso et al. |
| 2011/0207713 | A1 | 8/2011 | Castanedo et al. |
| 2011/0230464 | A1 | 9/2011 | Goldsmith et al. |
| 2012/0202785 | A1 | 8/2012 | Heald et al. |
| 2012/0308562 | A1 | 12/2012 | Derynck et al. |

FOREIGN PATENT DOCUMENTS

| | | |
|---|---|---|
| JP | 48072196 | 9/1973 |
| WO | 98/05335 A1 | 2/1998 |
| WO | 2004/021979 A2 | 3/2004 |
| WO | 2005/039506 A2 | 5/2005 |
| WO | 2006/020415 | 2/2006 |
| WO | 2006/046031 A1 | 5/2006 |
| WO | 2006/046031 R5 | 5/2006 |
| WO | 2007/122410 A1 | 11/2007 |
| WO | 2007/127183 A1 | 11/2007 |
| WO | 2007/129161 A2 | 11/2007 |
| WO | 2007/129161 A3 | 11/2007 |
| WO | 2008/023161 A1 | 2/2008 |
| WO | 2008/032162 A8 | 3/2008 |
| WO | 2008/039882 A1 | 4/2008 |
| WO | 2008/043031 A1 | 4/2008 |
| WO | 2008/073785 A2 | 6/2008 |
| WO | 2008/116129 A2 | 9/2008 |
| WO | 2008/116129 A3 | 9/2008 |
| WO | 2008/116910 A1 | 10/2008 |
| WO | 2008/152387 A1 | 12/2008 |
| WO | 2008/152390 A1 | 12/2008 |
| WO | 2008/152394 A1 | 12/2008 |
| WO | 2009/034386 A1 | 3/2009 |
| WO | 2009/045174 A1 | 4/2009 |
| WO | 2009/053716 A1 | 4/2009 |
| WO | 2009/081112 A2 | 7/2009 |
| WO | 2009/146406 A1 | 12/2009 |
| WO | 2009/153597 A3 | 12/2009 |
| WO | 2010/052569 A2 | 5/2010 |
| WO | 2010/052569 A3 | 5/2010 |
| WO | 2010/052569 A8 | 5/2010 |
| WO | 2010/059788 A1 | 5/2010 |
| WO | 2011/021038 A1 | 2/2011 |
| WO | 2011/029279 A1 | 3/2011 |
| WO | 2011/041399 A2 | 4/2011 |
| WO | 2011/041399 A3 | 4/2011 |
| WO | 2011/123751 A2 | 10/2011 |
| WO | 2011/163195 A1 | 12/2011 |

OTHER PUBLICATIONS

International Search Report and Written Opinion on patentability for International Patent Application No. PCT/US2011/065101.

Danopoulos et al., "Cu(II) and Pd(II) complexes with adenine and histidine derivatives" Inorg. Chim. Acta 55:141-45 ( 1981).

Ding et al., "Resin-Capture and Release Strategy toward Combinatorial Libraries of 2,6,9-Substituted Purines" J Comb Chem. 4(2):183-6 ( 2002).

Fiorini et al., "Solution-phase synthesis of 2,6,9-trisubstituted purines" Tetrahedron Letters 39(13):1827-30 ( 1998).

Gadhachanda et al., "4-Aminopyrimidines as novel HIV-1 inhibitors" Bioorg Med Chem Lett. 17(1):260-5 ( 2007).

Galal et al., "Synthesis and antitumor activity of novel benzimidazole-5-carboxylic acid derivatives and their transition metal complexes as topoisomerase II inhibitors" Eur J Med Chem. 45(12):5685-91 ( 2010).

Hammarstrom et al., "Utility of 4,6-dichloro-2-(methylthio)-5-nitropyrimidine. Part 3: Regioselective solid-phase synthesis of a 2,6,8,9-tetrasubstituted purine library" Tetrahedron Letters 48(16):2823-7 ( 2007).

Hayakawa et al., "Synthesis and biological evaluation of pyrido[3',2':4,5]furo[3,2-d]pyrimidine derivatives as novel PI3 kinase p110α inhibitors" Bioorg Med Chem Lett 17(9):2438-42 (May 2007).

Heffron et al., "Identification of GNE-477, a potent and efficacious dual PI3K/mTOR inhibitor" Bioorg Med Chem Lett. 20:2408-11 ( 2010).

Heffron et al., "Rational design of phosphoinositide 3-kinase α inhibitors that exhibit selectivity over the phosphoinositide 3-kinase β isoform" J Med Chem. 54:7815-33 ( 2011).

Hocek et al., "Regioselectivity in cross-coupling reactions of 2,6,8-trichloro-9-(tetrhydro-pyran-2-yl)purine: synthesis of 2,6,8-trisubstituted purine bases" Synthesis 17:2869-76 ( 2004).

Honigberg et al., "The Bruton tyrosine kinase inhibitor PCI-32765 blocks B-cell activation and is efficacious in models of autoimmune disease and B-cell malignancy" PNAS 107(29):13075-13080 (Jul. 20, 2010).

Huang et al., "Microwave-Assisted Rapid Synthesis of 2,6,9-Substituted Purines" J Comb Chem. 9(2):197-199 ( 2007).

International Search Report on patentability for International Patent Application No. PCT/US2009/045603 ( Sep. 21, 2009).

Liu et al., "Parallel solution-phase synthesis of a 2,6,8,9-tetrasubstituted purine library via a sulfur intermediate" J Comb Chem. 7(4):627-36 ( 2005).

Safina et al., "Discovery of Novel PI3-Kinase δ Specific Inhibitors for the Treatment" J. Med. Chem. 55:5887-5900 ( 2012).

Staben et al., "Structure-based design of thienobenzoxepin inhibitors of PI3-kinase" Bioorg Med Chem Lett. 21:4054-8 ( 2011).

Staben et al., "Structure-based optimization of pyrazolo-pyrimidine and -pyridine inhibitors of PI3-kinase" Bioorganic & Medicinal Chemistry Letters 20:6048-51 ( 2010).

(56) References Cited

OTHER PUBLICATIONS

Sutherlin et al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" J Med Chem 53(3):1086-1097 ( 2010).

Sutherlin et al., "Discovery of a potent, selective, and orally available class I phosphatidylinositol 3-kinase (PI3K)/mammalian target of rapamycin (mTOR) kinase inhibitor (GDC-0980) for the treament of cancer" J Med Chem. 54(21):7579-87 ( 2011).

Sutherlin et al., "Potent and selective inhibitors of PI3Kδ: Obtaining isoform selectivity from the affinity pocket and tryptophan shelf" Bioorganic & Medicinal Chemistry Letters 22:4296-4302 ( 2012).

Vandromme et al., "Suzuki-type Pd(O) coupling reactions in the synthesis of 2-arylpurines as Cdk inhibitors" Bioorg Med Chem Lett. 16(12):3144-3146 ( 2006).

Vazquez et al., "CD69 Gene is Differentially Regulated in T and B Cells by Evolutionarily Conserved Promoter-Distal Elements" J Immunol 183:6513-6521 ( 2009).

Wallin et al., "GDC-0980 is a novel class I PI3K/mTOR kinase inhibitor with robust activity in cancer models driven by the PI3K pathway" Mol Cancer Ther. 10(12):2426-36 ( 2011).

Written Opinion for International Search Report for International Patent Application No. PCT/EP2011/061930.

Yadava et al., "One-Pot Synthesis of Purinylpurine-2,6-Diones" Heterocycles 75(6):1489-92 ( 2008).

Yang et al., "Preparation of a fully substituted purine library" J Comb Chem. 7(3):474-82 ( 2005).

TRICYCLIC PI3K INHIBITOR COMPOUNDS AND METHODS OF USE

CROSS REFERENCE TO RELATED APPLICATIONS

This application is a divisional of U.S. Ser. No. 13/326,524, filed 15 Dec. 2011, now U.S. Pat. No. 8,883,799, issued 11 Nov. 2014, and claims the benefit under 35 USC §119(e) of U.S. Provisional Application Ser. No. 61/423,694 filed on 16 Dec. 2010, both of which are incorporated by reference in their entireties.

FIELD OF THE INVENTION

The invention relates generally to compounds with anti-cancer activity or anti-inflammatory activity, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol is one of a number of phospholipids found in cell membranes which play an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110α (alpha) (U.S. Pat. Nos. 5,824,492; 5,846,824; 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al (2008) J. Med. Chem. 51:5522-5532; Yaguchi et al (2006) Jour. of the Nat. Cancer Inst. 98(8):545-556).

Malignant gliomas are the most common primary brain tumors in adults. In glioblastoma (GBM), the most aggressive glioma subtype, tumor formation and growth appear to be driven by amplification or overexpression of gene products involved in growth factor-initiated signal transduction acting in cooperation with genetic alterations disrupting cell-cycle control (Holland E C (2001) Nat Rev Genet 2:120-129). Of the genomic alterations described in GBM, PTEN mutation and/or deletion is the most common, with an estimated frequency of 70-90% (Nutt C, Louis D N (2005) Cancer of the Nervous System (McGraw-Hill, New York), 2nd Ed, pp 837-847.). These findings, along with the prognostic value of PTEN status in GBM cases (Phillips H S, et al. (2006) Cancer Cell 9:157-163), suggest the importance of the phosphoinositide 3-kinase (PI3K)/Akt pathway in promoting highly aggressive glial malignancies, as well as the opportunities for treatment with PI3K inhibitors possessing blood-brain barrier penetrant properties.

Malignant gliomas are treated with a combination of surgery, radiation, and temozolomide (TEMODAR™), but these therapies ultimately fail at a high frequency due to tumor recurrence. Additional therapies are needed for delivery of effective concentrations of effective drugs to the brain to treat hyperproliferative disorders, such as glioblastoma and metastatic brain cancer.

SUMMARY OF THE INVENTION

The invention relates generally to tricyclic PI3K inhibitor compounds of Formula I with anti-cancer activity, anti-inflammatory activity, or immunoregulatory properties, and more specifically with PI3 kinase modulating or inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the tricyclic PI3K inhibitor compounds of Formula I for in vitro, in situ, and in vivo diagnosis or treatment of mammalian cells, organisms, or associated pathological conditions.

Formula I compounds include:

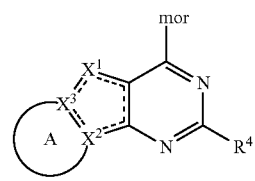

and stereoisomers, geometric isomers, tautomers, and pharmaceutically acceptable salts thereof. The dashed lines indicate an optional double bond, and at least one dashed line is a double bond. The substituents are as described herein.

Another aspect of the invention provides a pharmaceutical composition comprising a tricyclic PI3K inhibitor compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I.

Another aspect of the invention provides methods of preventing or treating a hyperproliferative disease or disorder modulated by PI3 kinases, comprising administering to a mammal in need of such treatment an effective amount of a compound of Formula I. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, alone or in combination with one or more additional compounds having anti-hyperproliferative properties.

In a further aspect the present invention provides a method of using a compound of this invention to treat a hyperproliferative disease or condition modulated by PI3 kinase in a mammal.

An additional aspect of the invention is the use of a compound of this invention for treating cancer modulated by PI3 kinase in a mammal.

Another aspect of the invention includes kits comprising a compound of Formula I, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—$CH=CH$—), allyl (—$CH_2CH=CH$—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, e.g., as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C$_6$-C$_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g.: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Formula I Tricyclic PI3K Inhibitor Compounds

The present invention provides tricyclic PI3K inhibitor compounds of Formula I, and pharmaceutical formulations thereof, which are potentially useful in the treatment of diseases, conditions and/or disorders modulated by PI3 kinases. More specifically, the present invention provides compounds of Formula I:

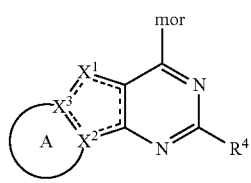

and stereoisomers, geometric isomers, tautomers, and pharmaceutically acceptable salts thereof, wherein:

the dashed lines indicate an optional double bond, and at least one dashed line is a double bond;

$X^1$ is S, O, N, $NR^a$, $CR^1$, $C(R^1)_2$, or —$C(R^1)_2O$—;

$X^2$ is C, $CR^2$ or N;

$X^3$ is C, $CR^3$ or N;

A is a 5, 6, or 7-membered carbocyclyl or heterocyclyl ring fused to $X^2$ and $X^3$, optionally substituted with one or more $R^5$ groups;

$R^a$ is H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^1$, $R^2$, and $R^3$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^4$ is selected from $C_6$-$C_{20}$ aryl, $C_2$-$C_{20}$ heterocyclyl and $C_1$-$C_{20}$ heteroaryl, each of which are optionally substituted with one or more groups $R^6$ groups independently selected from F, Cl, Br, I, —$CH_3$, —$CH_2CH_3$, —$CH(CH_3)_2$, —$CH_2CH(CH_3)_2$, —$CH_2CH_3$, —$CH_2CN$, —CN, —$CF_3$, —$CH_2OH$, —$CO_2H$, —$CONH_2$, —$CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —NHC(=O)$NHCH_3$, —NHC(=O)$NHCH_2CH_3$, —$NHS(O)_2CH_3$, —$N(CH_3)C(=O)OC(CH_3)_3$, —$S(O)_2CH_3$, benzyl, benzyloxy, morpholinyl, morpholinomethyl, and 4-methylpiperazin-1-yl; and $R^5$ is independently selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl); or two geminal $R^5$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

mor is selected from:

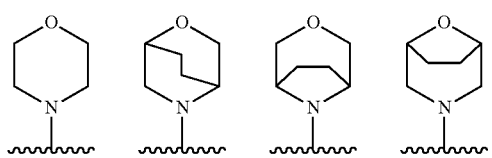

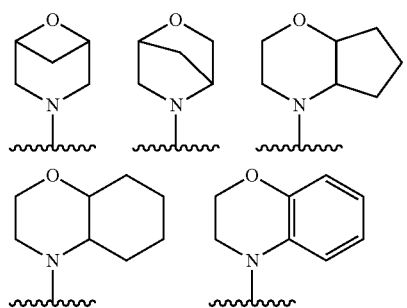

optionally substituted with one or more $R^7$ groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2OH$, —$CH(CH_3)OH$, —$CH(CH_2CH_3)OH$, —$CH_2CH(OH)CH_3$, —$C(CH_3)_2OH$, —$C(CH_3)_2OCH_3$, —$CH(CH_3)F$, —$C(CH_3)F_2$, —$CH(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —$NHCH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, =O, —OH, —$OCH_3$, —$OCH_2CH_3$, —$OCH(CH_3)_2$, —SH, —NHC(=O)$NHCH_3$, —NHC(=O)$NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, and —$CH_2S(O)_2CH_3$.

Further it is to be understood that every embodiment relating to a specific residue $X^1$, $X^2$, $X^3$, A, $R^a$, $R^1$, $R^2$, $R^3$, $R^4$, $R^5$, $R^6$, $R^7$ and mor as disclosed herein may be combined with any other embodiment relating to another residue $X^1$, $X^2$, $X^3$, A, $R^a$, $R^1$, $R^2$, $R^3$, $R^4$, $R^5$, $R^6$, $R^7$ and mor as disclosed herein.

Exemplary embodiments of compounds of the invention include Formulas Ia-n:

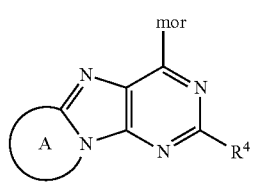

Ia

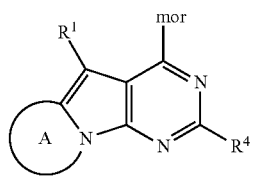

Ib

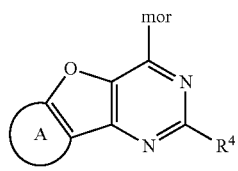

Ic

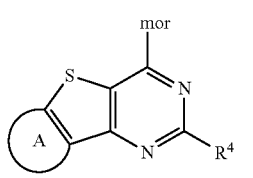
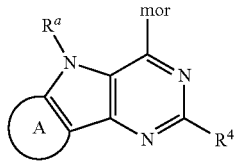
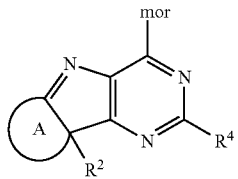
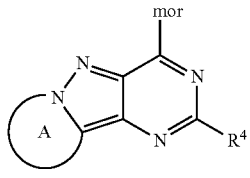
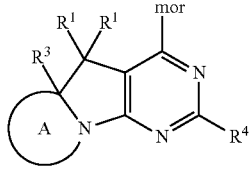
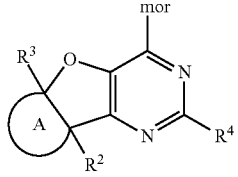
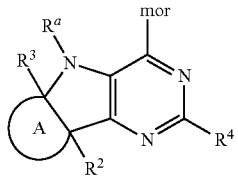
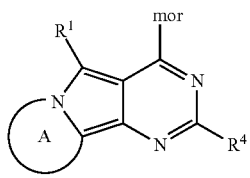
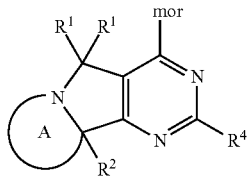
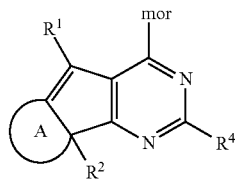
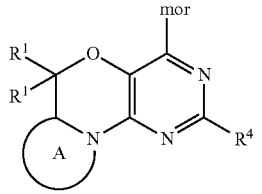
Exemplary embodiments of Formula I compounds include:
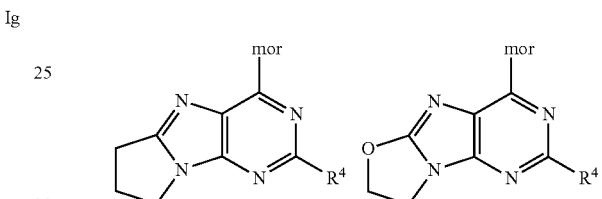
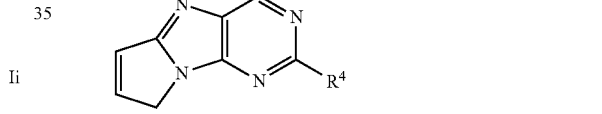
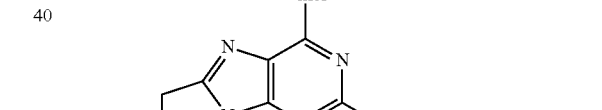
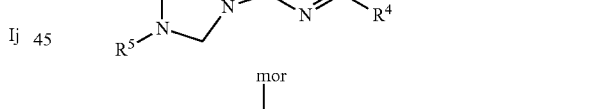
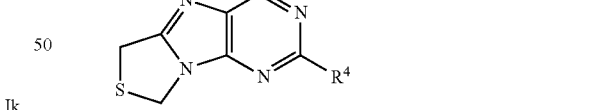
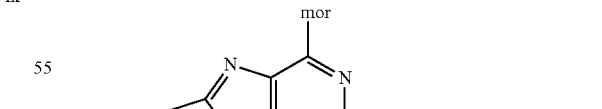
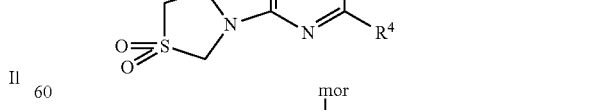
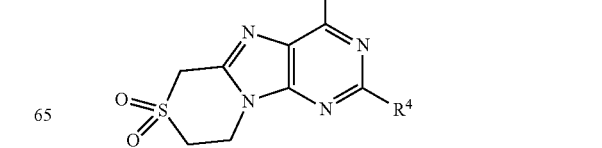

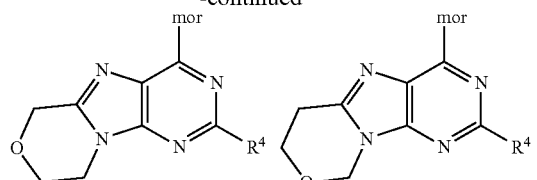
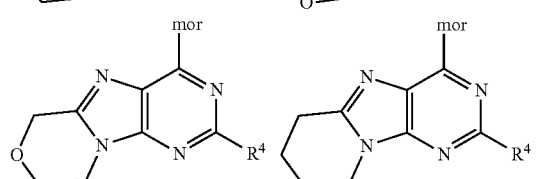
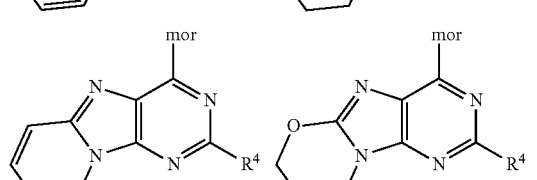
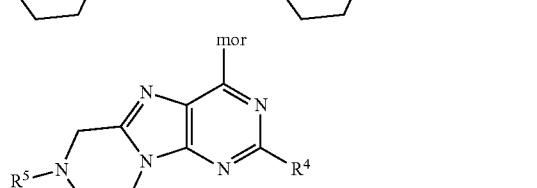
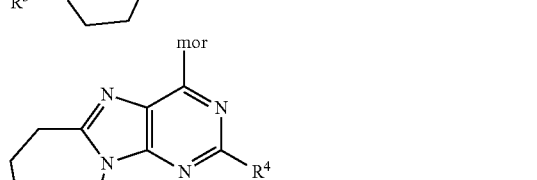
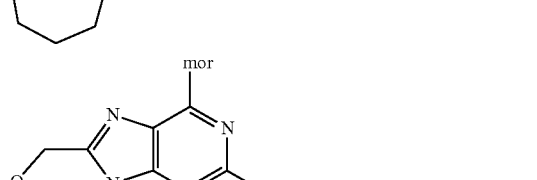
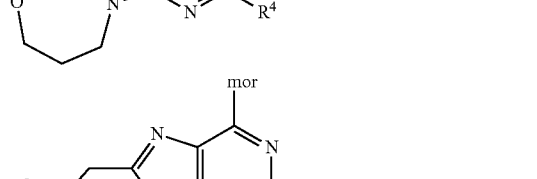
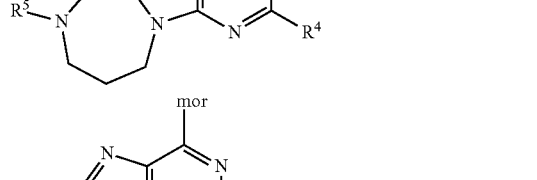
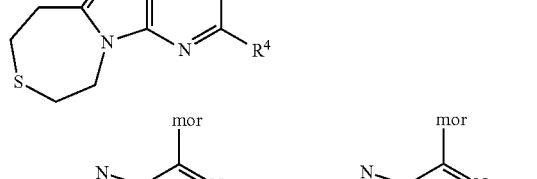
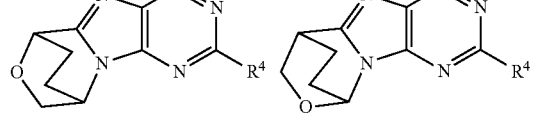
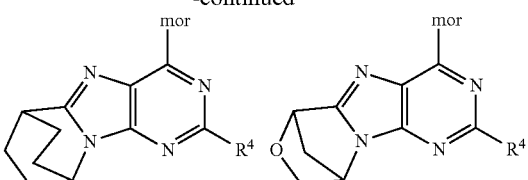
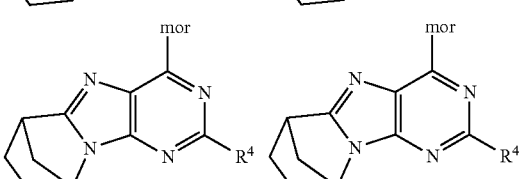
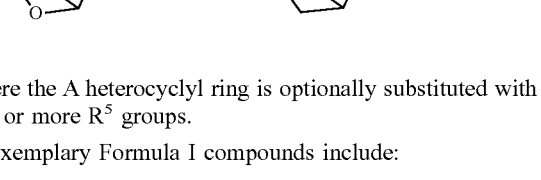
where the A heterocyclyl ring is optionally substituted with one or more $R^5$ groups.
Exemplary Formula I compounds include:
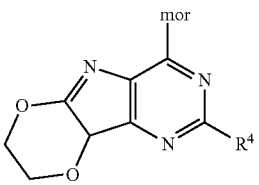
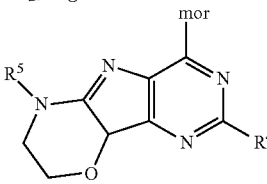
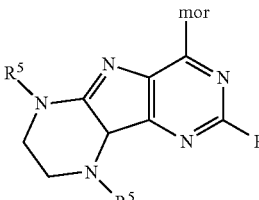
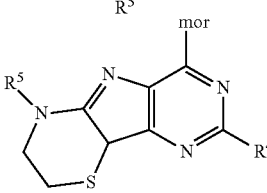
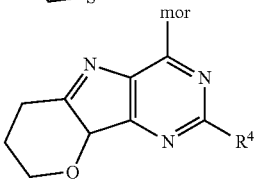
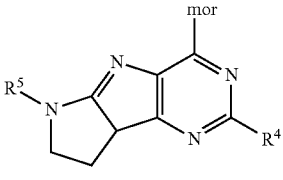
where the A heterocyclyl ring is optionally substituted with one or more $R^5$ groups.

In exemplary Formula I compounds, the A heterocyclyl ring is optionally substituted with one, two or three $R^5$ groups.

In exemplary Formula I compounds, the A heterocyclyl ring is optionally substituted with two $R^5$ groups.

Exemplary Formula I compounds include two geminal $R^5$ groups which form cyclopropyl, cyclobutyl, cyclopentyl, tetrahydrofuryl, tetrahydropyranyl, oxetanyl, azetidinyl, pyrrolidinyl, piperidyl, piperazinyl, cyclohexyl, morpholino, or 1,1-dioxo-thiopyran-4-yl.

Exemplary Formula I compounds include wherein $R^4$ is phenyl substituted with one or more groups selected from F, Cl, Br, I, —$CH_3$, —$CH_2CH_3$, —$CH(CH_3)_2$, —CN, —$CF_3$, —$CH_2H$, —$CO_2H$, —$CONH_2$, —$CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —$NHC(=O)NHCH_3$, —$NHC(=O)NHCH_2CH_3$, —$NHS(O)_2CH_3$, —$N(CH_3)C(=O)OC(CH_3)_3$, and —$S(O)_2CH_3$.

Exemplary Formula I compounds include wherein $R^4$ is an optionally substituted bicyclic heteroaryl group selected from 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine.

Exemplary Formula I compounds include wherein optionally substituted $R^4$ is selected from:

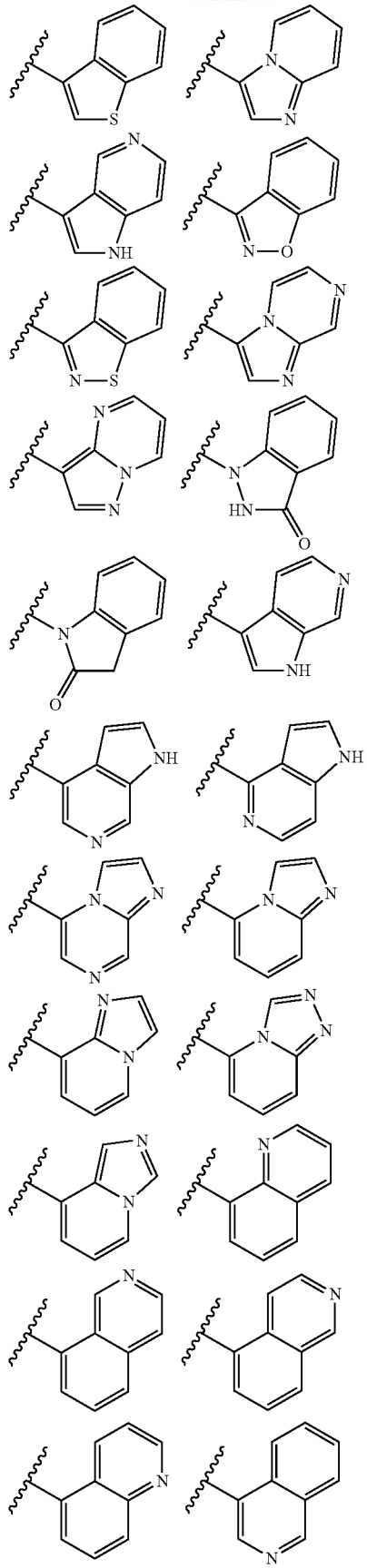

-continued

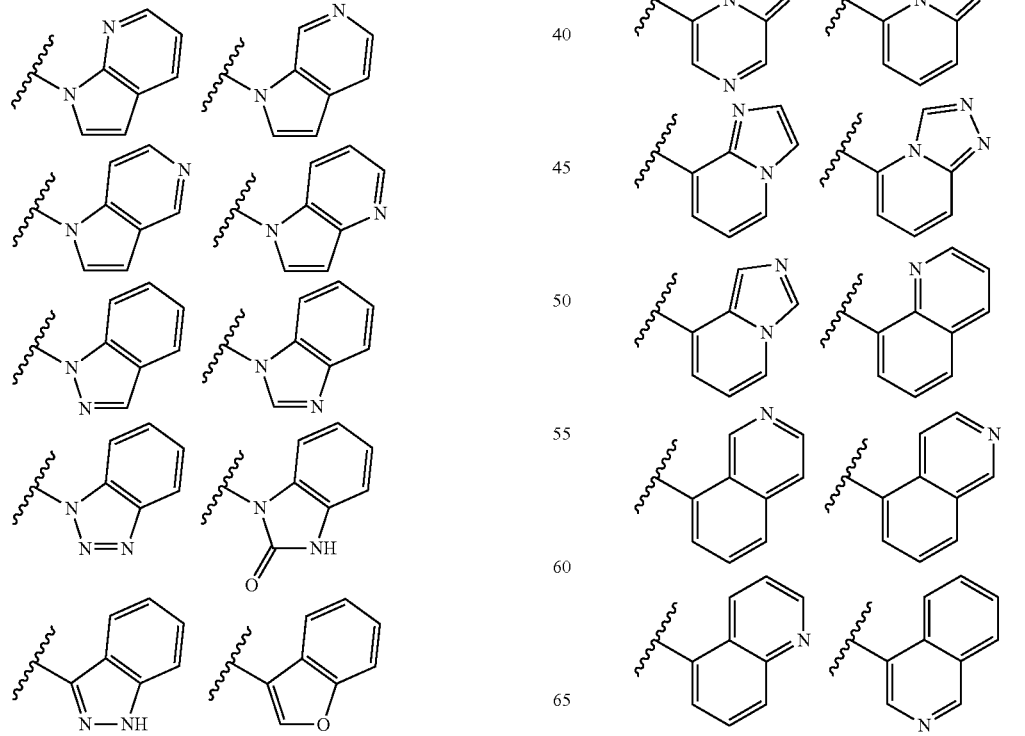

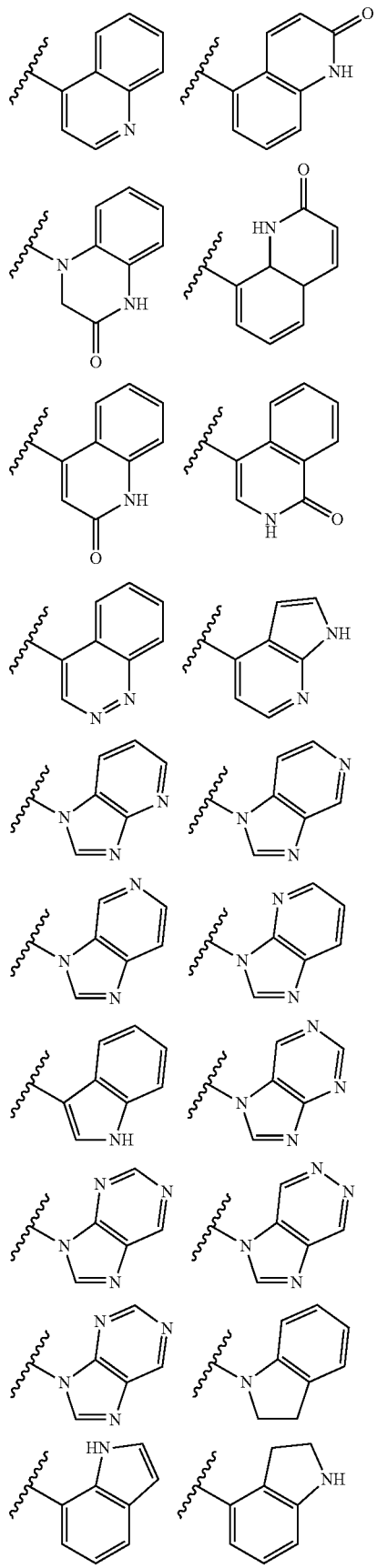

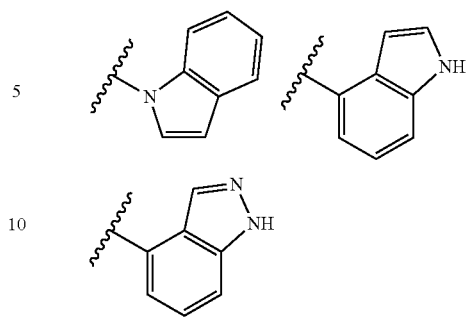

where the wavy line indicates the site of attachment.

Exemplary Formula I compounds include wherein optionally substituted $R^4$ is selected from:

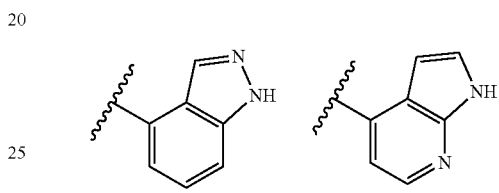

where the wavy line indicates the site of attachment.

In one embodiment of the invention $R^4$ is 1H-indazol-4-yl.

Exemplary Formula I compounds include wherein $R^4$ is an optionally substituted monocyclic heteroaryl group selected from 2-furanyl, 3-furanyl, 2-imidazolyl, 4-imidazolyl, 3-isoxazolyl, 4-isoxazolyl, 5-isoxazolyl, 2-oxazolyl, 4-oxazolyl, 5-oxazolyl, 3-pyrazolyl, 4-pyrazolyl, 2-pyrazinyl, 3-pyridazinyl, 4-pyridazinyl, 5-pyridazinyl, 2-pyrimidinyl, 5-pyrimidinyl, 6-pyrimidinyl, 2-pyridyl, 3-pyridyl, 4-pyridyl, 2-pyrrolyl, 3-pyrrolyl, 2-thienyl, 3-thienyl, 5-tetrazolyl, 1-tetrazolyl, 2-tetrazolyl, 2-thiazolyl, 4-thiazolyl, 5-thiazolyl, 3-triazolyl, and 1-triazolyl.

Exemplary Formula I compounds include optionally substituted $R^4$ is selected from:

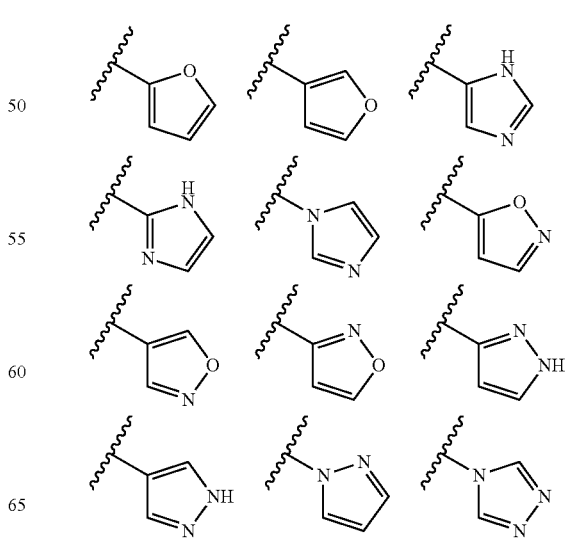

-continued

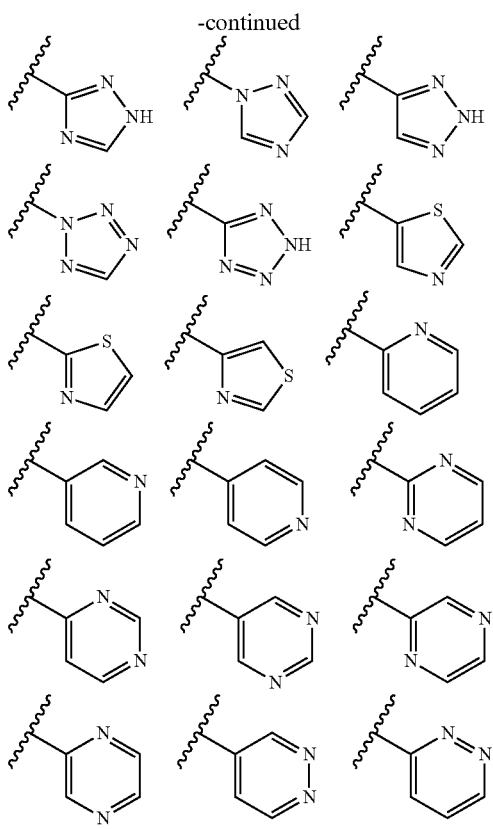

where the wavy line indicates the site of attachment.

Exemplary Formula I compounds include wherein $R^4$ is an optionally substituted monocyclic heteroaryl group selected from pyridyl, pyrimidinyl or pyrazolyl.

Exemplary Formula I compounds include wherein $R^4$ is an optionally substituted pyrimidinyl.

In one embodiment of the invention $R^4$ is 2-aminopyrimidin-5-yl.

Exemplary Formula I compounds include optionally substituted $R^4$:

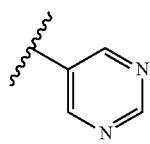

where the wavy line indicates the site of attachment.
Exemplary Formula I compounds include mor:

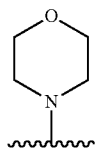

where the wavy line indicates the site of attachment, optionally substituted with one or more $R^7$ groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, and —CH$_2$S(O)$_2$CH$_3$.

In one embodiment of the invention, one or more $R^5$ groups are C$_1$-C$_{12}$ alkyl optionally substituted with one or more groups selected from F, Cl, Br, I, —CH$_3$, —CH$_2$CH$_3$, —C(CH$_3$)$_3$, —CH$_2$OH, —CH$_2$CH$_2$OH, —C(CH$_3$)$_2$OH, —CH$_2$OCH$_3$, —CN, —CH$_2$F, —CHF$_2$, —CF$_3$, —CO$_2$H, —COCH$_3$, —COC(CH$_3$)$_3$, —CO$_2$CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —S(O)$_2$CH$_3$, cyclopropyl, cyclobutyl, oxetanyl, morpholino, and 1,1-dioxo-thiopyran-4-yl.

In one embodiment of the invention, $R^5$ is methyl optionally substituted with one or more groups as defined herein. In one embodiment such substituents are F, OH and =O.

In one embodiment of the invention one or more $R^5$ groups are independently selected from F, Cl, Br, I, —CH$_3$, —CH$_2$CH$_3$, —C(CH$_3$)$_3$, —CH$_2$OH, —CH$_2$CH$_2$OH, —C(CH$_3$)$_2$OH, —CH$_2$OCH$_3$, —CN, —CH$_2$F, —CHF$_2$, —CF$_3$, —CO$_2$H, —COCH$_3$, —COC(CH$_3$)$_3$, —CO$_2$CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —S(O)$_2$CH$_3$, cyclopropyl, cyclobutyl, oxetanyl, morpholino, and 1,1-dioxo-thiopyran-4-yl.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$ (D), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

Determination of the PI3 kinase activity of a Formula I compound is possible by a number of direct and indirect detection methods. Certain exemplary compounds described herein were assayed for their p110α (alpha), and other isoform, PI3K binding activity (Example 901) and in vitro activity against tumor cells (Example 902). Certain exemplary compounds of the invention had PI3K binding activity $IC_{50}$ values less than 10 nM. Certain compounds of the invention had tumor cell-based activity $EC_{50}$ values less than 100 nM.

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 902). Cell-based in vitro assays were used to measure viability, i.e. proliferation ($IC_{50}$), cytotoxicity ($EC_{50}$), and induction of apoptosis (caspase activation).

The in vitro potency of Formula I exemplary compounds was measured by the cell proliferation assay, CellTiter-Glo® Luminescent Cell Viability Assay, commercially available from Promega Corp., Madison, Wis. (Example 902). This homogeneous assay method is based on the recombinant expression of Coleoptera luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) Anti-Cancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds were measured by the CellTiter-Glo® Assay (Example 902) against several tumor cell lines. Potency $EC_{50}$ values were established for the tested compounds. The range of in vitro cell potency activities was about 100 nM to about 10 μM. Certain tested compounds had $EC_{50}$ values of less than 1 micromolar (1 μM) in stopping proliferation of certain tumor cell lines.

Certain ADME properties were measured for certain exemplary compounds by assays including: Caco-2 Permeability (Example 903), Hepatocyte Clearance (Example 904), Cytochrome P450 Inhibition (Example 905), Cytochrome P450 Induction (Example 906), Plasma Protein Binding (Example 907), and hERG channel blockage (Example 908).

Certain exemplary compounds were tested for efficacy in dose escalation studies in tumor-bearing Taconic NCR nude mouse models (Example 909). The U-87 MG Merchant (an in-house variant derived from U-87 MG cells from ATCC, Manassas, Va.) subcutaneous xenograft mouse model was employed to test Formula I compounds at escalating doses along with Vehicle (MCT, negative control). Tumor growth delay was measured following once daily oral dosing for <28 days. Body weight change over the course of treatment was measured as an indicator of safety. The dose- and time-dependent pharmacokinetic and pharmacodynamic response of drug administration in this same subcutaneous tumor xenograft model was also examined (Example 913).

Blood-brain barrier penetrant [properties] potential was assessed in vitro using MDCK cells stably transfected with P-glycoprotein (MDR1) or bcrp1 (Example 911). Brain penetration was determined in vivo by measuring compound concentrations (Example 912) and/or by measuring the modulation of the PI3K pathway (Example 913) in the brain of mice following a single IV or oral dose. Brain tumor efficacy was measured in Example 914 by GS-2 (human glioblastoma muliforme (GBM) engineered to express luciferase). The effect of once daily oral dosing on the growth of GS-2 intracranial implants was evaluated by magnetic resonance imaging (MRI). Mice with tumor xenografts of U-87 MG cells were dosed with drug or vehicle and samples were analyzed for PK, PD, and/or IHC analysis (Example 915).

Exemplary Formula I compounds No. 101-177 in Table 1 were made, characterized, and tested for inhibition of PI3K alpha ($IC_{50}$ or $K_i$ binding to p110 alpha less than 1 micromolar, μM) and selectivity according to the methods of this invention, and have the following structures and corresponding names (ChemBioDraw Ultra, Version 11.0, CambridgeSoft Corp., Cambridge Mass.).

TABLE 1

| No. | Structure | Name | $IC_{50}$, Ki (mole) PI3K, p110 alpha binding assay |
|---|---|---|---|
| 101 | 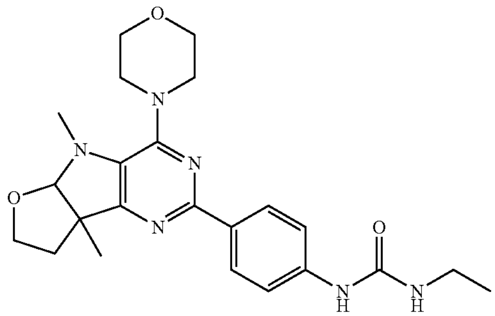 | 1-[4-(3a,8-dimethyl-7-morpholin-4-yl-3,3a,8,8a-tetrahydro-2h-1-oxa-4,6,8-triaza-cyclopenta[a]inden-5-yl)-phenyl]-3-ethyl-urea | 2.1 |
| 102 | 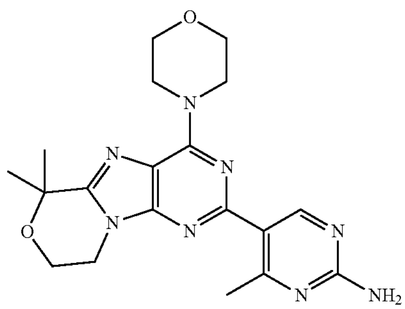 | 5-(6,6-dimethyl-4-morpholino-8,9-dihydro-6h-[1,4]oxazine[3,4-e]purin-2-yl)-4-methylpyrimidin-2-amine | 0.0018 |
| 103 | 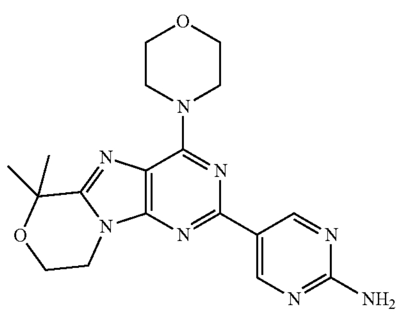 | 5-(6,6-dimethyl-4-morpholino-8,9-dihydro-6h-[1,4]oxazino[3,4-e]purin-2-yl)pyrimidin-2-amine | 0.00209 |
| 104 | 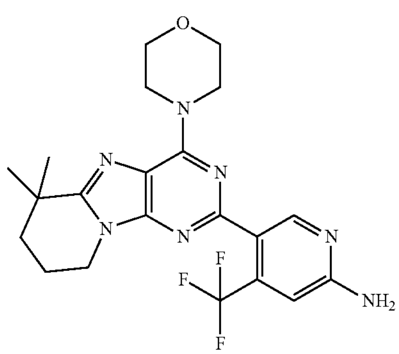 | 5-(6,6-dimethyl-4-morpholino-8,9-dihydro-6h-[1,4]oxazino[3,4-e]purin-2-yl)-4-(trifluoromethyl)pyridyl-2-amine | 0.00389 |

TABLE 1-continued
| No. | Structure | Name | IC$_{50}$, Ki (mole) PI3K, p110 alpha binding assay |
|---|---|---|---|
| 105 | 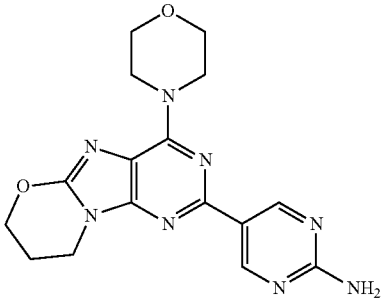 | 5-(4-morpholino-8,9-dihydro-7h-[1,3]oxazino[2,3-e]purin-2-yl)pyrimidin-2-amine | 0.00684 |
| 106 | 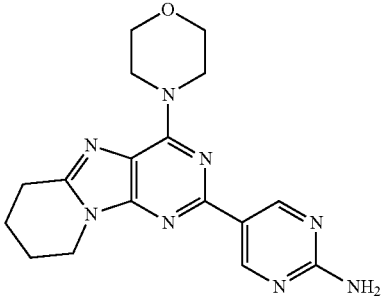 | 5-(4-morpholino-6,7,8,9-tetrahydropyrido[2,1-e]purin-2-yl)pyrimidin-2-amine | 0.00388 |
| 107 | 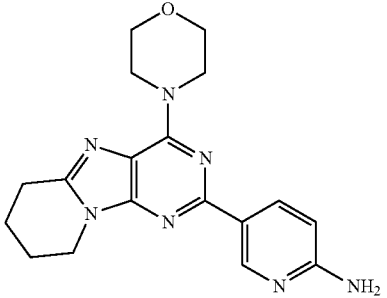 | 5-(4-morpholino-6,7,8,9-tetrahydropyrido[2,1-e]purin-2-yl)pyridin-2-amine | 0.0507 |
| 108 | 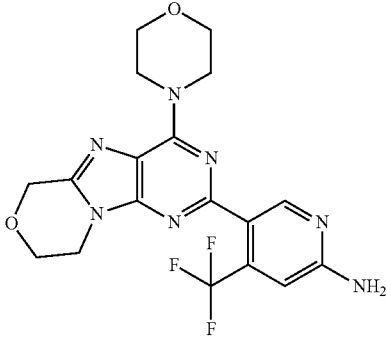 | 5-(4-morpholino-8,9-dihydro-6h-[1,4]oxazino[3,4-e]purin-2-yl)-4-(trifluoromethyl)pyridyl-2-amine | 0.0112 |

TABLE 1-continued

| No. | Structure | Name | IC$_{50}$, Ki (mole) PI3K, p110 alpha binding assay |
|---|---|---|---|
| 109 | 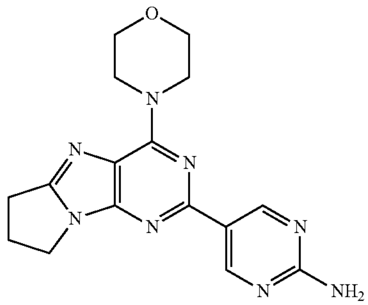 | 5-(4-morpholino-7,8-dihydro-6h-pyrrolo[2,1-e]purin-2-yl)pyrimidin-2-amine | 0.00826 |
| 110 | 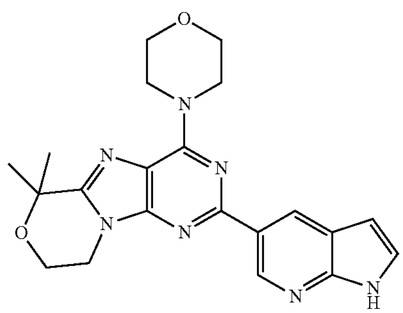 | 6,6-dimethyl-4-morpholino-2-(1H-pyrrolo[2,3-b]pyridin-5-yl)-8,9-dihydro-6H-[1,4]oxazino[3,4-e]purine | 0.0140 |
| 111 | 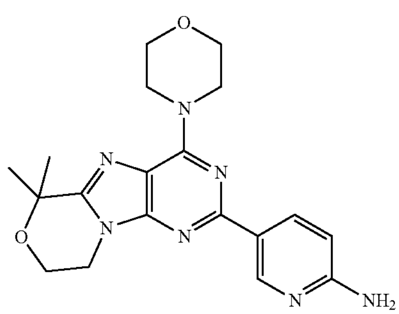 | 5-(6,6-dimethyl-4-morpholino-8,9-dihydro-6H-[1,4]oxazino[3,4-e]purin-2-yl)pyridin-2-amine | 0.0186 |
| 112 | 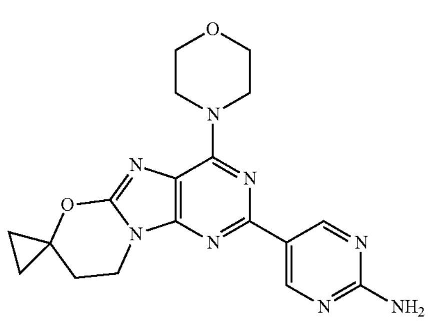 | 5-(4-morpholino-8,9-dihydrospiro[[1,3]oxazino[2,3-e]purine-7,1'-cyclopropane]-2-yl)pyrimidin-2-amine | 0.00137 |

TABLE 1-continued

| No. | Structure | Name | IC$_{50}$, Ki (mole) PI3K, p110 alpha binding assay |
|---|---|---|---|
| 113 | 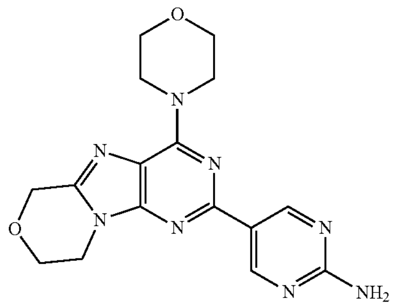 | 5-(4-morpholino-8,9-dihydro-6h-[1,4]oxazino[3,4-e]purin-2-yl)pyrimidin-2-amine | 0.00432 |
| 114 | 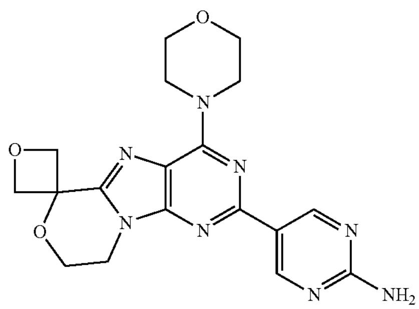 | 5-(4-morpholino-8,9-dihydrospiro[[1,4]oxazino[3,4-e]purine-6,3'-oxetane]-2-yl)pyrimidin-2-amine | 0.00245 |
| 115 | 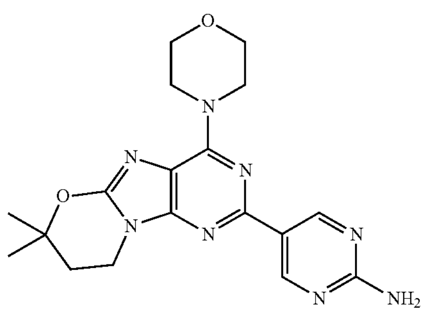 | 5-(7,7-dimethyl-4-morpholino-8,9-dihydro-7h-[1,3]oxazino[2,3-e]purin-2-yl)pyrimidin-2-amine | 0.00509 |
| 116 | 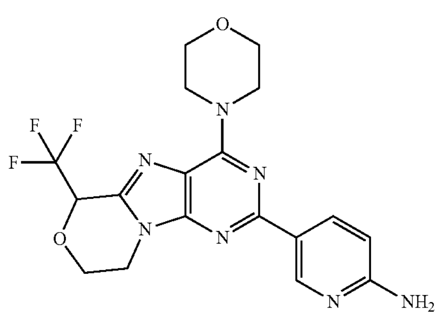 | 5-(4-morpholino-6-(trifluoromethyl)-8,9-dihydro-6H-[1,4]oxazino[3,4-e]purin-2-yl)pyridin-2-amine | 0.0452 |

TABLE 1-continued

| No. | Structure | Name | IC$_{50}$, Ki (mole) PI3K, p110 alpha binding assay |
|---|---|---|---|
| 117 | 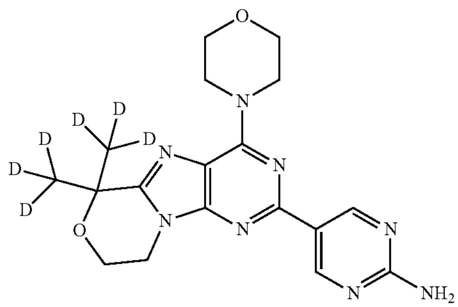 | 5-(6,6-(hexadeuterio)dimethyl-4-morpholino-8,9-dihydro-6h-[1,4]oxazino[3,4-e]purin-2-yl)pyrimidin-2-amine | 0.00259 |
| 118 | 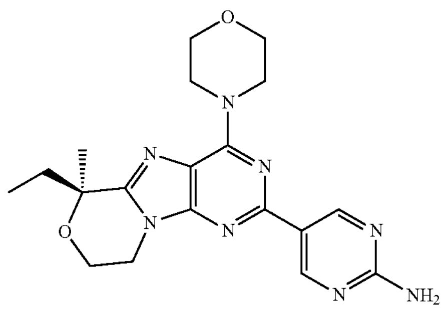 | (S)-5-(6-ethyl-6-methyl-4-morpholino-8,9-dihydro-6H-[1,4]oxazino[3,4-e]purin-2-yl)pyrimidin-2-amine | 0.00311 |
| 119 | 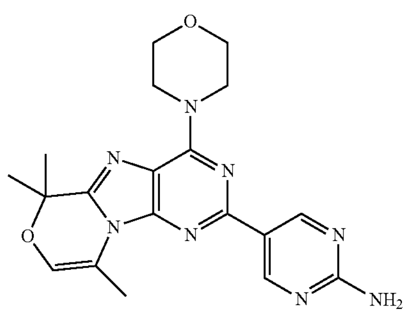 | 5-(6,6,9-trimethyl-4-morpholino-6h-[1,4]oxazino[3,4-e]purin-2-yl)pyrimidin-2-amine | 0.00473 |
| 120 | 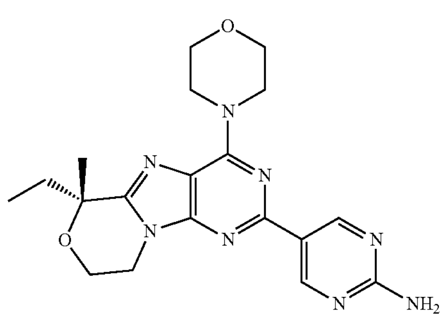 | (R)-5-(6-ethyl-6-methyl-4-morpholino-8,9-dihydro-6H-[1,4]oxazino[3,4-e]purin-2-yl)pyrimidin-2-amine | 0.00596 |

TABLE 1-continued

| No. | Structure | Name | IC$_{50}$, Ki (mole) PI3K, p110 alpha binding assay |
|---|---|---|---|
| 121 | 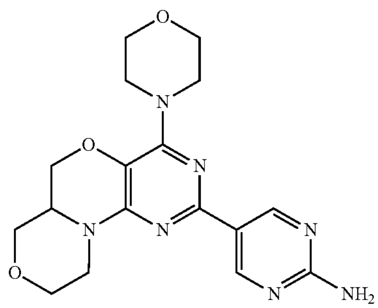 | 5-(1-morpholin-4-yl-5,6,8a,9-tetrahydro-8h-7,10-dioxa-2,4,4b-triaza-phenanthren-3-yl)-pyrimidin-2-ylamine | 0.00572 |
| 122 | 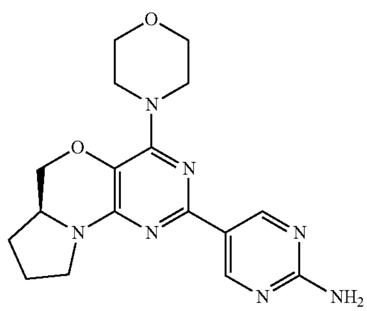 | 5-((S)-6-Morpholin-4-yl-2,3,3a,4-tetrahydro-1H-5-oxa-7,9,9b-triaza-cyclopenta[a]naphthalen-8-yl)-pyrimidin-2-ylamine | 0.0779 |
| 123 | 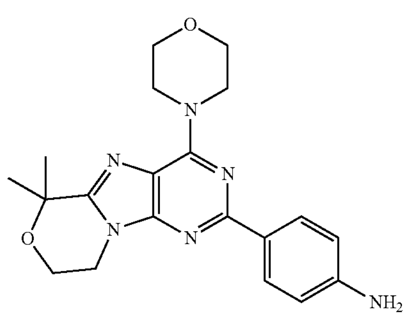 | 4-(6,6-dimethyl-4-morpholino-8,9-dihydro-6H-[1,4]oxazino[3,4-e]purin-2-yl)aniline | 0.541 |
| 124 | 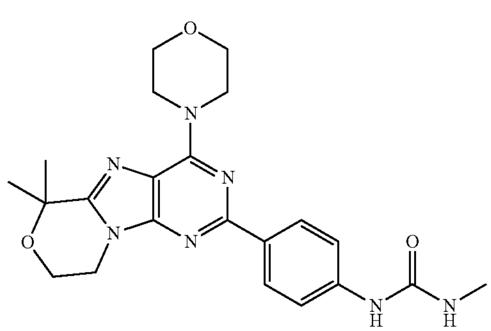 | 1-(4-(6,6-dimethyl-4-morpholino-8,9-dihydro-6H-[1,4]oxazino[3,4-e]purin-2-yl)phenyl)-3-methylurea | 0.00671 |

TABLE 1-continued

| No. | Structure | Name | IC$_{50}$, Ki (mole) PI3K, p110 alpha binding assay |
|---|---|---|---|
| 125 | 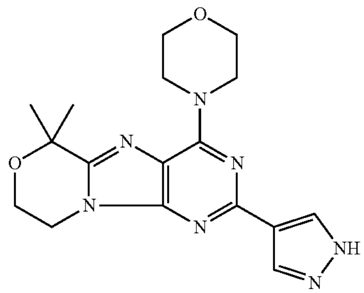 | 6,6-dimethyl-4-morpholino-2-(1H-pyrazol-4-yl)-8,9-dihydro-6H-[1,4]oxazino[3,4-e]purine | 0.382 |
| 126 | 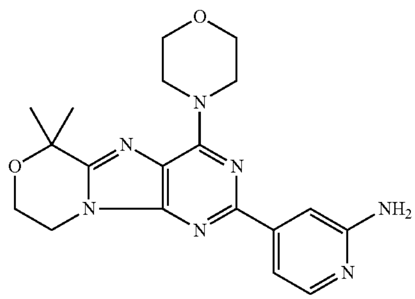 | 4-(6,6-dimethyl-4-morpholino-8,9-dihydro-6H-[1,4]oxazino[3,4-e]purin-2-yl)pyridin-2-amine | 0.685 |
| 127 | 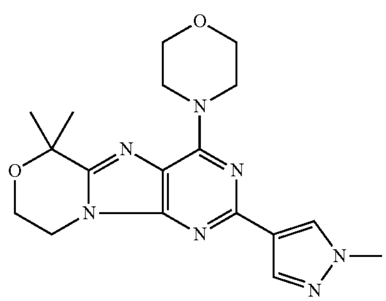 | 6,6-dimethyl-2-(1-methyl-1H-pyrazol-4-yl)-4-morpholino-8,9-dihydro-6H-[1,4]oxazino[3,4-e]purine | >0.695 |
| 128 | 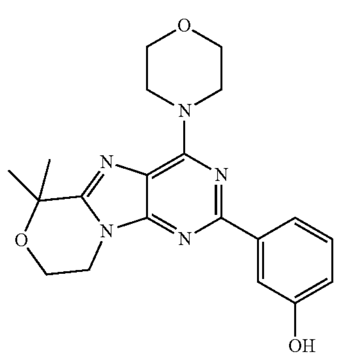 | 3-(6,6-dimethyl-4-morpholino-8,9-dihydro-6H-[1,4]oxazino[3,4-e]purin-2-yl)phenol | 0.00458 |

TABLE 1-continued

| No. | Structure | Name | IC$_{50}$, Ki (mole) PI3K, p110 alpha binding assay |
|---|---|---|---|
| 129 | 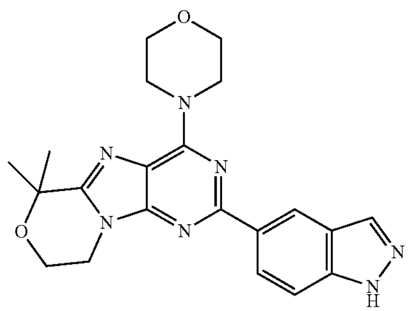 | 2-(1H-indazol-5-yl)-6,6-dimethyl-4-morpholino-8,9-dihydro-6H-[1,4]oxazino[3,4-e]purine | >0.695 |
| 130 | 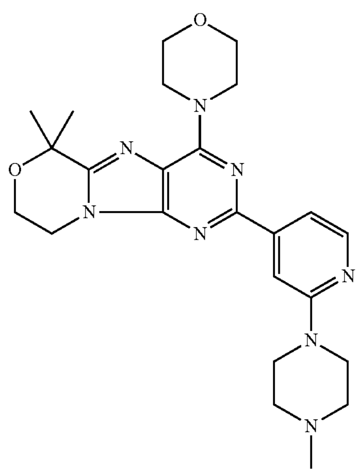 | 6,6-dimethyl-2-(2-(4-methylpiperazin-1-yl) yridine-4-yl)-4-morpholino-8,9-dihydro-6H-[1,4]oxazino[3,4-e]purine | >0.695 |
| 131 | 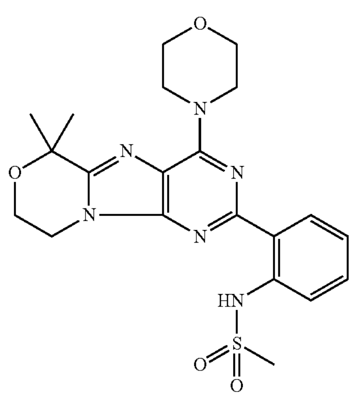 | N-(2-(6,6-dimethyl-4-morpholino-8,9-dihydro-6H-[1,4]oxazino[3,4-e]purin-2-yl)phenyl)methanesulfonamide | 0.638 |
| 132 | 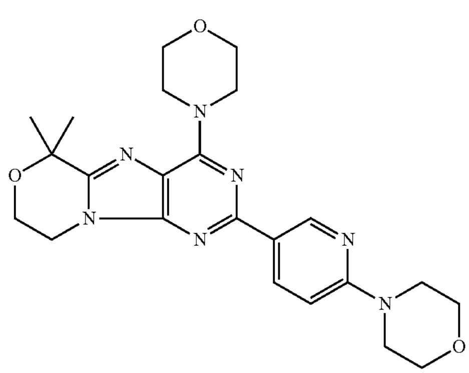 | 6,6-dimethyl-4-morpholino-2-(6-morpholinopyridin-3-yl)-8,9-dihydro-6H-[1,4]oxazino[3,4-e]purine | >0.695 |

TABLE 1-continued

| No. | Structure | Name | IC$_{50}$, Ki (mole) PI3K, p110 alpha binding assay |
|---|---|---|---|
| 133 | 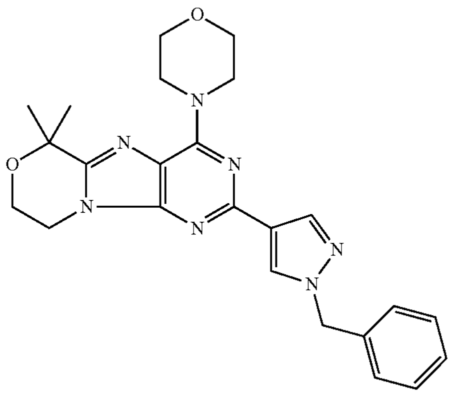 | 2-(1-benzyl-1H-pyrazol-4-yl)-6,6-dimethyl-4-morpholino-8,9-dihydro-6H-[1,4]oxazino[3,4-e]purine | >0.695 |
| 134 | 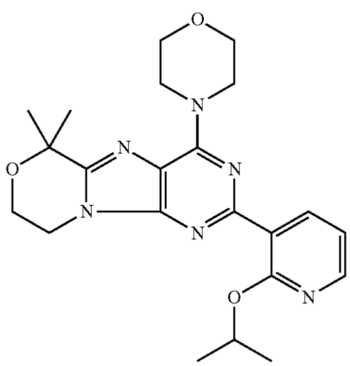 | 2-(2-isopropoxypyridin-3-yl)-6,6-dimethyl-4-morpholino-8,9-dihydro-6H-[1,4]oxazino[3,4-e]purine | >0.695 |
| 135 | 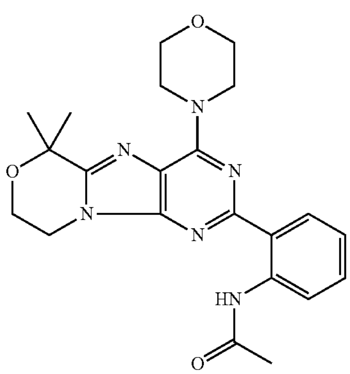 | N-(2-(6,6-dimethyl-4-morpholino-8,9-dihydro-6H-[1,4]oxazino[3,4-e]purin-2-yl)phenyl)acetamide | >0.695 |
| 136 | 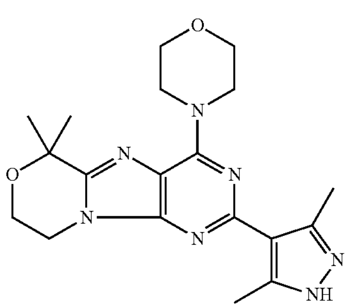 | 2-(3,5-dimethyl-1H-pyrazol-4-yl)-6,6-dimethyl-4-morpholino-8,9-dihydro-6H-[1,4]oxazino[3,4-e]purine | >0.695 |

TABLE 1-continued

| No. | Structure | Name | IC$_{50}$, Ki (mole) PI3K, p110 alpha binding assay |
|---|---|---|---|
| 137 | 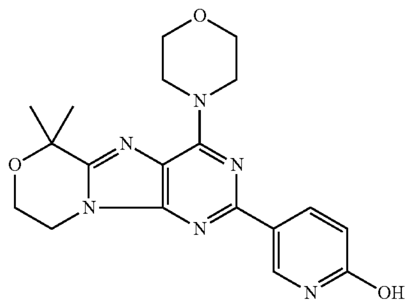 | 5-(6,6-dimethyl-4-morpholino-8,9-dihydro-6H-[1,4]oxazino[3,4-e]purin-2-yl)pyridine-2-ol | >0.695 |
| 138 | 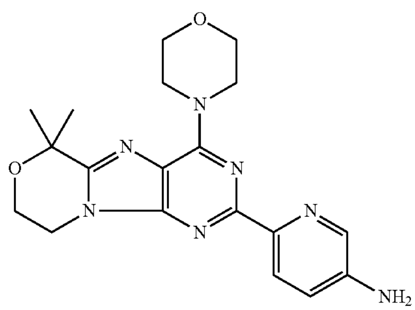 | 6-(6,6-dimethyl-4-morpholino-8,9-dihydro-6H-[1,4]oxazino[3,4-e]purin-2-yl)pyridine-3-amine | >0.695 |
| 139 | 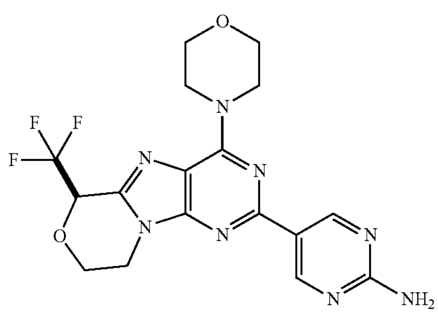 | (R)-5-(4-morpholino-6-(trifluoromethyl)-8,9-dihydro-6H-[1,4]oxazino[3,4-e]purin-2-yl)pyrimidin-2-amine | 0.00357 |
| 140 | 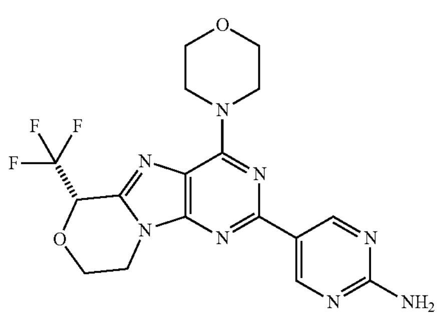 | (S)-5-(4-morpholino-6-(trifluoromethyl)-8,9-dihydro-6H-[1,4]oxazino[3,4-e]purin-2-yl)pyrimidin-2-amine | 0.00345 |
| 141 | 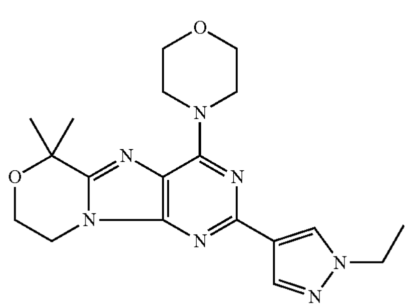 | 2-(1-ethyl-1H-pyrazol-4-yl)-6,6-dimethyl-4-morpholino-8,9-dihydro-6H-[1,4]oxazino[3,4-e]purine | >0.695 |

TABLE 1-continued

| No. | Structure | Name | IC$_{50}$, Ki (mole) PI3K, p110 alpha binding assay |
|---|---|---|---|
| 142 | 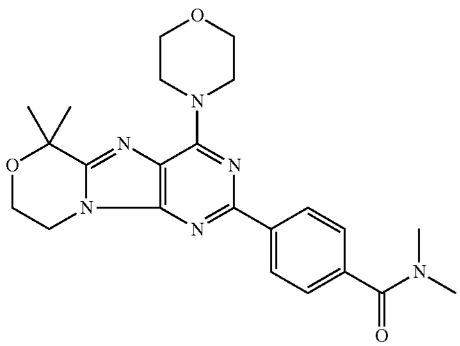 | 4-(6,6-dimethyl-4-morpholino-8,9-dihydro-6H-[1,4]oxazino[3,4-e]purin-2-yl)-N,N-dimethylbenzamide | >0.695 |
| 143 | 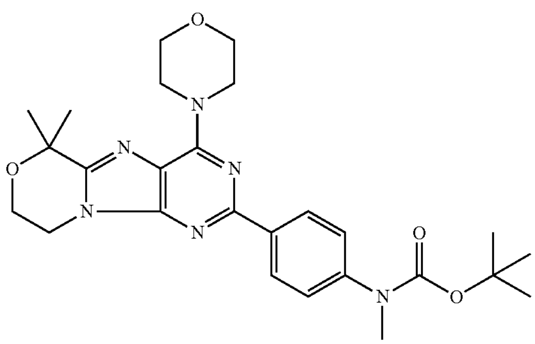 | tert-butyl 4-(6,6-dimethyl-4-morpholino-8,9-dihydro-6H-[1,4]oxazino[3,4-e]purin-2-yl)phenyl(methyl)carbamate | >0.695 |
| 144 | 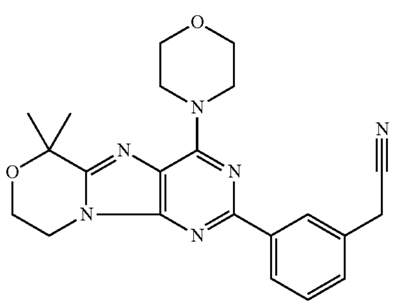 | 2-(3-(6,6-dimethyl-4-morpholino-8,9-dihydro-6H-[1,4]oxazino[3,4-e]purin-2-yl)phenyl)acetonitrile | >0.695 |
| 145 | 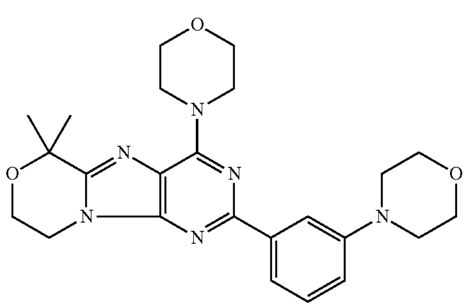 | 6,6-dimethyl-4-morpholino-2-(3-morpholinophenyl)-8,9-dihydro-6H-[1,4]oxazino[3,4-e]purine | >0.695 |

TABLE 1-continued

| No. | Structure | Name | IC$_{50}$, Ki (mole) PI3K, p110 alpha binding assay |
|---|---|---|---|
| 146 | 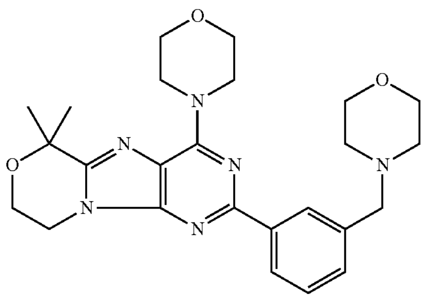 | 6,6-dimethyl-4-morpholino-2-(3-(morpholinomethyl)phenyl)-8,9-dihydro-6H-[1,4]oxazino[3,4-e]purine | >0.695 |
| 147 | 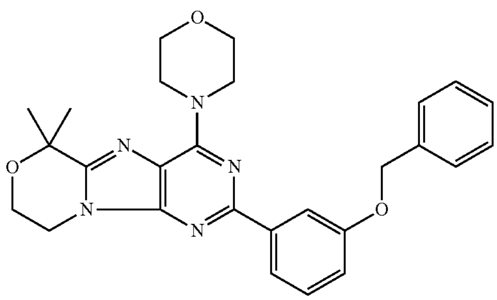 | 2-(3-(benzyloxy)phenyl)-6,6-dimethyl-4-morpholino-8,9-dihydro-6H-[1,4]oxazino[3,4-e]purine | >0.695 |
| 148 | 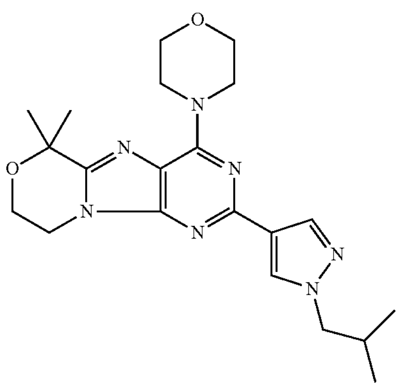 | 2-(1-isobutyl-1H-pyrazol-4-yl)-6,6-dimethyl-4-morpholino-8,9-dihydro-6H-[1,4]oxazino[3,4-e]purine | >0.695 |
| 149 | 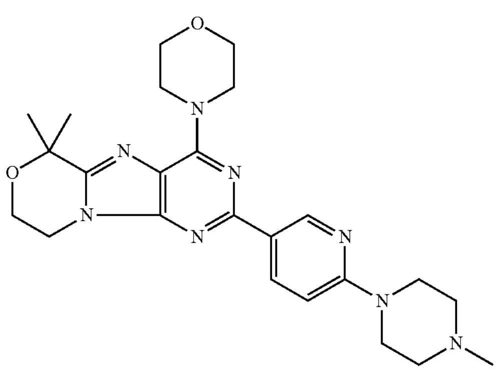 | 6,6-dimethyl-2-(6-(4-methylpiperazin-1-yl) yridine-3-yl)-4-morpholino-8,9-dihydro-6H-[1,4]oxazino[3,4-e]purine | >0.695 |

TABLE 1-continued

| No. | Structure | Name | IC$_{50}$, Ki (mole) PI3K, p110 alpha binding assay |
|---|---|---|---|
| 150 | 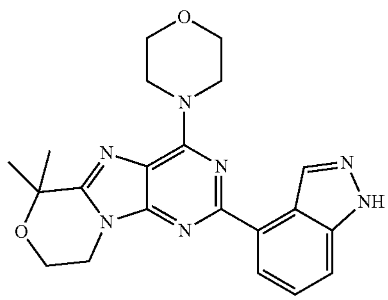 | 2-(1H-indazol-4-yl)-6,6-dimethyl-4-morpholino-8,9-dihydro-6H-[1,4]oxazino[3,4-e]purine | 0.0198 |
| 151 | 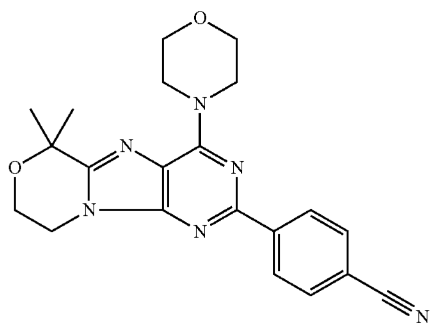 | 4-(6,6-dimethyl-4-morpholino-8,9-dihydro-6H-[1,4]oxazino[3,4-e]purin-2-yl)benzonitrile | >0.695 |
| 152 | 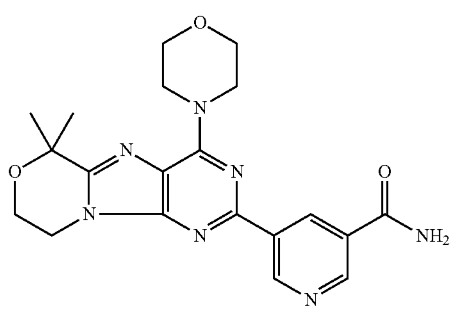 | 5-(6,6-dimethyl-4-morpholino-8,9-dihydro-6H-[1,4]oxazino[3,4-e]purin-2-yl)nicotinamide | 0.0352 |
| 153 | 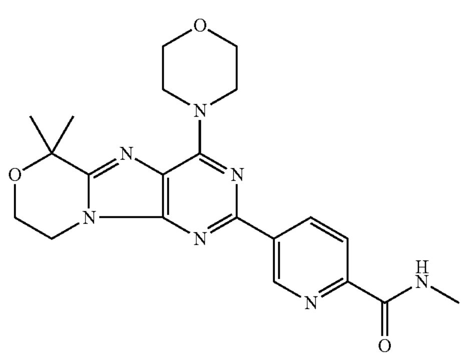 | 5-(6,6-dimethyl-4-morpholino-8,9-dihydro-6H-[1,4]oxazino[3,4-e]purin-2-yl)-N-methylpicolinamide | >0.695 |

TABLE 1-continued

| No. | Structure | Name | IC$_{50}$, Ki (mole) PI3K, p110 alpha binding assay |
|---|---|---|---|
| 154 | 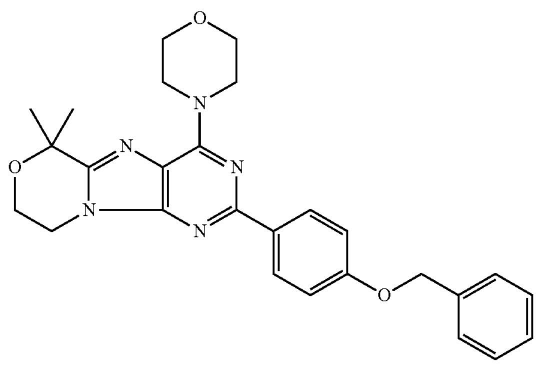 | 2-(4-(benzyloxy)phenyl)-6,6-dimethyl-4-morpholino-8,9-dihydro-6H-[1,4]oxazino[3,4-e]purine | >0.695 |
| 155 | 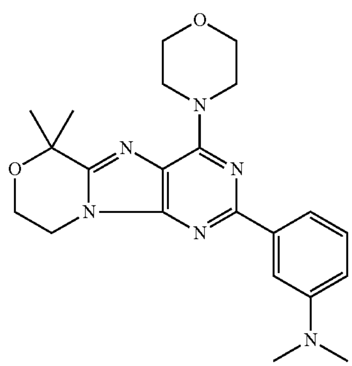 | 3-(6,6-dimethyl-4-morpholino-8,9-dihydro-6H-[1,4]oxazino[3,4-e]purin-2-yl)-N,N-dimethylaniline | >0.695 |
| 156 | 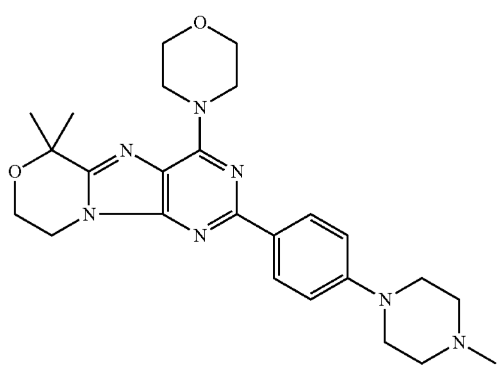 | 6,6-dimethyl-2-(4-(4-methylpiperazin-1-yl)phenyl)-4-morpholino-8,9-dihydro-6H-[1,4]oxazino[3,4-e]purine | >0.695 |
| 157 | 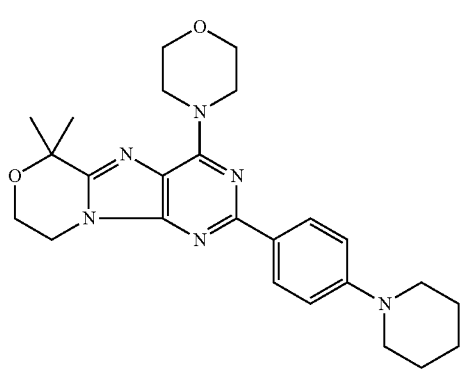 | 6,6-dimethyl-4-morpholino-2-(4-(piperidin-1-yl)phenyl)-8,9-dihydro-6H-[1,4]oxazino[3,4-e]purine | >0.695 |

TABLE 1-continued
| No. | Structure | Name | IC$_{50}$, Ki (mole) PI3K, p110 alpha binding assay |
|---|---|---|---|
| 158 | 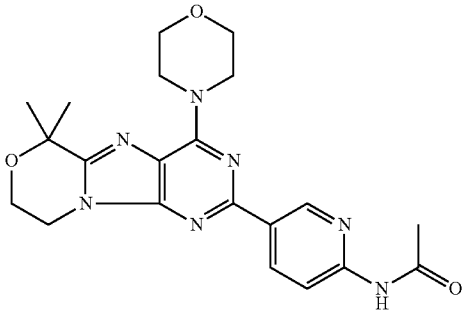 | N-(5-(6,6-dimethyl-4-morpholino-8,9-dihydro-6H-[1,4]oxazino[3,4-e]purin-2-yl)pyridine-2-yl)acetamide | 0.0490 |
| 159 | 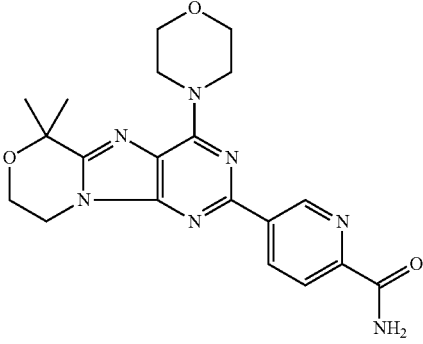 | 5-(6,6-dimethyl-4-morpholino-8,9-dihydro-6H-[1,4]oxazino[3,4-e]purin-2-yl)picolinamide | — |
| 160 | 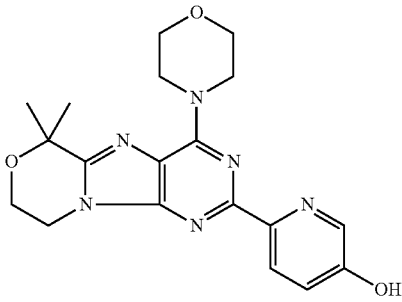 | 6-(6,6-dimethyl-4-morpholino-8,9-dihydro-6H-[1,4]oxazino[3,4-e]purin-2-yl)pyridine-3-ol | — |
| 161 | 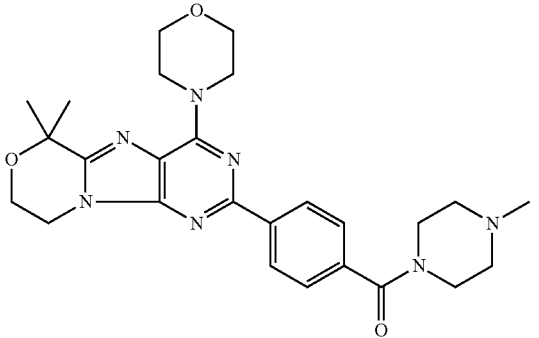 | (4-(6,6-dimethyl-4-morpholino-8,9-dihydro-6H-[1,4]oxazino[3,4-e]purin-2-yl)phenyl)(4-methylpiperazin-1-yl)methanone | >0.695 |

TABLE 1-continued

| No. | Structure | Name | IC$_{50}$, Ki (mole) PI3K, p110 alpha binding assay |
|---|---|---|---|
| 162 | 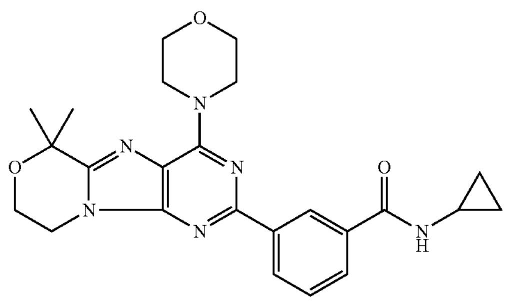 | N-cyclopropyl-3-(6,6-dimethyl-4-morpholino-8,9-dihydro-6H-[1,4]oxazino[3,4-e]purin-2-yl)benzamide | >0.695 |
| 163 | 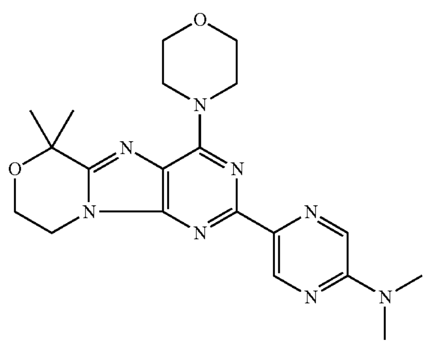 | 5-(6,6-dimethyl-4-morpholino-8,9-dihydro-6H-[1,4]oxazino[3,4-e]purin-2-yl)-N,N-dimethylpyrazin-2-amine | >0.695 |
| 164 | 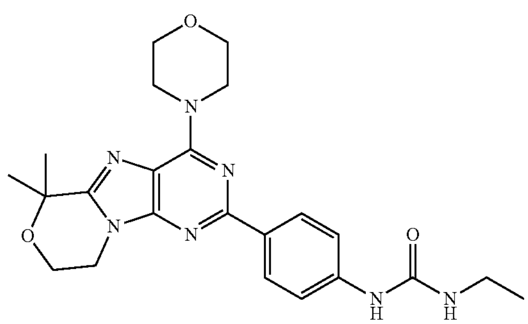 | 1-(4-(6,6-dimethyl-4-morpholino-8,9-dihydro-6H-[1,4]oxazino[3,4-e]purin-2-yl)phenyl)-3-ethylurea | 0.0417 |
| 165 | 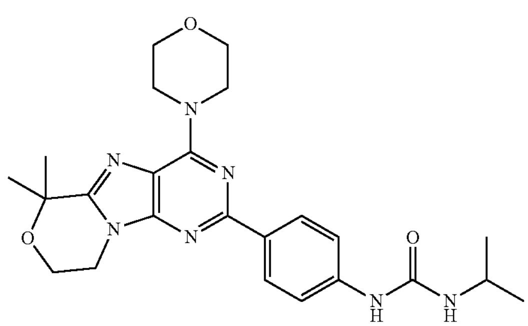 | 1-(4-(6,6-dimethyl-4-morpholino-8,9-dihydro-6H-[1,4]oxazino[3,4-e]purin-2-yl)phenyl)-3-isopropylurea | 0.337 |

TABLE 1-continued

| No. | Structure | Name | IC$_{50}$, Ki (mole) PI3K, p110 alpha binding assay |
|---|---|---|---|
| 166 | 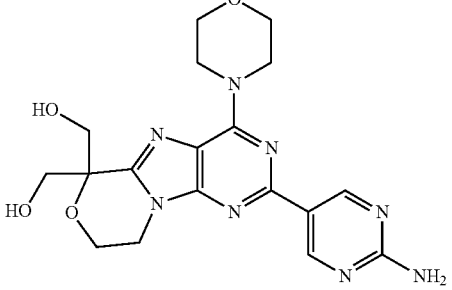 | (2-(2-aminopyrimidin-5-yl)-4-morpholino-8,9-dihydro-6H-[1,4]oxazino[3,4-e]purine-6,6-diyl)dimethanol | 0.0128 |
| 167 | 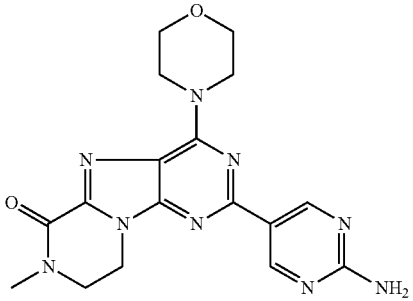 | 2-(2-aminopyrimidin-5-yl)-7-methyl-4-morpholino-8,9-dihydropyrazino[2,1-e]purin-6(7H)-one | 0.0215 |
| 168 | 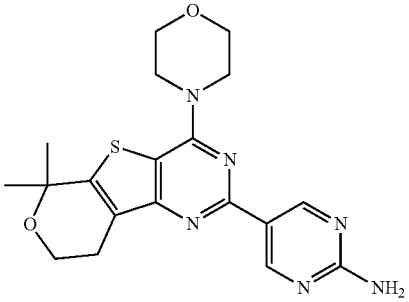 | 5-(8,8-Dimethyl-1-morpholin-4-yl-5,8-dihydro-6H-7-oxa-9-thia-2,4-diaz a-fluoren-3-yl)-pyrimidin-2-ylamine | 0.00100 |
| 169 | 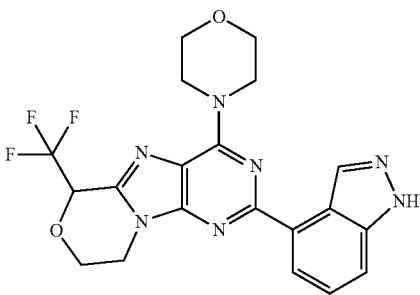 | 2-(1H-indazol-4-yl)-4-morpholino-6-(trifluoromethyl)-8,9-dihydro-6H-[1,4]oxazino[3,4-e]purine | 0.0452 |
| 170 | 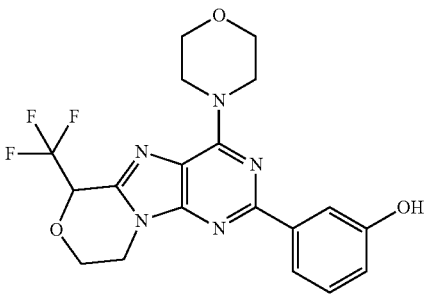 | 3-(4-morpholino-6-(trifluoromethyl)-8,9-dihydro-6H-[1,4]oxazino[3,4-e]purin-2-yl)phenol | 0.0797 |

TABLE 1-continued

| No. | Structure | Name | IC$_{50}$, Ki (mole) PI3K, p110 alpha binding assay |
|---|---|---|---|
| 171 | 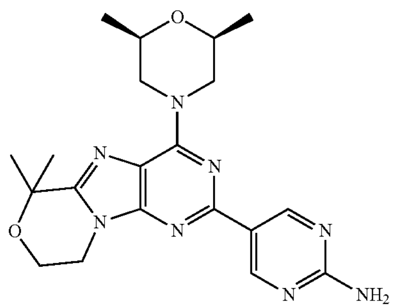 | 5-(4-((2S,6R)-2,6-dimethylmorpholino)-6,6-dimethyl-8,9-dihydro-6H-[1,4]oxazino[3,4-e]purin-2-yl)pyrimidin-2-amine | 0.01398 |
| 172 | 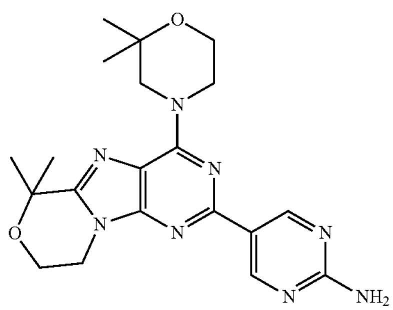 | 5-(4-(2,2-dimethylmorpholino)-6,6-dimethyl-8,9-dihydro-6H-[1,4]oxazino[3,4-e]purin-2-yl)pyrimidin-2-amine | 0.201 |
| 173 | 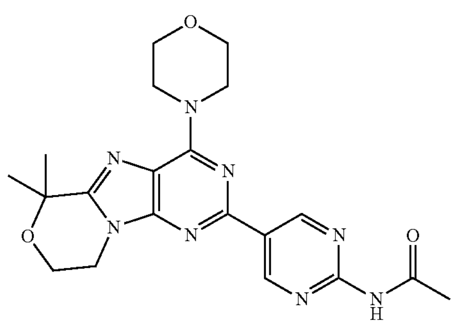 | N-(5-(6,6-dimethyl-4-morpholino-8,9-dihydro-6H-[1,4]oxazino[3,4-e]purin-2-yl)pyrimidin-2-yl)acetamide | 0.242 |
| 174 | 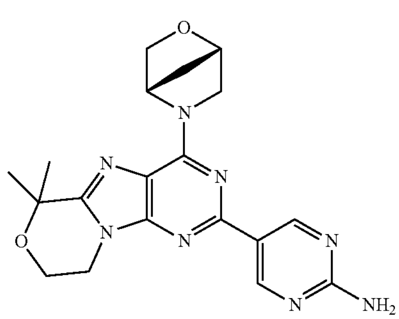 | 5-(4-((1S,4S)-2-oxa-5-azabicyclo[2.2.1]heptan-5-yl)-6,6-dimethyl-8,9-dihydro-6H-[1,4]oxazino[3,4-e]purin-2-yl)pyrimidin-2-amine | 0.394 |

TABLE 1-continued

| No. | Structure | Name | IC$_{50}$, Ki (mole) PI3K, p110 alpha binding assay |
|---|---|---|---|
| 175 | 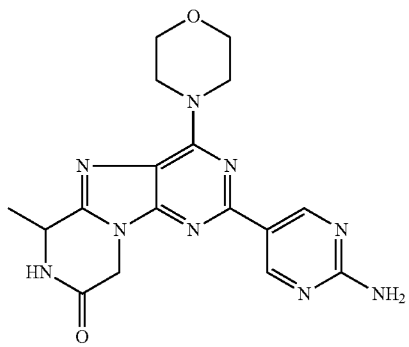 | 2-(2-aminopyrimidin-5-yl)-6-methyl-4-morpholino-6,7-dihydropyrazino[2,1-e]purin-8(9H)-one | 0.00428 |
| 176 | 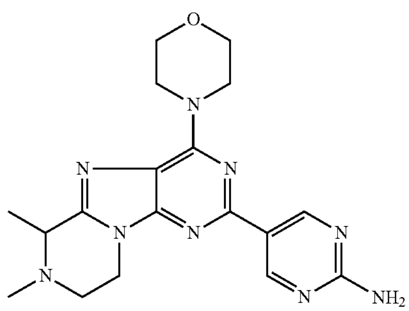 | 5-(6,7-dimethyl-4-morpholino-6,7,8,9-tetrahydropyrazino[2,1-e]purin-2-yl)pyrimidin-2-amine | 0.00689 |
| 177 | 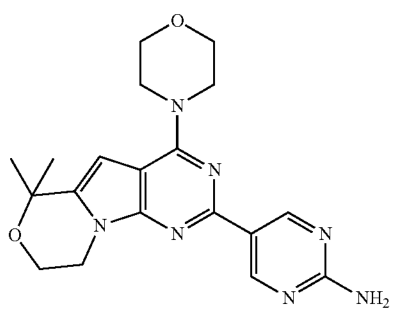 | 5-(8,8-Dimethyl-1-morpholin-4-yl-5,6-dihydro-8H-7-oxa-2,4,4b-triaza-fluoren-3-yl)-pyrimidin-2-ylamine | 0.000831 |

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with e.g. the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating hyperproliferative diseases, conditions and/or disorders including, but not limited to, those characterized by over expression of lipid kinases, e.g. PI3 kinase. Accordingly, an aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit PI3 kinase activity.

One embodiment of the invention includes a method of treating cancer in a patient comprised of administering to said patient a therapeutically effective amount of a compound of this invention wherein the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, renal, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's or leukemia. In one embodiment, the cancer is a brain cancer.

In one embodiment of the invention, the method further comprises administering to the patient an additional therapeutic agent selected from a chemotherapeutic agent, an anti-angiogenesis therapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders. In one embodiment of the invention the additional therapeutic agent is bevacizumab.

Formula I compounds may also be useful for treating hyperproliferative diseases characterized by over expression of protein kinases such as those encoded by PIM; the genes Pim-1, Pim-2, and Pim-3 (Proviral Insertion, Moloney) which are implicated in lymphoma and solid-tumor development (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Formula I compounds may be useful for treating conditions of the brain and central nervous system which require transport across the blood-brain barrier. Certain Formula I compounds have favorable penetrant properties across the blood-brain barrier for delivery to the brain. Disorders of the brain which may be effectively treated with Formula I compounds include metastatic and primary brain tumors, such as glioblastoma and melanoma.

Formula I compounds may be useful for treating ocular disorders such as wet and dry Age-related Macular Degeneration (AMD) and retina edema, by localized delivery to the eye. Certain Formula I compounds have favorable properties for delivery to, and uptake into, the eye. Certain Formula I compounds may enhance efficacy and extend duration of response for treatment of wet AMD in combination with ranibizumab (LUCENTIS®, Genentech, Inc.) and bevacizumab (AVASTIN®, Genentech, Inc.).

Another aspect of this invention provides a compound of this invention for use in the treatment of the diseases or conditions described herein in a mammal, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition.

According to this aspect of the invention there is provided a pharmaceutical composition comprising a compound of this invention in association with a pharmaceutically acceptable diluent or carrier.

One embodiment of the invention comprises a pharmaceutical composition comprised of a compound of this invention and a pharmaceutically acceptable carrier, glidant, diluent, or excipient.

One embodiment of the invention comprises a process for making a pharmaceutical composition which comprises combining a compound of this invention with a pharmaceutically acceptable carrier.

One embodiment of the invention includes a pharmaceutical composition as described above further comprising an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) may be packaged in a variety of ways depending upon the method of administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (e.g., poly(2-hydroxyethylmethacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, e.g., inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, e.g., 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. Together, the emulsifier(s) with or without stabilizer(s) make up the so-called emulsifying wax, and the wax together with an oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, about 0.5 to 10% w/w, or about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising e.g. cocoa butter or a salicylate.

Formulations suitable for intrapulmonary or nasal administration have a particle size e.g. in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, e.g. sealed ampoules and vials, and may be stored in a freeze-dried (lyophilized) condition requiring only the addition of the sterile liquid carrier, e.g. water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

One embodiment of the invention comprises a kit for treating a PI3K-mediated condition, comprising a compound of this invention, and instructions for use.

Suitable containers include, e.g., bottles, vials, syringes, blister pack, etc. The container may be formed from a variety of materials such as glass or plastic. The container may hold a compound of Formula I or a formulation thereof which is effective for treating the condition and may have a sterile access port (e.g., the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Tricyclic compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare purine compounds (Hammarstrom et al (2007) Tetrahedron Lett. 48(16):2823-2827; Cerna et al (2006) Organic Letters 8(23):5389-5392; Chang et al (2006) J. Med. Chem. 49(10): 2861-2867; Yang et al (2005) J. Comb. Chem. 7:474-482; Liu et al (2005) J. Comb. Chem. 7:627-636; Hocek et al (2004) Synthesis 17:2869-2876; Hammarstrom et al (2003) Tetrahedron Lett. 44:8361-8363; Hammarstrom et al (2002) Tetrahedron Lett. 43:8071-8073; Booth et al (1987) J. Chem. Soc, Perkin Trans. 1: Organic and Bio-Organic Chem. 7:1521-1526; Booth et al (1981) J. Chem. Soc., Chemical Communications 15:788-789; Yoneda et al (1976) J. Chem. Soc., Perkin Trans. 1: Organic and Bio-Organic Chem. 14:1547-1550; Taylor et al (1971) J. Org. Chem. 36(21): 3211-3217; Lister, J. H.; Fenn, M. D. The Purines, Supplementary 1, John Wiley & Sons, 1996, Volume 54; The Chemisty of Heterocyclic Compounds, Editors Weissberger, A.; Taylor E. C., Wiley Interscience, 1971, Volume 24; Legraverend, M.; Grierson, D. S. (2006) Bioorg. Med. Chem. 14:3987-4006; Hocek, M. (2003) Eur. J. Org. Chem. 245-254;U.S. Pat. Nos. 7,122,665; 6,743,919; 5,332,744; 4,728,644; 3,016,378; US 2008/0058297; US 2003/0139427; WO 2008/043031); and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Compounds of Formula I may be prepared singly or as compound libraries comprising at least 2, e.g. 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, the General Procedures show general methods which may be applied for preparation of Formula I compounds, as well as key intermediates. The Figures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formula I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, e.g.: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters of the racemic mixture, such as a menthyl ester, for example with (−) menthyl chloroformate, in the presence of base, or Mosher ester, α-methoxy-α-(trifluoromethyl)phenyl acetate (Jacob III. J. Org. Chem. (1982) 47:4165), and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 1996/015111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

General Procedure A Suzuki Coupling:

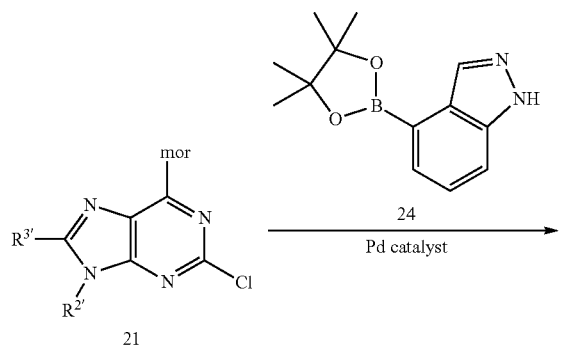

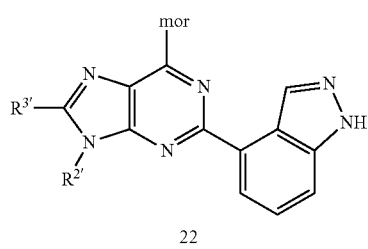

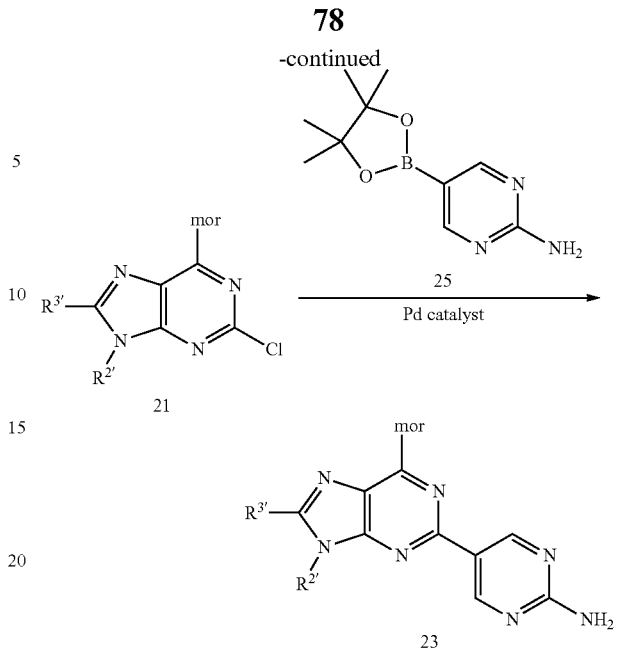

The Suzuki-type coupling reaction is useful to attach a monocyclic heteroaryl, a fused bicyclic heterocycle, a fused bicyclic heteroaryl, or a phenyl at the 2-position of the pyrimidine ring of a 2-chloro-purine 21. For example, 21 may be combined with 1.5 equivalents of 4-(4,4,5,5-tetramethyl-1,3,2-dioxaborolan-2-yl)1H-indazole 24, and dissolved in about 3 equivalents of sodium carbonate as about a 1 molar solution in water and about an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example, N-THP protected compound 41. In some cases potassium acetate was used in place of sodium carbonate to adjust the pH of the aqueous layer. The Suzuki palladium coupling reaction may be optimized and/or accelerated under microwave conditions. The reaction may be heated at about 100-150° C. under pressure in a microwave reactor such as the Biotage Optimizer (Biotage, Inc.) for about 10 to 30 minutes. The contents are cooled, concentrated, and extracted with ethyl acetate, or another organic solvent. After evaporation of the organic layer the Suzuki coupling products, 6,8,9-substituted 2-(1H-indazol-4-yl)-purine 22, or 6,8,9-substituted 2-(5-pyrimidin-2-amine)-purine 23, may be purified on silica or by reverse phase HPLC. Substituents R$^{2'}$, R$^{3'}$ may be R$^2$, R$^3$ as defined, or protected forms or precursors thereof.

A variety of palladium catalysts can be used during the Suzuki coupling step to form compounds, including exemplary embodiments 22 and 23. Suzuki coupling is a palladium mediated cross coupling reaction of an arylhalide, such as 21, with a boronic acid or ester such as 4-(4,4,5,5-tetramethyl-1,3,2-dioxaborolan-2-yl)-1H-indazole 24 or 5-(4,4,5,5-tetramethyl-1,3,2-dioxaborolan-2-yl)pyrimidin-2-amine 25. Low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(Oac)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PmePh$_2$)$_2$, Cl$_2$Pd[P(4-F-Ph)$_3$]$_2$, Cl$_2$Pd[P(C$_6$F$_6$)$_3$]$_2$, Cl$_2$Pd[P (2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30 (US 2004/0254066). One such Suzuki palladium catalyst is [1,1'-bis(diphenylphosphino)ferrocene]dichloropalladium(II), complex with dichloromethane, represented as Pd(dppf)Cl$_2$.

General Procedure B C-6 Nitrogen Substitution

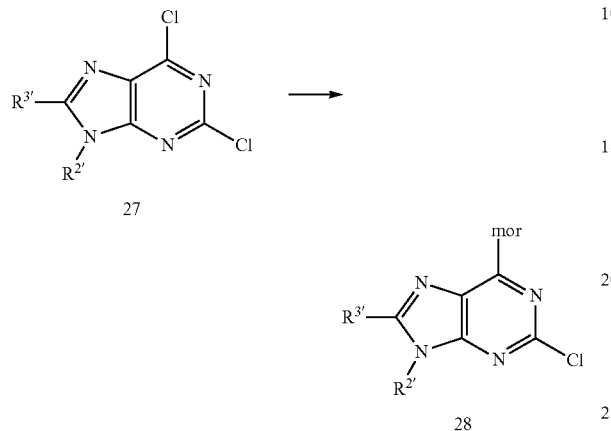

To a 2,6-dichloro purine intermediate 27 in a solvent such as ethanol is added a morpholino amine (mor, 1.1 equiv.) and a non-nucleophilic base such as triethylamine (Net$_3$, 1.5 equiv.). Alternatively, acetonitrile may be used as the solvent and potassium carbonate may be used as the base. The reaction mixture is stirred at room temperature for about 1 hour or overnight, volatiles removed in vacuo and residue partitioned between DCM and brine. If the mixture is insoluble it may be sonicated and the solid product was collected by filtration. Drying with magnesium sulfate and evaporation of the solvent gives N'-(2-chloro purin-6-yl)-amine substituted intermediate 28, often as a crystalline solid, or by trituration. Substituents R$^{2'}$ and R$^{3'}$ may be R$^2$ and R$^3$ as defined, or protected forms or precursors thereof.

General Procedure C N-9 Nitrogen Alkylation

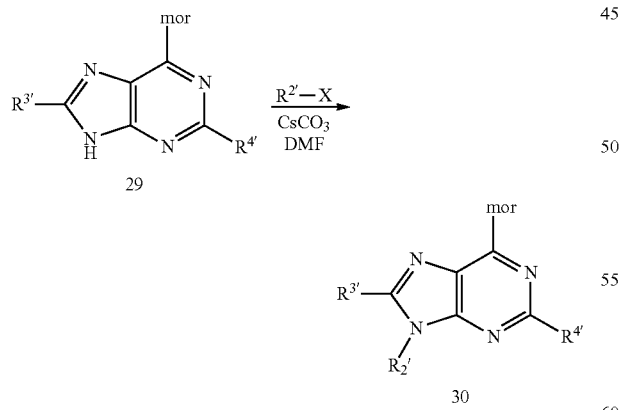

9-H Purine intermediate 29 is brought up into DMF and 2 equiv of cesium carbonate is added to the reaction mixture. The reaction is heated to 50° C. whereupon 3 equivalents of an alkyl halide R$^{2'}$—X are added to the reaction mixture. The reaction is monitored by TLC or LC/MS and stirred until completion, typically several hours. The reaction mixture is extracted with EtOAc and water, and the organic layer is dried, filtered and concentrated to get crude 9-alkylated purine 30 which is used directly in the next reaction or purified by reverse phase HPLC. Substituents R$^{2'}$, R$^{3'}$ and R$^{4'}$ may be R$^2$, R$^3$ and R$^4$ as defined, or protected forms or precursors thereof.

General Procedure D THP Deprotection

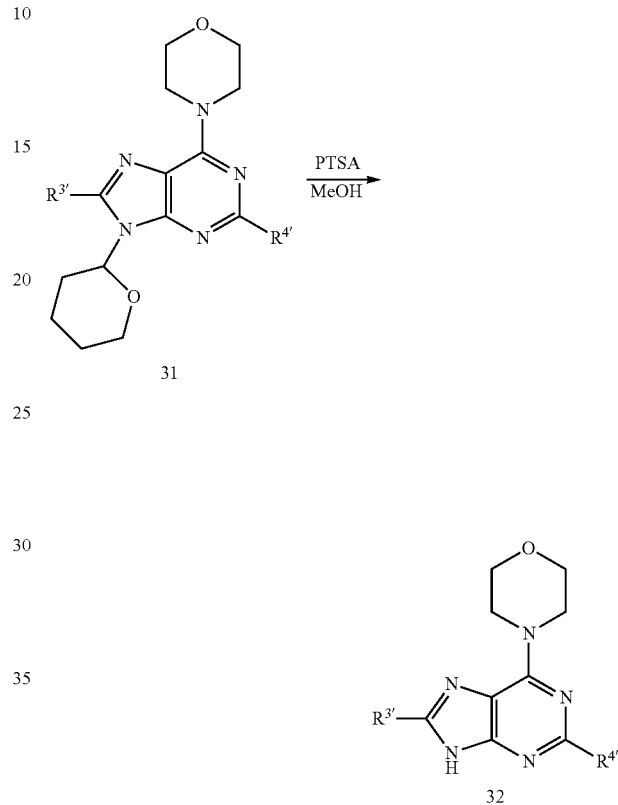

Generally, N-9-tetrahydropyranyl substituted 31 may be treated with catalytic amounts of para-toluenesulfonic acid (PTSA) in a solution of methanol and heated to about 50° C. until the tetrahydropyran (THP) group is removed to afford compound 32. The reaction may be monitored by LC-MS or TLC. Substituents R$^{3'}$ and R$^{4'}$ may be R$^3$ and R$^4$ as defined, or protected forms or precursors thereof.

General Procedure E Boc Deprotection

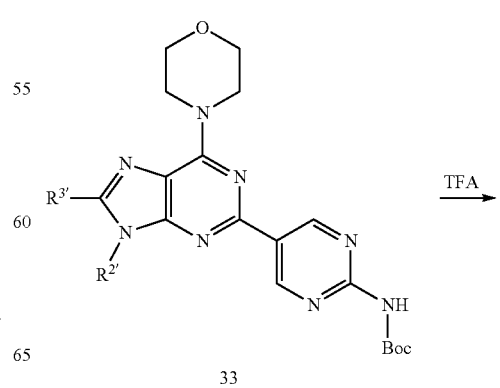

-continued

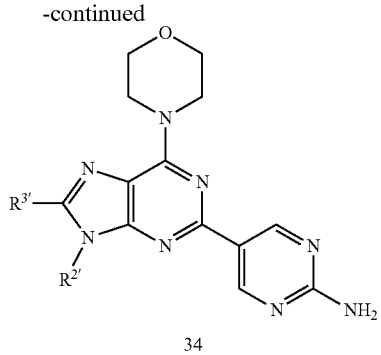
34

Generally, Boc-substituted 33 is treated with TFA or 4N HCl to remove the t-butoxycarbonyl group(s) and the reaction is monitored by LC-MS for completion. The crude product is then concentrated and purified by reverse phase HPLC to yield product 34 as a pure solid. Substituents $R^{2'}$ and $R^{3'}$ may be $R^2$ and $R^3$ as defined, or protected forms or precursors thereof.

General Procedure F Amide Coupling

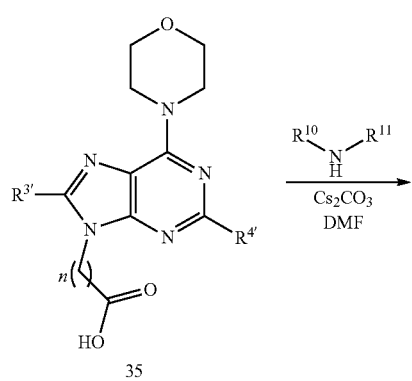
35

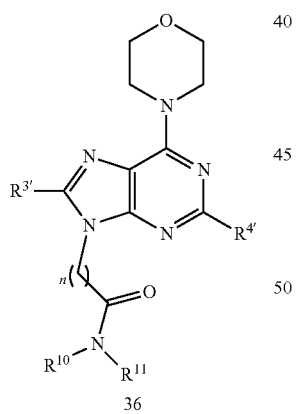
36

A 2,6,8 substituted, 9-alkylcarboxyl purine 35, where n is 1 to 3, is treated with 1.5 eq HATU (2-(7-aza-1H-benzotriazole-1-yl)-1,1,3,3-tetramethyluronium hexafluorophosphate), an excess (such as 3 eq) of an alkylamine (HNR$^{10}$R$^{11}$) and an excess (such as 3 eq) of cesium carbonate in dimethylformamide (DMF). Alternatively, other coupling reagents may be used. The reaction is stirred until complete and extracted in ethylacetate with saturated bicarbonate solution. The organic layer is dried, filtered and concentrated to yield the acylated, crude intermediate, which is purified via reverse phase HPLC to yield product 36.

Substituents $R^{3'}$ and $R^{4'}$ may be $R^3$ and $R^4$ as defined, or protected forms or precursors thereof.

General Procedure G Pyrimidooxazine (Formula In) synthesis

Scheme 1

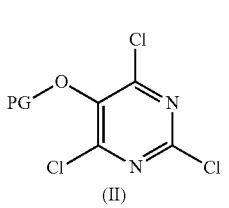
(II)

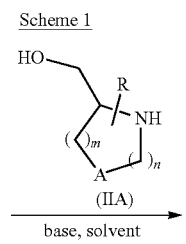
(IIA)

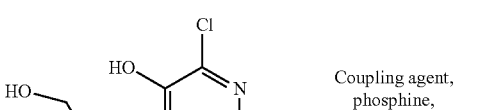
(III)

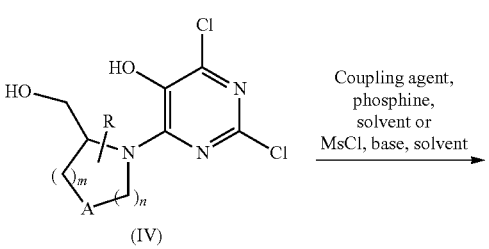
(IV)

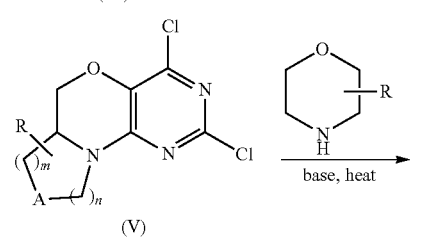
(V)

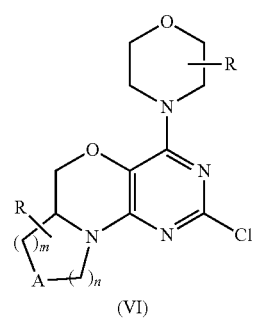
(VI)

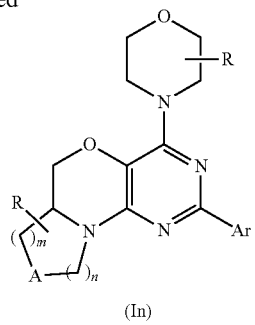

(In)

m = 1 or 2
n = 0, 1 or 2
A = CH$_2$ if n = 1 or N or O if n = 2
R = appropriate substituent
Ar = aryl, heteroaryl or heterobiaryl
PG = protection group The pyrimidooxazines of formula (In) are prepared according to the procedures described below in Scheme 1 above, or by methods known in the art. Protected trichloropyrimidines of formula (II) may be prepared using methods described in the literature. The trichlorides may be reacted with a cyclic amine of formula (IIA) in the presence of a base such as triethylamine in a solvent such as ethanol at around ambient temperature to give dichlorides of formula (III). The methoxy pyrimidine may be deprotected using a reagent such as LiCl in a solvent such as DMF under microwave irradiation for PG=Me or by treatment with an acid such as TFA in a solvent such as DCM when PG=p-methoxybenzyl to give phenols of formula (IV). Tricyclic pyrimidooxazines of formula (V) may then be formed from diols of formula (IV) with a azo compound such as DIAD in the presence of a phosphine such as triphenyl phosphine in a solvent such as 1,4-dioxane. Alternatively, formation of compounds (V) may be accomplished by firstly transforming the hydroxyl group into a suitable leaving group followed by an intramolecular substitution reaction facilitated by reaction with a reagent such as methanesulfonyl chloride in the presence of base such as triethylamine in a solvent such as THF. Compounds of formula (VI) may be prepared from compounds (V) by reaction with a morpholine derivative (incorporating appropriate substituents R) in the presence of a base such as triethylamine in a solvent such as ethanol at elevated temperature. For n=2, A=O, the addition of morpholine occurs in a regiospecific manner whereas for n=1, A=CH$_2$, this reaction may also lead to the formation of the undesired regioisomer. Pyrimidooxazines of formula (I) may be formed by reaction of compounds of formula (VI) with an aryl or heteroaryl metallated reactant such as a heteroaryl boronic acid, boronic ester or a stannane in the presence of a transition metal catalyst such as Pd(PPh$_3$)$_2$Cl$_2$ and a base such as aqueous sodium carbonate in a solvent such as acetonitrile under microwave irradiation at a temperatures of up to 150° C.

Alternatively, pyrimidooxazines of formula (In) may be prepared according to Scheme 2 below. Protected trichloro pyrimidines of formula (II) may be obtained from compounds of formula (VII) (prepared according to methods described in the art) by reaction with an alcohol such as p-methoxybenzyl alcohol in the presence of a azo compound such as DIAD in the presence of a phosphine such as triphenyl phosphine in a solvent such as 1,4-dioxane. Alternatively, formation of compounds (II) may be accomplished by treatment of compound (VII) with a silyl halide such as tert-butylchlorodiphenylsilane in the presence of a base such as triethylamine with as additive such as N,N-dimethylaminopyridine in a solvent as DMF. The trichloropyrimidines (II) may be reacted with a cyclic amine of formula (IIA) in the presence of a base such as triethylamine in a solvent such as ethanol at ambient temperature to give dichlorides of formula (VII). Compounds of formula (IX) may be prepared by reaction of compounds of formula (VIII) with an aryl or heteroaryl metallated reactant such as a heteroaryl boronic acid, boronic ester or a stannane in the presence of a transition metal catalyst such as Pd(PPh$_3$)$_2$Cl$_2$ and a base such as aqueous sodium carbonate in a solvent such as acetonitrile under microwave irradiation at a temperatures of up to 150° C. For bulky protection groups, e.g. PG=p-methoxybenzene or PG=tert-butyldiphenylsilane, this substitution may occur with regiospecific control giving 2-aryl or 2-heteroaryl compounds of formula (IX). Phenols of formula (X) may be formed by deprotection of compounds (IX) using an acid such as TFA in a solvent such as DCM at ambient temperature. Compounds of formula (X) may be converted to compounds of formula (XI) using the methods described for the conversion of compounds of formula (IV) to compounds of formula (V) in Scheme 1. Finally, pyrimidooxazines of formula (In) may formed by reaction of compounds of formula (XI) by reaction with a morpholine (incorporating appropriate substituents R) in the presence of a base such as triethylamine in a solvent such as ethanol at temperatures up to reflux.

Scheme 2

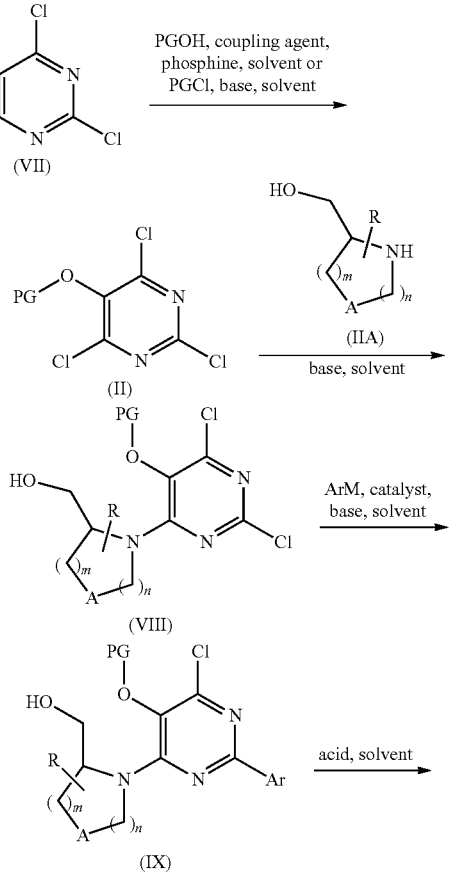

-continued

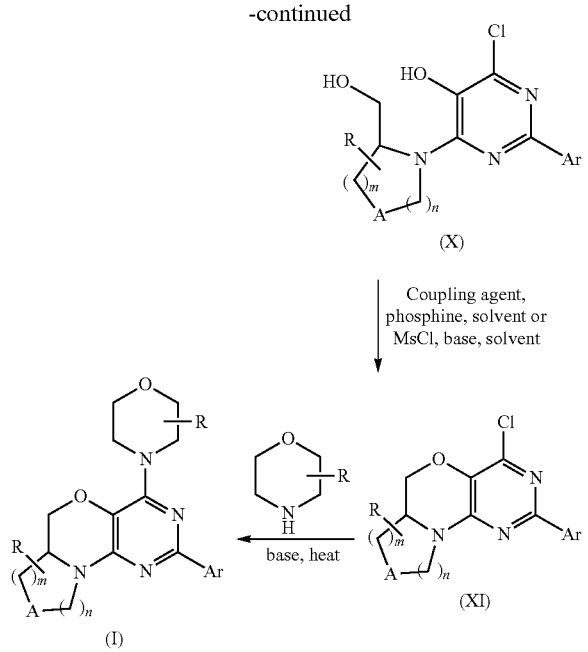

m = 1 or 2
n = 0, 1 or 2
A = CH2 if n = 1 or N or O if n = 2
R = appropriate substituent
Ar = PH or substituted aromatic ring
M = metal
PG = protection group

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in hertz (Hz).

HPLC was conducted by the following exemplary methods:

| (A) LCMS short method - 10 min run | |
|---|---|
| HPLC-Agilent 1200 | |
| Mobile phase A | Water with 0.05% TFA |
| Mobile phase B | Acetonitrile with 0.05% TFA |
| Column | Agilent ZORBAX SD-C18, 1.8 μm, 2.1 × 30 mm |
| Column temperature | 40 degree C. |
| LC gradient | 3-95% B in 8.5 min, 95% in 2.5 min |
| LC Flowrate | 400 μL/min |
| UV wavelength | 220 nm and 254 nm |
| Mass Spec - Agilent quadrupole 6140 | |
| Ionization | ESI positive |
| Scan range | 110-800 amu |
| (B) Waters Acquity/LCT long method - 20 min run | |
| Waters Acquity UPLC | |
| Mobile phase A | Waters with 0.05% TFA |
| Mobile phase B | Acetonitrile with 0.05% TFA |
| Column | Acquity UPLC BEH C18, 1.7 μm, 2.1 × 50 mm |
| Column temperature | 40 degree C. |
| LC gradient | 2-98% B in 17.0 min, 98% in 1.5 min |
| LC Flowrate | 600 μL/min |
| UV wavelength | 254 nm |
| Mass Spec - Waters LCT Premier XE | |
| Ionization | ESI positive |
| Scan range | 100-800 amu |
| (C) LCMS 2.5 min Chiral method | |
| Mobile Phase A: CO2 | |
| Mobile Phase B: methanol | |
| Isocratic conditions: 25% B | |
| Flow rate: 5 mL/min | |
| Outlet pressure: 120 Bar | |
| Temperature: 40° C. | |
| Column: ChiralCel OJ (4.6 × 50 mm, 3 μm) | |
| Uv: 230 nm | |
| System: Berger Analytical SFC/MS | |
| Chiral purification: | |
| Conditions A: | |
| Mobile Phase A: CO2 | |
| Mobile Phase B: methanol | |
| Isocratic conditions: 25% B | |
| Flow rate: 60 mL/min | |
| Outlet pressure: 100 Bar | |
| Temperature: 40 degrees C. | |
| Column: ChiralCel OJ (21.2 × 250 mm, 5 μm) | |
| Uv: 230 nm | |
| System: Berger MGII | |

Example 1

2,6-dichloro-9-methyl-9H-purine 4

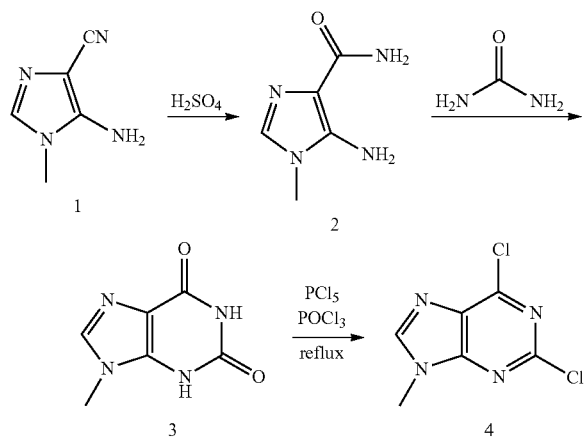

The cyano group of 5-amino-1-methyl-1H-imidazole-4-carbonitrile 1 is hydrolyzed to the amide in sulfuric acid to give 5-amino-1-methyl-1H-imidazole-4-carboxamide 2 which was cyclized with urea to 9-methyl-1H-purine-2,6 (3H,9H)-dione 3. Chlorination of 3 yields 2,6-dichloro-9-methyl-9H-purine 4.

Example 2

4-(4,4,5,5-tetramethyl-[1,3,2]dioxaborolan-2-yl)-1H-indazole 24—route 1

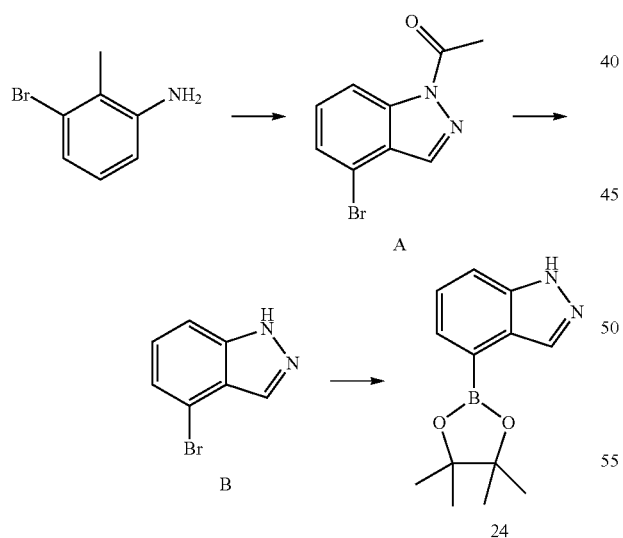

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried (MgSO$_4$). The crude product was evaporated onto silica and purified by chromatography eluting with 20% to 40% EtOAc-petrol to give 1-(4-bromo-indazol-1-yl)-ethanone A (3.14 g, 49%) as an orange solid, and 4-bromo-1H-indazole B (2.13 g, 40%) as a pale orange solid. A: $^1$H NMR (400 MHz, CDCl$_3$) 2.80 (3H, s), 7.41 (1H, t, J=7.8 Hz), 7.50 (1H, d, J=7.8 Hz), 8.15 (1H, s), 8.40 (1H, d, J=7.8 Hz). B: H NMR (400 MHz, CDCl$_3$) 7.25 (1H, t, J=7.3 Hz), 7.33 (1H, d, J=7.3 Hz), 7.46 (1H, d, J=7.3 Hz), 8.11 (1H, s), 10.20 (1H, br s).

To a solution of the 1-(4-bromo-indazol-1-yl)-ethanone A (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO$_4$). The solvent was removed by evaporation under reduced pressure to give 4-bromo-1H-indazole B (2.36 g, 93%).

To a solution of the 4-bromo-1H-indazole B (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl$_2$(dppf)$_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO$_4$). The crude material was purified by chromatography eluting with 30% to 40% EtOAc-petrol to give an inseparable 3:1 mixture of the 4-(4,4,5,5-tetramethyl-[1,3,2]dioxaborolan-2-yl)-1H-indazole 24 (369 mg, 60%) and indazole (60 mg, 20%), isolated as a yellow gum which solidified upon standing to furnish as an off-white solid. $^1$H NMR (400 MHz, d$_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s); impurity at 1.25.

Example 3

4-(4,4,5,5-Tetramethyl-[1,3,2]dioxaborolan-2-yl)-1H-indazole 24—route 2

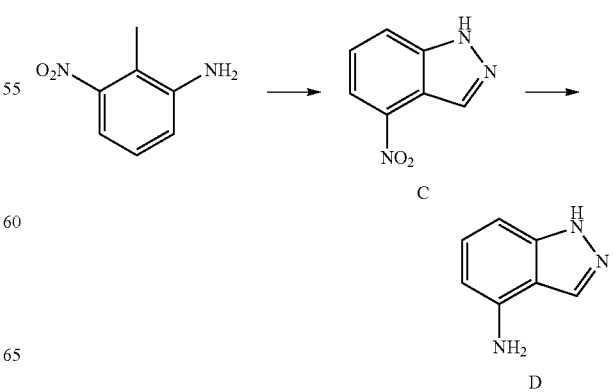

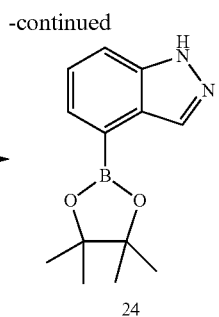

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole C (1.98 g, 81%).

A mixture of 4-nitro-1H-indazole C (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine D (631 mg, 100%).

An aqueous solution of sodium nitrite (337 mg, 4.89 mmol) in water (2 mL) was added dropwise to a suspension of 1H-indazol-4-ylamine D (631 mg, 4.74 mmol) in 6M hydrochloric acid (7.2 mL) at below 0° C. After stirring for 30 minutes, sodium tetrafluoroborate (724 mg) was added to the reaction mixture. A viscous solution resulted, which was filtered and washed briefly with water to yield 1H-indazole-4-diazonium tetrafluoroborate salt E (218 mg, 20%) as a deep red solid.

Dry methanol (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield 4-(4,4,5,5-tetramethyl-[1,3,2]dioxaborolan-2-yl)-1H-indazole 24 (117 mg).

Example 4

1-(Tetrahydro-2H-pyran-2-yl)-4-(4,4,5,5-tetramethyl-1,3,2-dioxaborolan-2-yl)-1H-indazole (Route A)

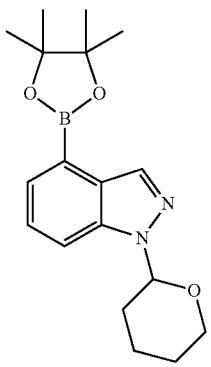

Step A: Preparation of 4-chloro-1H-indazole: To a 250 ml flask with stir bar was added 2-methyl-3-chloroaniline (8.4 ml, 9.95 g, 70.6 mmol), potassium acetate (8.3 g, 84.7 mmol) and chloroform (120 ml). This mixture was cooled to 0° C. with stirring. To the cooled mixture was added acetic anhydride (20.0 ml, 212 mmol) drop wise over 2 minutes. The reaction mixture was warmed to 25° C. and stirred for 1 hour. At this point, the reaction was heated to 60° C. Isoamyl nitrite (18.9 ml, 141 mmol) was added and the reaction was stirred overnight at 60° C. Once complete, water (75 ml) and THF (150 ml) were added and the reaction was cooled to 0° C. LiOH (20.7 g, 494 mmol) was added and the reaction was stirred at 0° C. for 3 hours. Water (200 ml) was added and the product was extracted with EtOAc (300 ml, 100 ml). The organic layers were combined, dried with $MgSO_4$ and concentrated in vacuo to yield 4-chloro-1H-indazole 11.07 g (100%) as an orange solid. $^1$H NMR (400 MHz, $CDCl_3$) δ 8.18 (d, J=1 Hz, 1H), 7.33 (d, J=8 Hz 1H), 7.31 (t, J=7 Hz, 1H), 7.17 (dd, J=7 Hz, 1 Hz 1H). LCMS (ESI pos) m/e 153 (M+1).

Step B: Preparation of 4-chloro-1-(tetrahydro-2H-pyran-2-yl)-1H-indazole: To a 1 L flask with mechanical stirrer was added 4-chloro-1H-indazole (75.0 g, 0.492 mol), pyridinium p-toluenesulfonate (1.24 g, 4.92 mmol), $CH_2Cl_2$ (500 ml) and 3,4-dihydro-2H-pyran (98.6 ml, 1.08 mol). With stirring, this mixture was heated to 45° C. for 16 hours. Analysis of reaction mixture shows production of both isomers of product. Cooled reaction to 25° C. and added $CH_2Cl_2$ (200 ml). Washed the solution with water (300 ml) and saturated $NaHCO_3$ (250 ml). Dried the organics with $MgSO_4$ and concentrated to dryness. Purified the crude product by dissolving in EtOAc/hexanes (4:6, 1 L) and adding $SiO_2$ (1.2 L). The mixture was filtered and the cake was washed with EtOAc/Hexanes (4:6, 2 L). The organics were concentrated in vacuo to yield 4-chloro-1-(tetrahydro-2H-pyran-2-yl)-1H-indazole 110.2 g (95%) as an orange solid. Isomer 1: $^1$H NMR (400 MHz, $CDCl_3$) δ 8.10 (d, J=1 Hz, 1H), 7.50 (dd, J=9 Hz, 1 Hz 1H), 7.29 (dd, J=9 Hz, 8 Hz 1H), 7.15 (dd, J=8 Hz, 1 Hz 1H) 5.71 (dd, J=9 Hz, 3 Hz 1H) 4.02 (m, 1H) 3.55 (m, 1H) 2.51 (m, 1H) 2.02 (m, 2H) 1.55 (m, 3H). LCMS (ESI pos) m/e 237 (M+1); Isomer 2: $^1$H NMR (400 MHz, $CDCl_3$) δ 8.25 (d, J=1 Hz, 1H), 7.62 (dd, J=9 Hz, 1 Hz 1H), 7.20 (dd, J=9 Hz, 8 Hz 1H), 7.06 (dd, J=8 Hz, 1 Hz 1H) 5.69 (dd, J=9 Hz, 3 Hz 1H) 4.15 (m, 1H) 3.80 (m, 1H) 2.22 (m, 2H) 2.05 (m, 1H) 1.75 (m, 3H). LCMS (ESI pos) m/e 237 (M+1).

Step C: Preparation of 1-(tetrahydro-2H-pyran-2-yl)-4-(4,4,5,5-tetramethyl-1,3,2-dioxaborolan-2-yl)-1H-indazole: To a 500 ml flask with stir bar was added 4-chloro-1-(tetrahydro-2H-pyran-2-yl)-1H-indazole (10.0 g, 42.2 mmol), DMSO (176 ml), $PdCl_2(PPh_3)_2$ (6.2 g, 8.86 mmol), tricyclohexylphosphine (0.47 g, 1.69 mmol), bis(pinacolato)diboron (16.1 g, 63.4 mmol) and potassium acetate (12.4 g, 0.127 mol). With stirring, the mixture was heated to 130° C. for 16 hours. The reaction was cooled to 25° C. and EtOAc (600 ml) was added and washed with water (2×250 ml). The organics were dried with $MgSO_4$ and concentrated in vacuo to dryness. The crude product was purified by $SiO_2$ plug (120 g), eluting with 10% EtOAc/Hexanes (1 L) and 30% EtOAc/Hexanes (1 L). The filtrate was concentrated in vacuo to give 13.9 g (100%) of 1-(Tetrahydro-2H-pyran-2-yl)-4-(4,4,5,5-tetramethyl-1,3,2-dioxaborolan-2-yl)-1H-indazole as a 20% (wt/wt) solution in ethyl acetate. $^1$H NMR shows the presence of about 20% (wt/wt) bis(pinacolato) diboron. $^1$H NMR (400 MHz, $CDCl_3$) δ 8.37 (s, 1H), 7.62 (dd, J=14 Hz, 2 Hz 1H), 7.60 (dd, J=7 Hz, 1 Hz 1H), 7.31 (dd, J=8 Hz, 7 Hz 1H) 5.65 (dd, J=9 Hz, 3 Hz 1H) 4.05 (m, 1H) 3.75 (m, 1H) 2.59 (m, 1H) 2.15 (m, 1H) 2.05 (m, 1H) 1.75 (m, 3H) 1.34 (s, 12H). LCMS (ESI pos) m/e 245 (M+1).

Example 5

1-(Tetrahydro-2H-pyran-2-yl)-4-(4,4,5,5-tetramethyl-1,3,2 dioxaborolan-2-yl)-1H-indazole (Route B)

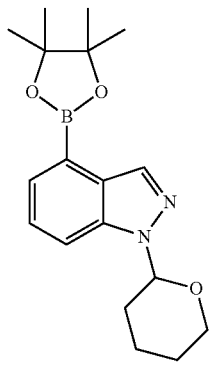

Step A: Preparation of 4-nitro-1H-indazole: A mixture of 2-methyl-3-nitro aniline (200 g, 1.315 moles), acetic acid (8000 ml) was cooled to 15-20° C. and a solution of sodium nitrite (90.6 g, 1.315 moles) in water (200 ml) was slowly added over 30 min. After the addition, the reaction temp. was increased to 25-30° C. and the reaction was stirred at this temp for 2-3 h. Reaction progress was monitored by TLC and after completion of reaction product was filtered and residue was washed with acetic acid (1000 ml). Acetic acid was distilled under vacuum (550 mm of Hg) below 80° C. and water (8000 ml) was added, cooled to 25-30° C. and stirred for 30 min. The slurry was filtered and washed with water (1000 ml). Crude product was dried under heating at 70-80° C. for 2 hours, then was taken in 5% ethyl acetate/n-hexane (100:2000 ml) solution and stirred for 1-1.5 h at ambient temperature. The suspension was filtered and washed with 5% ethyl acetate/n-hexane mixture (25:475 ml). The product obtained was dried under vacuum at below 80° C. for 10-12 h to give 4-nitro-1H-indazole as a brown solid (150 g, 70%): mp: 200-203° C.; $^1$H NMR (200 MHz, CDCl$_3$) δ 13.4 (br, 1H), 8.6 (s, 1H), 8.2-7.95 (dd, 2H), 7.4 (m, 1H). ESMS m/z 164 (M+1). Purity: 95% (HPLC)

Step B: Preparation of 4-amino-1H-indazole: A mixture of 4-nitro-1H-indazole (200 g, 1.22 moles) and 10% palladium on carbon (20.0 g) in EtOH (3000 ml) was hydrogenated at ambient temperature (reaction was exothermic and temperature increased to 50° C.). After completion of reaction, the catalyst was removed by filtration. The solvent was evaporated under vacuum at below 80° C. and cooled to room temperature and n-hexane (1000 ml) was added to the residue and stirred for 30 min. Isolated solid was filtered and washed with n-hexane (200 ml). Product was dried under vacuum at 70-80° C. for 10-12 h to give 4-amino-1H-indazole as a brown solid (114 g, 70%), m. p.: 136-143° C. $^1$H NMR (200 MHz, CDCl$_3$) δ 12 (br, 1H), 8.0 (s, 1H), 7.1-7.0 (dd, 2H), 6.5 (d, 1H), 3.9 (m, 2H). ESMS m/z 134 (M+1). Purity: 90-95% (HPLC)

Step C: Preparation of 4-iodo-1H-indazole: A mixture of 4-amino-1H-indazole (50.0 g, 0.375 moles) in water (100 ml) and con. hydrochloric acid (182 ml) was cooled to −10° C. To this a solution of sodium nitrite (51.7 g, 0.75 moles) in water (75 ml) was added drop wise at −10° C. in about 30-60 min. (during addition frothing was observed). In another flask a mixture of potassium iodide (311 g, 1.87 moles) in water (3000 ml) was prepared at room temperature and to this above cooled diazonium salt at 30-40° C. was added in about 30-40 min. The reaction was maintained at 30° C. for 1 h and after completion of reaction, ethyl acetate (500 ml) was added and the reaction mixture was filtered through Celite. The layers were separated and the aq. layer was extracted with ethyl acetate (2×500 ml). The combined organic layers were washed with 5% hypo solution (2×500 ml), brine (500 ml), dried (Na$_2$SO$_4$) and concentrated. Crude product was purified by chromatography (silica gel, hexane, 15-20% ethyl acetate/hexane) to furnish 4-iodo-1H-indazole as an orange solid (23.0 g, 25%). mp: 151-177 C: $^1$H NMR (200 MHz, CDCl$_3$) δ 12.4 (br, 1H), 8.0 (s, 1H), 7.6 (dd, 2H), 7.1 (d, 1H). ESMS m/z 245 (M+1). Purity: 95-98% (HPLC).

Step D: Preparation of 4-iodo-1-(2-tetrahydropyranyl) indazole: A mixture of 4-amino-1H-indazole (250.0 g, 1.024 moles), 3,4-dihydro-2H-pyran (126.0 g, 1.5 moles) and PPTS (2.57 g, 0.01 moles) in CH$_2$Cl$_2$ (1250 ml) was heated to 50° C. for 2 h. The reaction was cooled to room temperature and poured into water (625 ml), the layers were separated, and aqueous layer was extracted with CH$_2$Cl$_2$ (250 ml). The combined organic layers were washed with water (625 ml), dried (Na$_2$SO$_4$) and concentrated. Crude residue was purified by chromatography (silica gel, hexane, 5-10% ethyl acetate/hexane) to furnish 4-iodo-1-(2-tetrahydropyranyl) indazole as an oil (807.0 g, 60%). $^1$H NMR (200 MHz, CDCl$_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H). ESMS m/z 329 (M+1).

Step E: Preparation of 1-(tetrahydro-2H-pyran-2-yl)-4-(4,4,5,5-tetramethyl-1,3,2-dioxaborolan-2-yl)-1H-indazole: A mixture of 4-iodo-1-(2-tetrahydropyranyl) indazole (100 g, 0.304 moles), bispinacalotodiborane (96.4 g, 0.381 moles), PdCl$_2$ (dppf) (8.91 g, 0.012 moles) and potassium acetate (85.97 g, 0.905 moles) in DMSO (500 ml) were heated to 80° C. for 2-3 h. After completion, reaction was cooled to room temperature and water (1500 ml) was added. Reaction mass was extracted into ethyl acetate (3×200 ml) and combined organic layers were evaporated, dried (Na$_2$SO$_4$) and concentrated. Crude product was purified by column chromatography (silica gel, hexane, 5-10% ethyl acetate/hexane) to obtain 1-(Tetrahydro-2H-pyran-2-yl)-4-(4,4,5,5-tetramethyl-1,3,2-dioxaborolan-2-yl)-1H-indazole as viscous brown oil (70.0 g, 70%). $^1$H NMR (CDCl$_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H) 1.4-1.2 (s, 12H). ESMS m/z 329 (M+1)

Example 6

4-methyl-5-(4,4,5,5-tetramethyl(1,3,2-dioxaborolan-2-yl)) pyrimidine-2-ylamine

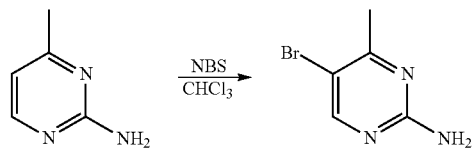

To a solution of 4-methylpyrimidine-2-ylamine (8.0 g, 0.073 mol) in chloroform (320 mL) was added N-bromosuccinimide (13.7 g, 0.077 mol). The reaction mixture was stirred in the dark for 18 hrs. LC/MS indicated the reaction was completed. The mixture was diluted with DCM, then washed with 1N NaOH aq solution and brine, dried over MgSO₄, filtered and concentrated to yield 5-bromo-4-methylpyrimidine-2-ylamin (12 g, Yield: 86%).

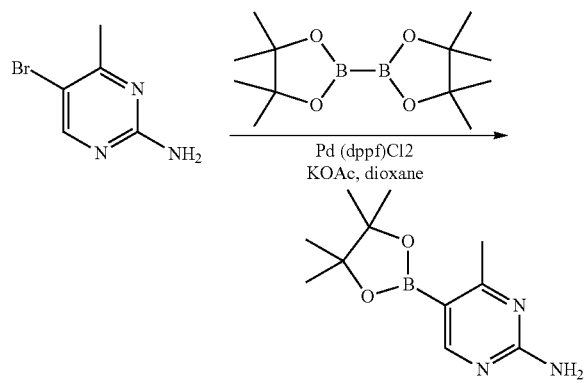

A mixture of 5-bromo-4-methylpyrimidine-2-ylamine (5.0 g, 26 mmol), potassium acetate (7.83 g, 79.8 mmol), 4,4,5,5-tetramethyl-2-(4,4,5,5-tetramethyl-1,3,2-dioxaborolan-2-yl)-1,3,2-dioxaborolane (7.43 g, 29.2 mmol) in dioxane (140 mL) was stirred for 20 min under nitrogen. 1,1'-bis(diphenylphosphino) ferrocene palladium (II) chloride dichloromethane adduct (1.08 g, 1.33 mmol) was added to the reaction mixture. The reaction mixture was heated to 115° C. for 18 h under nitrogen. Upon completion, the mixture was cooled and EtOAc was added. The resulting mixture was sonicated and filtered. Additional EtOAc was used to wash the solid. The combined organic extracts were washed with water, dried over MgSO₄, filtered and concentrated. The crude was purified by chromatography eluting with 20~100% EtOAc/hexane to yield 4.5 g of 4-methyl-5-(4,4,5,5-tetramethyl(1,3,2-dioxaborolan-2-yl))pyrimidine-2-ylamine (yield: 74%). ¹H-NMR (DMSO, 400 MHz): δ 8.28 (s, 1H), 6.86 (br s, 2H), 2.35 (s, 3 H), 1.25 (s, 12 H). MS (ESI) m/e (M+H⁺) 236.15, 154.07.

Example 7

2,4,6-Trichloro-5-hydroxy-pyrimidine

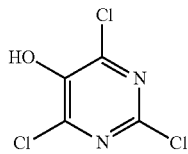

Step 1: 6-Hydroxy-5-methoxy-1H-pyrimidine-2,4-dione, sodium salt

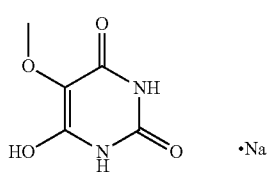

Under an atmosphere of nitrogen sodium metal (1.15 g, 0.05 moles) was added portionwise to ethanol (dried over 4 Å molecular sieves, 50 mL) at 40° C. and the mixture stirred until a solution was formed. Urea (3.0 g, 0.05 moles) was added and the mixture heated at 100° C. for 15 minutes until complete dissolution was achieved. The reaction mixture was allowed to cool slightly and methoxymethylmalonate (8.1 g, 0.05 moles) added, a pink/white precipitate forming almost immediately. Further dry ethanol (10 mL) was added to maintain a stirrable mixture. The resultant suspension was heated at 100° C. (reflux) for 4 hours. The reaction mixture was concentrated in vacuo and the residue dried under high vacuum to give 6-Hydroxy-5-methoxy-1H-pyrimidine-2,4-dione, sodium salt as a pink/white solid used in the subsequent step without analysis or purification.

Step 2: 2,4,6-Trichloro-5-methoxy-pyrimidine

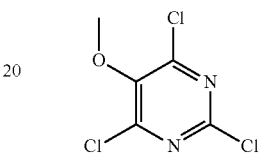

6-Hydroxy-5-methoxy-1H-pyrimidine-2,4-dione, sodium salt (21 mmol) was suspended in phosphorous oxychloride (20 mL) and the mixture dived between two 20 mL microwave reaction vials. The reaction mixtures were heated at 130-140° C. (~10-12 bar) for 30 minutes using microwave irradiation (CARE! SIGNIFICANT PRESSURE INCREASE!) The cooled reaction mixtures were combined and poured onto warm (approximately 40° C.) water (CARE!) and the resultant mixture extracted twice with ethyl acetate, the combined organic extracts were dried (Na₂SO₄), filtered and concentrated in vacuo to give 2,4,6-Trichloro-5-methoxy-pyrimidine as a crystalline yellow/brown solid (3.75 g, 84%). ¹H NMR (CDCl₃): 3.98 (3H, s).

Step 3: Under an atmosphere of nitrogen a solution of 2,4,6-trichloro-5-methoxy-pyrimidine (4.0 g, 18.7 mmol) in DCM (200 mL) was cooled to 0° C. and treated with boron tribromide (neat, 6.6 mL, 65 mmol) dropwise. After stirring for 18 hours at room temperature LCMS analysis indicated complete reaction. The reaction mixture was cooled and diluted with methanol (25 mL, CARE, EXOTHERM!) and the reaction mixture diluted with water (200 mL). The aqueous layer was washed with DCM and the combined organic extracts dried (Na₂SO₄) filtered and concentrated in vacuo to give 2,4,6-trichloro-5-hydroxy-pyrimidine as a pale tan solid (2.55 g, 71%). ¹³C NMR (DMSO-d₆): 149.23 (C), 145.25 (C), 145.08 (C). LCMS: R$_T$=2.65/2.77 [M–H]⁻= 197/199.

Example 101

1-[4-(3a,8-dimethyl-7-morpholin-4-yl-3,3a,8,8a-tetrahydro-2h-1-oxa-4,6,8-triaza-cyclopenta[a]inden-5-yl)-phenyl]-3-ethyl-urea 101

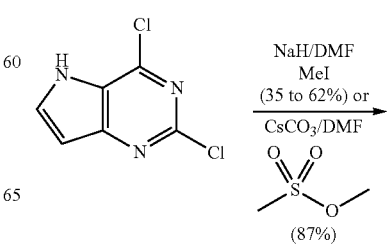

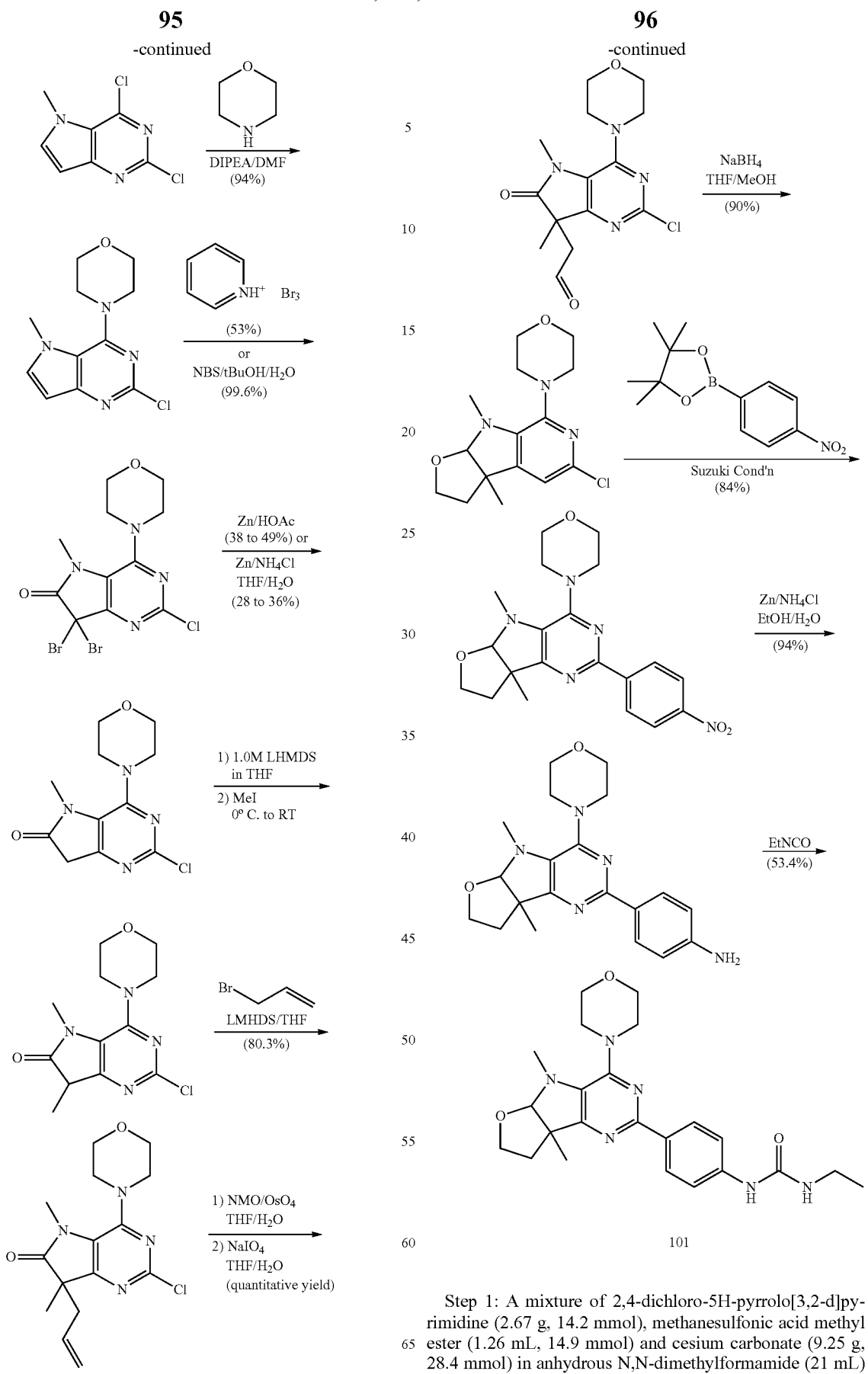
Step 1: A mixture of 2,4-dichloro-5H-pyrrolo[3,2-d]pyrimidine (2.67 g, 14.2 mmol), methanesulfonic acid methyl ester (1.26 mL, 14.9 mmol) and cesium carbonate (9.25 g, 28.4 mmol) in anhydrous N,N-dimethylformamide (21 mL) was stirred at RT (room temperature) under $N_2$ for 15 h. The reaction mixture was diluted with ethyl acetate, and the organic layer was washed with 1:1 water/brine (3×) and brine (1×), dried over Na$_2$SO$_4$, filtered, and concentrated in vacuo. The crude product was purified by silica gel chromatography to give 2.50 g (87.1%) of 2,4-dichloro-5-methyl-5H-pyrrolo[3,2-d]pyrimidine as a white solid. MS(ESI) m/z: 202.2/204.1 [M+1]$^+$.

Step 2: A mixture of 2,4-dichloro-5-methyl-5H-pyrrolo[3,2-d]pyrimidine (1.25 g, 6.19 mmol), morpholine (1.08 mL, 12.37 mmol), and N,N-diisopropylethylamine (2.37 mL, 13.61 mmol) in N,N-dimethylformamide (36 mL) was stirred at RT under N$_2$ for 15 h. The reaction mixture was diluted with 1:1 diethyl ether/ethyl acetate, and the organic layer was washed with 1:1 water/brine (3×) and brine (1×), dried over Na$_2$SO$_4$, filtered, and concentrated in vacuo. The crude product was purified by silica gel chromatography to give 1.47 g (94.0%) of 4-(2-chloro-5-methyl-5H-pyrrolo[3,2-d]pyrimidin-4-yl)morpholine as a white solid. MS(ESI) m/z: 253.1/255.1 [M+1]$^+$.

Step 3 To a stirred mixture of 4-(2-chloro-5-methyl-5H-pyrrolo[3,2-d]pyrimidin-4-yl)morpholine (1.46 g, 5.78 mmol) in tert-butyl alcohol (50 mL) and water (20 mL) at RT was added NBS (3.08 g, 17.33 mmol). The reaction mixture was stirred at 30° C. for 18 h. The reaction mixture was diluted with ethyl acetate, and the organic layer was washed with water and brine, dried over Na$_2$SO$_4$, filtered, and concentrated in vacuo. The crude product was purified by silica gel chromatography to give 2.45 g (99.4%) of 7,7-dibromo-2-chloro-5-methyl-4-morpholino-5H-pyrrolo[3,2-d]pyrimidin-6(7H)-one as a solid. MS(ESI) m/z: 427 [M+1]$^+$.

Step 4: To 7,7-dibromo-2-chloro-5-methyl-4-morpholino-5H-pyrrolo[3,2-d]pyrimidin-6(7H)-one (1.70 g, 3.99 mmol) in 2M aqueous ammonium chloride solution (9.96 mL, 19.9 mmol) and THF (40 mL) at 0° C. was added zinc dust (573.4 mg, 8.775 mmol). The reaction mixture was stirred at RT for 30 min and then diluted with DCM (40 mL). The reaction mixture was filtered through a pad of Celite. The layers were separated, and the organic layer was washed with saturated aqueous NaHCO$_3$ solution, water, and brine, dried over Na$_2$SO$_4$, filtered, and concentrated in vacuo. The crude product was purified by silica gel chromatography to give 679 mg (63.4%) of 2-chloro-5-methyl-4-morpholino-5H-pyrrolo[3,2-d]pyrimidin-6(7H)-one a solid. MS(ESI) m/z: 269.2 [M+1]$^+$.

Step 5: To 2-chloro-5-methyl-4-morpholino-5H-pyrrolo[3,2-d]pyrimidin-6(7H)-one (466.0 mg, 1.73 mmol) in anhydrous THF (25 mL) under N$_2$ at −78° C. was added dropwise 1.0 M lithium hexamethyldisilazide in THF (3.8 mL, 3.8 mmol). The reaction mixture was stirred at −78° C. under N$_2$ for 60 minutes. Methyl iodide (0.32 mL, 5.20 mmol) was then added, and the reaction mixture was stirred at ambient temperature for 18 h. The reaction mixture was quenched with saturated aqueous NH$_4$Cl solution and diluted with ethyl acetate. The organic layer was washed with water and brine, dried over Na$_2$SO$_4$, filtered, and concentrated in vacuo. Purification by silica gel chromatography eluted with 20 to 100% ethyl acetate/heptane yielded two compounds: 2-chloro-5,7,7-trimethyl-4-morpholino-5H-pyrrolo[3,2-d]pyrimidin-6(7H)-one (169.0 mg, 32.8%) as the first eluant; MS(ESI) m/z: 297.0 [M+1]$^+$, and 2-chloro-5,7-dimethyl-4-morpholino-5H-pyrrolo[3,2-d]pyrimidin-6(7H)-one as second eluant (63.8 mg, 13.0%); MS(ESI) m/z: 283.2 [M+1]$^+$.

Step 6: To 2-chloro-5,7-dimethyl-4-morpholino-5H-pyrrolo[3,2-d]pyrimidin-6(7H)-one (92.0 mg, 0.32 mmol) in anhydrous THF (5 mL) under N$_2$ at −78° C. was added dropwise 1.0 M lithium hexamethyldisilazide in THF (0.65 mL, 0.65 mmol). The reaction mixture was stirred at −78° C. under N$_2$ for 60 minutes. Allyl bromide (0.062 mL, 0.72 mmol) dissolved in 0.5 mL of THF was added, and the reaction mixture was stirred at ambient temperature for 16 h. The reaction mixture was quenched with saturated aqueous NH$_4$Cl solution and diluted with ethyl acetate. The organic layer was washed with water and brine, dried over Na$_2$SO$_4$, filtered, and concentrated in vacuo. Purification by silica gel chromatography eluted with 10 to 100% ethyl acetate/heptane gave 84.3 mg (80.3%) of 7-allyl-2-chloro-5,7-dimethyl-4-morpholino-5H-pyrrolo[3,2-d]pyrimidin-6(7H)-one. MS(ESI) m/z: 323.1 [M+1]$^+$.

Step 7: To a stirred solution of 7-allyl-2-chloro-5,7-dimethyl-4-morpholino-5H-pyrrolo[3,2-d]pyrimidin-6(7H)-one (80.0 mg, 0.25 mmol) in anhydrous THF (3.0 m) and water (1.0 mL) cooled to 0° C. was added N-methylmorpholine N-oxide (34.8 mg, 0.29 mmol), followed by 2.5% osmium tetraoxide in tert-butanol. (0.033 mL, 0.025 mmol). The reaction mixture was stirred at ambient temperature under N$_2$ for 16 h. Sodium sulfite (312.4 mg, 2.48 mmol) was then added, and the reaction mixture was stirred at RT for 20 min. The reaction mixture was diluted with water and then extracted with ethyl acetate (2×). The combined organic layers were dried over Na$_2$SO$_4$, filtered, and concentrated in vacuo. The crude intermediate was then diluted with anhydrous THF (3.0 mL) and water (1.0). Sodium periodate (79.5 mg, 0.372 mmol) was added, and the reaction mixture was sonicated for 1 minute and then stirred at RT for 2 days. The reaction mixture was diluted with ethyl acetate, and the organic layer was washed with water and brine, dried over Na$_2$SO$_4$, filtered, and concentrated in vacuo to give 80.4 mg (99%) of 2-(2-chloro-5,7-dimethyl-4-morpholino-6-oxo-6,7-dihydro-5H-pyrrolo[3,2-d]pyrimidin-7-yl)acetaldehyde. MS(ESI) m/z: 325.1 [M+1]$^+$.

Step 8: To a stirred solution of 2-(2-chloro-5,7-dimethyl-4-morpholino-6-oxo-6,7-dihydro-5H-pyrrolo[3,2-d]pyrimidin-7-yl)acetaldehyde (80.4 mg, 0.248 mmol) in THF (3.7 mL) and methanol (0.25 mL) at 0° C. was added sodium borohydride (20.6 mg, 0.55 mmol) in one portion. The reaction mixture was stirred at ambient temperature under N$_2$ for 5 h and then diluted with ethyl acetate. The organic layer was washed with water and brine, dried over Na$_2$SO$_4$, filtered, and concentrated in vacuo. Purification by silica gel chromatography eluted with 15 to 100% ethyl acetate/heptane gave 76 mg (99%) of 4-(2-chloro-5-methyl-{3a,6-dimethylhexahydro-2H-furo[2,3-b]pyrrolo}[3,2-d]pyrimidin-4-yl)morpholine. MS(ESI) m/z: 311.2 [M+1]$^+$.

Step 9: In a microwave vial was placed 4-(2-chloro-5-methyl-{3a,6-dimethylhexahydro-2H-furo[2,3-b]pyrrolo}[3,2-d]pyrimidin-4-yl)morpholine (70.0 mg, 0.225 mmol), 4-nitrophenylboronic acid pinacol ester (70.1 mg, 0.281 mmol), tetrakis(triphenylphosphine)palladium(0) (18.2 mg, 0.016 mmol), sodium carbonate (41.1 mg, 0.38 mmol), and potassium carbonate (49.8 mg, 0.36 mmol). Degassed acetonitrile (3.5 mL) and degassed water (1.0) were added. The reaction mixture was subjected to microwave irradiation at 120° C. for 15 minutes. The cooled reaction was diluted with ethyl acetate, and the reaction mixture was filtered through a pad of Celite to rid excess Pd. The organic layer was washed with water and brine, dried over Na$_2$SO$_4$, filtered, and concentrated in vacuo. Purification by silica gel chromatography eluted with 10 to 100% ethyl acetate/heptane gave 75.3 mg (84.1%) of 4-(5-methyl-2-(4-nitrophenyl)-{3a,6-dimethylhexahydro-2H-furo[2,3-b]pyrrolo}[3,2-d]pyrimidin-4-yl)morpholine. MS(ESI) m/z: 398.3 [M+1]$^+$.

Step 10: To a stirred solution of 4-(5-methyl-2-(4-nitrophenyl)-{3a,6-dimethylhexahydro-2H-furo[2,3-b]pyrrolo}[3,2-d]pyrimidin-4-yl)morpholine (78.0 mg, 0.196 mmol) dissolved in ethanol (4.7 mL) and water (3.1 mL) was added ammonium chloride (210 mg, 3.93 mmol) followed by iron (54.8 mg, 0.982 mmol). The reaction mixture was stirred at 95° C. for 2 h and then diluted with 10% MeOH/DCM and saturated aqueous NaHCO$_3$ solution. The reaction mixture was sonicated and then filtered through a pad of Celite to rid iron. The filtrate was extracted with DCM (3×), and the combined organic layers were washed with brine, dried over Na$_2$SO$_4$, filtered, and concentrated in vacuo to obtain 68.0 mg (94.2%) of 4-(5-methyl-4-morpholino-{3a,6-dimethyl-hexahydro-2H-furo[2,3-b]pyrrolo}[3,2-d]pyrimidin-2-yl)aniline as a white foam. MS(ESI) m/z: 368.2 [M+1]$^+$.

Step 11: To a stirred solution of 4-(5-methyl-4-morpholino-{3a,6-dimethylhexahydro-2H-furo[2,3-b]pyrrolo}[3,2-d]pyrimidin-2-yl)aniline (17.4 mg, 0.047 mmol) in anhydrous 1,2-dichloroethane (1.4 mL) was added ethyl isocyanate (0.037 mL, 0.47 mmol), and the reaction mixture was stirred at 50° C. under N$_2$ for 2 h. The reaction was quenched with MeOH (1 mL). Volatile solvent was removed under reduced pressure, and the crude was purified by HPLC to give 11.50 mg (55.4%) of 101 as fluffy white solid. $^1$H NMR (400 MHz, DMSO) δ 8.57 (s, 1H), 8.14 (d, J=8.8 Hz, 2H), 7.45 (d, J=8.8 Hz, 2H), 6.12 (t, J=5.6 Hz, 1H), 4.98 (s, 1H), 3.87 (t, J=7.0 Hz, 1H), 3.84-3.66 (m, 4H), 3.60-3.48 (m, 2H), 3.43-3.36 (m, 1H), 3.34-3.28 (m, 2H), 3.16-3.06 (m, 2H), 2.81 (s, 3H), 2.15 (dd, J=12.2, 3.4 Hz, 1H), 2.03-1.88 (m, 1H), 1.47 (s, 3H), 1.06 (t, J=7.2 Hz, 3H). MS(ESI) m/z: 439.2 [M+1]$^+$.

Example 102

5-(6,6-dimethyl-4-morpholino-8,9-dihydro-6h-[1,4] oxazino[3,4-e]purin-2-yl)-4-methylpyrimidin-2-amine 102

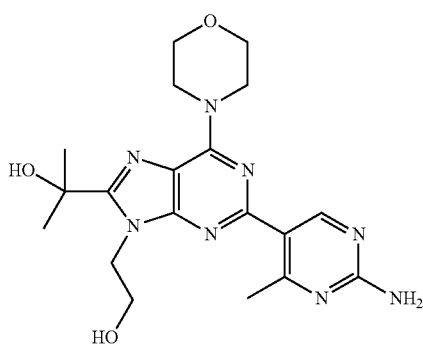

A mixture of 2-(2-(2-amino-4-methylpyrimidin-5-yl)-9-(2-hydroxyethyl)-6-morpholino-9H-purin-8-yl)propan-2-ol (550 mg, 1.3 mmol) and TFA (0.36 mL, 4.7 mmol) in toluene (9 mL) was heated at 110° C. and stirred 4 h. The reaction mixture was cooled to room temperature and concentrated in vacuo. Analytical LC-MS indicated conversion to the cyclic product as well as the elimination by-product, 2-(2-(2-amino-4-methylpyrimidin-5-yl)-6-morpholino-8-(prop-1-en-2-yl)-9H-purin-9-yl)ethanol. The crude residue was dissolved in DMF (1 mL) and purified by preparative rp-HPLC. This process provided 302 mg (57% yield) of 102.

MS (ESI+): m/z 397.4 (M+H$^+$). $^1$H NMR (400 MHz, DMSO) δ 8.79 (s, 1H), 6.78 (s, 2H), 4.20 (s, 4H), 4.12 (s, 4H), 3.74 (s, 5H), 2.63 (s, 4H), 1.58 (s, 7H)

Example 103

5-(6,6-dimethyl-4-morpholino-8,9-dihydro-6h-[1,4] oxazino[3,4-e]purin-2-yl)pyrimidin-2-amine 103

Step 1: 2-(2-chloro-6-morpholino-9-(tetrahydro-2H-pyran-2-yl)-9H-purin-8-yl)propan-2-ol

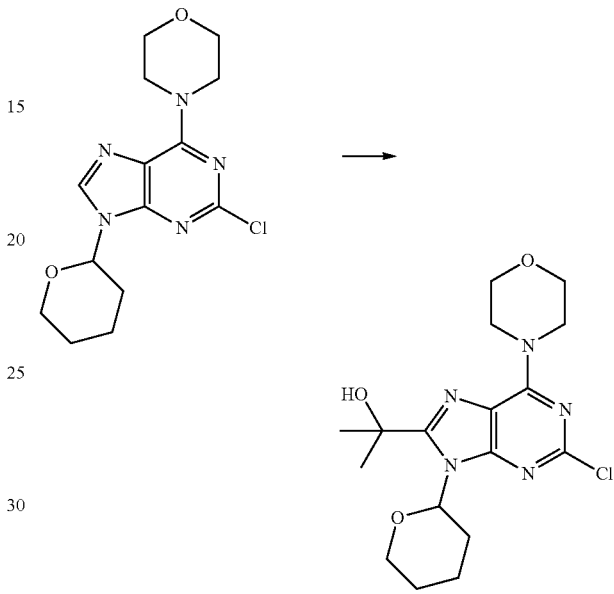

4-(2-chloro-9-(tetrahydro-2H-pyran-2-yl)-9H-purin-6-yl)morpholine (20.0 g, 0.062 mol) was cooled to −42° C. in THF (400 mL). A solution of n-butyllithium (2.5 M in hexanes, 48 mL, 0.12 mol) was added portionwise over 10 min. The mixture gradually turned yellow. The reaction mixture was then allowed to stir at −42° C. for 30 minutes and then anhydrous acetone (10 mL, 0.1 mol) was added at once. The resulting reaction mixture was slowly warmed to 0° C. over a 2 hour period. The mixture was subsequently quenched with water, extracted with EtOAc and dried over MgSO$_4$. The slurry was filtered and concentrated in vacuo to provide 2-(2-chloro-6-morpholino-9-(tetrahydro-2H-pyran-2-yl)-9H-purin-8-yl)propan-2-ol (23 g, 98%) as a yellow solid. MS (ESI+): m/z 382.1 (M+H$^+$)2-(2-chloro-6-morpholino-9-(tetrahydro-2H-pyran-2-yl)-9H-purin-8-yl)propan-2-ol Step 2: 2-chloro-6,6-dimethyl-4-morpholino-8,9-dihydro-6H-[1,4]oxazino[3,4-e]purine

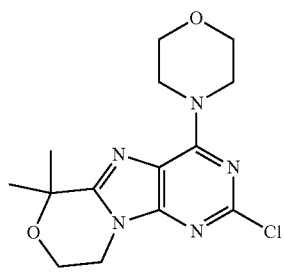

2-(2-chloro-6-morpholino-9-(tetrahydro-2H-pyran-2-yl)-9H-purin-8-yl)propan-2-ol (23 g, 0.06 mol) was suspended in MeOH (270 mL) and a catalytic amount of p-toluenesulfonic acid monohydrate (1.22 g, 7.1 mmol) was added. The reaction mixture was heated to 50° C. and stirred for 16 h. The solution became homogenous with extended heating. LC-MS indicated complete conversion to the THP-deprotected product. The reaction mixture was concentrated to completely remove MeOH and the resultant solid was subsequently diluted with water and EtOAc. The phases were partitioned and the aqueous was extracted three times with EtOAc, dried over $MgSO_4$, filtered and concentrated. Crude 2-(2-chloro-6-morpholino-9H-purin-8-yl)propan-2-ol (ca. 15.0 g, 50.4 mmol) was treated with 1,2-dibromoethane (8.7 mL, 100 mmol) and cesium carbonate (41.0 g, 126 mmol) in DMF (200 mL). The reaction mixture was heated at 90° C. for 1.5 h. LC-MS indicated complete conversion to the cyclic product with ~10% of E2 elimination product present. The reaction mixture was cooled to room temperature and poured into a separatory funnel containing 1 N HCl and EtOAc (50:50). The aqueous layer was extracted several times with EtOAc and the combined organic portions were washed once with water. Subsequent drying over $MgSO_4$ was followed by filtration and concentration to yield a crude oily residue. This material was loaded onto a 300-g ISCO column and purified by slow gradient flash column chromatography (15-30% EtOAc in heptane). Fractions containing the desired product were concentrated and dried down under high vacuum pressure for an overnight period to give 14.3 g (88% yield) of 2-chloro-6,6-dimethyl-4-morpholino-8,9-dihydro-6H-[1,4]oxazino[3,4-e]purine. MS (ESI+): m/z 324.2 (M+H$^+$). $^1$H NMR (400 MHz, DMSO) δ 4.07 (m, 8H), 3.72 (m, 4H), 1.57 (s, 6H)

Step 3: 2-Chloro-6,6-dimethyl-4-morpholino-8,9-dihydro-6H-[1,4]oxazino[3,4-e]purine (180 mg, 0.56 mmol) in 1,2-dimethoxyethane (5.1 mL) was added 5-(4,4,5,5-tetramethyl-1,3,2-dioxaborolan-2-yl)pyrimidin-2-amine (180 mg, 0.83 mmol) and 1.0 M of cesium carbonate in water (1.7 mL). The reaction mixture was degassed for 5 min and recycled with nitrogen atmosphere. Subsequently, 1,1'-bis(diphenylphosphino)ferrocenepalladium(II) chloride (54 mg, 0.067 mmol) was added, and the mixture was degassed and recycled again. The reaction vial was then subjected to microwave irradiation for 20 mins at 140° C. Solid precipitate that formed during the reaction was filtered and rinsed with excess water. The precipitate was taken up in DCM and purified by FCC (40 g, 0.5-4% MeOH in DCM, slow gradient) to isolate 103 as a tan powder (56 mg, 27% yield). MS (ESI+): m/z 383.1 (M+H$^+$). $^1$H NMR (400 MHz, DMSO) δ 9.09 (s, 2H), 7.00 (s, 2H), 4.23 (m, 4H), 4.13 (m, 4H), 3.79-3.68 (m, 4H), 2.50 (s, 6H)

Example 104

5-(6,6-dimethyl-4-morpholino-8,9-dihydro-6h-[1,4]oxazino[3,4-e]purin-2-yl)-4-(trifluoromethyl)pyridyl-2-amine 104

2-Chloro-6,6-dimethyl-4-morpholino-8,9-dihydro-6H-[1,4]oxazino[3,4-e]purine (180 mg, 0.56 mmol) and 5-(4,4,5,5-tetramethyl-1,3,2-dioxaborolan-2-yl)-4-(trifluoromethyl)romoace-2-amine (240 mg, 0.83 mmol) were reacted under microwave Suzuki palladium conditions to give 104 (204 mg, 70% yield). LC/MS (ESI+): m/z 450 (M+H). $^1$H NMR (400 MHz, DMSO) δ 8.47 (s, 1H), 6.82 (s, 1H), 6.70 (s, 2H), 4.19 (s, 4H), 4.11 (s, 4H), 3.71 (s, 4H), 1.59 (s, 6H)

Example 105

5-(4-morpholino-8,9-dihydro-7h-[1,3]oxazino[2,3-e]purin-2-yl)pyrimidin-2-amine 105

Step 1: 4-(2-chloro-8-iodo-9-(tetrahydro-2H-pyran-2-yl)-9H-purin-6-yl)morpholine

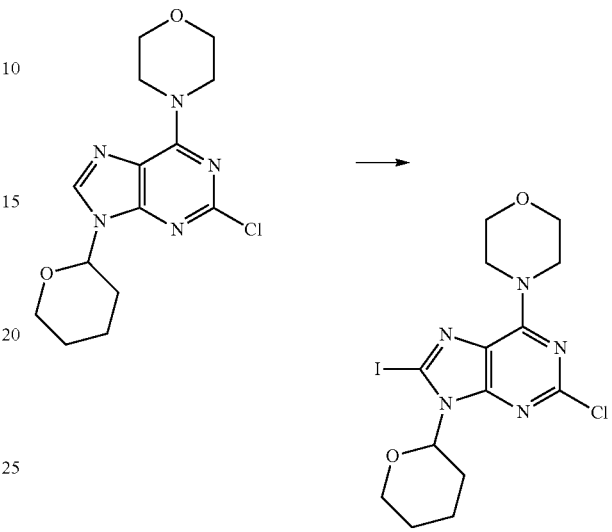

To a solution of 4-(2-chloro-9-(tetrahydro-2H-pyran-2-yl)-9H-purin-6-yl)morpholine (1.0 g, 3.1 mmol) and N,N,N',N'-tetramethylenediamine (0.7 mL, 4.6 mmol) in anhydrous THF (23 mL) at −42° C. was added 2.5 M n-butyllithium solution in hexane (4.3 mL, 11.0 mmol) dropwise down the side of the reaction flask. The reaction was stirred at cold temperature and maintained for 1 h before 1-chloro-2-iodoethane (1.4 mL, 15 mmol) was introduced. Stirring was continued for 1.5 h period. LC-MS indicated the reaction had reached complete conversion to the desired product. The reaction mixture was subsequently quenched and worked up with sat. $NH_4Cl$ aqueous solution which was extracted with EtOAc (3 times), dried over $MgSO_4$, filtered and concentrated in vacuo to give 4-(2-chloro-8-iodo-9-(tetrahydro-2H-pyran-2-yl)-9H-purin-6-yl)morpholine (1.4 g, 84% yield) determined by LC-MS to be >90% purity. MS (ESI+): m/z 450.1 (M+H$^+$)

Step 2: 4-(2-chloro-8-iodo-9-(3-(tetrahydro-2H-pyran-2-yloxy)propyl)-9H-purin-6-yl)morpholine

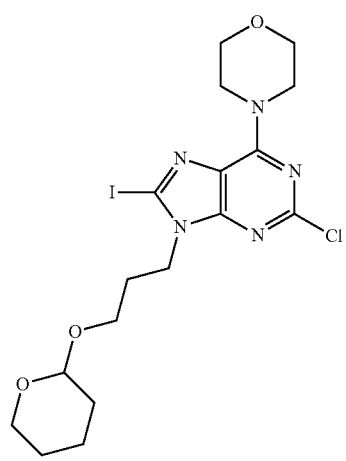

To a suspension of 4-(2-chloro-8-iodo-9-(tetrahydro-2H-pyran-2-yl)-9H-purin-6-yl)morpholine (0.655 g, 1.46 mmol) in methanol (6 mL) was added a catalytic amount of p-toluenesulfonic acid (25 mg, 0.14 mmol). The reaction mixture was heated at 50° C. for an overnight period. After this time, the mixture was cooled to room temperature and the volume of methanol was reduced by vacuum evaporation. The resulting residue was diluted with sat. aqueous NaHCO$_3$ solution. The precipitate that formed was collected by filtration. In total, 295 mg (56%) of 4-(2-chloro-8-iodo-9H-purin-6-yl)morpholine was obtained as a white solid which was dissolved in anhydrous DMF (2.5 mL). Cesium carbonate (0.53 g, 1.61 mmol) was added and the mixture was stirred together 10 min at 23° C. Subsequently 1-(2H-3,4,5,6-tetrahydropyran-2-yloxy)-3-bromopropane (0.54 g, 2.42 mmol) was introduced to the mixture. The resulting reaction mixture was heated at 50° C. for 2 h. Complete conversion was observed at the end of this period. The reaction was worked up by dilution with 1 N HCl and EtOAc. The phases were separated and the aqueous layer was extracted twice with EtOAc. The combined organic portions were dried over MgSO$_4$, filtered and concentrated in vacuo. The residue was purified by FCC (40 g silica gel column, 0-50% EtOAc in heptane) to give 385 mg (94% yield) of 4-(2-chloro-8-iodo-9-(3-(tetrahydro-2H-pyran-2-yloxy)propyl)-9H-purin-6-yl)morpholine as a pale yellow solid. MS (ESI+): m/z 508.0 (M+H$^+$)

Step 3: 2-chloro-4-morpholino-8,9-dihydro-7H-[1,3]oxazino[2,3-e]purine

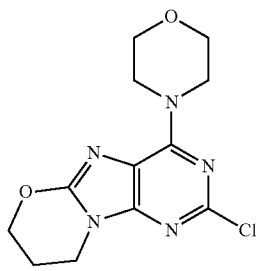

To 4-(2-chloro-8-iodo-9-(3-(tetrahydro-2H-pyran-2-yloxy)propyl)-9H-purin-6-yl)morpholine (0.39 g, 0.8 mmol) in methanol (5 mL) was added p-toluenesulfonic acid (10 mg, 0.08 mmol). The reaction was heated at 50° C. for 30 min, whereupon precipitation was observed signaling reaction completion. This was confirmed by analytical LC-MS. The reaction mixture was concentrated in vacuo to give 3-(2-chloro-8-iodo-6-morpholino-9H-purin-9-yl)propan-1-ol. Copper(I) iodide (9 mg, 0.05 mmol), picolinic acid (10 mg, 0.09 mmol) and potassium phosphate (0.4 g, 1.9 mmol) were combined in oven-dried 50-mL round-bottom flask and evacuated/recycled with N$_2$ atmosphere. Subsequently, 3-(2-chloro-8-iodo-6-morpholino-9H-purin-9-yl)propan-1-ol was dissolved in anhydrous dimethyl sulfoxide (6.7 mL) and introduced via syringe. The entire mixture was heated at 80° C. for 20 h. LC-MS indicated good conversion to the desired product. The reaction mixture was cooled to room temperature, diluted with water and EtOAc, dried over MgSO4, filtered and concentrated in vacuo. The residue was purified by FCC (40 g silica gel column, 0-100% EtOAc in heptane) to give 112 mg of 2-chloro-4-morpholino-8,9-dihydro-7H-[1,3]oxazino[2,3-e]purine (40%). MS (ESI+): m/z 296.2 (M+H$^+$)

Step 4: 2-chloro-4-morpholino-8,9-dihydro-7H-[1,3]oxazino[2,3-e]purine (112 mg, 0.38 mmol), 5-(4,4,5,5-tetramethyl-1,3,2-dioxaborolan-2-yl)pyrimidin-2-amine 25 (0.1 g, 0.454 mmol), 1 M cesium carbonate in water (0.8 mL, 0.8 mmol) and acetonitrile (0.8 mL) were placed in a 10-mL CEM microwave reaction vial and capped. The flask was slowly evacuated under vacuum and replaced with a nitrogen atmosphere. Tetrakis(triphenylphosphine)palladium(0) (43.8 mg, 0.038 mmol) was introduced and the evacuation/N$_2$ cycle was repeated. The reaction mixture was irradiated in the microwave at 140° C. for 20 min. LC-MS indicated complete conversion. The mixture was filtered through a short plug of Celite® eluting with EtOAc and subsequently concentrated in vacuo. The residue was purified by rp-HPLC to provide 105 (62.3 mg, 46% yield). MS (ESI+): m/z 355.1 (M+H$^+$)

Example 106

5-(4-morpholino-6,7,8,9-tetrahydropyrido[2,1-e]purin-2-yl)pyrimidin-2-amine 106

Step 1: 4-(8-(4-bromobutyl)-2-chloro-9-(tetrahydro-2H-pyran-2-yl)-9H-purin-6-yl)morpholine

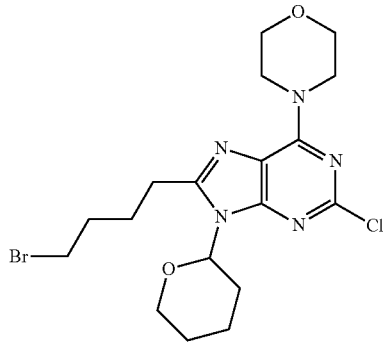

A solution of 4-(2-chloro-9-(tetrahydro-2H-pyran-2-yl)-9H-purin-6-yl)morpholine (Example 118) (5.0 g, 15 mmol) and N,N,N',N'-tetramethylethylenediamine (3.5 mL, 23 mmol) in THF (110 mL) was cooled to −42° C. and treated with a solution of 2.5M n-Butyllithium in hexane (22 mL, 54 mmol) drop-wise over 5 minutes. After 30 minutes at −42° C., 1,4-dibromo-butane (8.9 mL, 75 mmol) was added and the reaction mixture was slowly warmed to 0° C. over 1 hr and then warmed to ambient temperature for 90 minutes. The mixture was quenched with a saturated solution of NH$_4$Cl, and diluted with ethyl acetate. The aqueous layer was extracted into ethyl acetate (3×), and the combined organics were dried over sodium sulfate, filtered, and absorbed onto celite for purification by flash chromatography to afford 4-(8-(4-bromobutyl)-2-chloro-9-(tetrahydro-2H-pyran-2-yl)-9H-purin-6-yl)morpholine as a white solid (1.1 g, 15%). LC/MS (ESI+): m/z 459 (M+H)

Step 2: 4-(8-(4-bromobutyl)-2-chloro-9H-purin-6-yl)morpholine

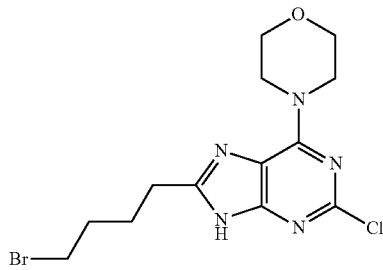

A suspension of 4-(8-(4-bromobutyl)-2-chloro-9-(tetrahydro-2H-pyran-2-yl)-9H-purin-6-yl)morpholine (1.1 g, 2.4 mmol) in methanol (10 mL) was treated with p-toluenesulfonic acid (40 mg, 0.24 mmol) and heated overnight at 50° C. The solvent was removed in vacuo to afford 4-(8-(4-bromobutyl)-2-chloro-9H-purin-6-yl)morpholine as a white solid, which was used in the next step without any further purification (880 mg, quant). LC/MS (ESI+): m/z 375 (M+H)

Step 3: 4-(2-chloro-6,7,8,9-tetrahydropyrido[2,1-e]purin-4-yl)morpholine

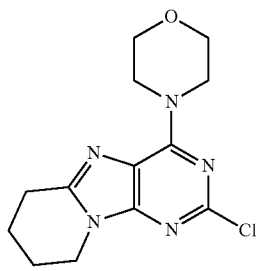

A suspension of 4-(8-(4-bromobutyl)-2-chloro-9H-purin-6-yl)morpholine (880 mg, 2.4 mmol) in DMSO (6.7 mL) was treated with cesium carbonate (1.5 g, 4.7 mmol) and heated at 50° C. for 1 hr. The reaction mixture was cooled to ambient temperature and diluted with water and DCM and the layers separated. The aqueous phase was extracted into DCM (3×), dried over sodium sulfate, filtered, and absorbed onto celite for purification by flash chromatography to afford 4-(2-chloro-6,7,8,9-tetrahydropyrido[2,1-e]purin-4-yl)morpholine as a white solid (460 mg, 67%). $^1$H NMR (400 MHz, DMSO) δ 4.28-4.03 (m, 4H), 4.00 (m, 2H), 3.69 (m, 4H), 2.90 (m, 2H), 2.01-1.86 (m, 4H). LC/MS (ESI+): m/z 294 (M+H)

Step 4: Following General Procedure A, 4-(2-chloro-6,7,8,9-tetrahydropyrido[2,1-e]purin-4-yl)morpholine (310 mg, 1.0 mmol), 5-(4,4,5,5-tetramethyl-1,3,2-dioxaborolan-2-yl)pyrimidin-2-amine (300 mg, 1.4 mmol), and tetrakis(triphenylphosphine)-palladium(0) (61 mg, 52 umol, 5.0 mol %) suspended in MeCN (2.6 mL) and 1.0M Na$_2$CO$_3$ (2.0 mL) was heated under microwave irradiation at 140° C. for 15 minutes. The cooled reaction mixture was concentrated to dryness in vacuo. The resultant residue was purified via HPLC to afford 106 as a white solid (220 mg, 60%). $^1$H NMR (500 MHz, DMSO) δ 9.09 (s, 2H), 7.01 (s, 2H), 4.23 (s, 4H), 4.08 (s, 2H), 3.73 (s, 4H), 2.92 (s, 2H), 2.00 (s, 2H), 1.93 (s, 2H). LCMS: R$_T$=6.13 min, M+H$^+$=353.1

Example 107

5-(4-morpholino-6,7,8,9-tetrahydropyrido[2,1-e]purin-2-yl)pyridin-2-amine 107

4-(2-chloro-6,7,8,9-tetrahydropyrido[2,1-e]purin-4-yl)morpholine, from Example 106 (150 mg, 0.50 mmol), 5-(4,4,5,5-tetramethyl-1,3,2-dioxaborolan-2-yl)pyridin-2-amine (140 mg, 0.64 mmol), and tetrakis(triphenylphosphine)-palladium(0) (29 mg, 25 umol, 5.0 mol %) suspended in MeCN (1.2 mL) and 1.0M Na$_2$CO$_{3(aq)}$ (0.94 mL) were heated under microwave irradiation at 140° C. for 15 minutes. The cooled reaction mixture was concentrated to dryness in vacuo. The resultant residue was purified via HPLC to afford 107 as a white solid (170 mg, 63%). $^1$H NMR (500 MHz, DMSO) δ 8.91 (s, 1H), 8.27 (d, J=8.6 Hz, 1H), 6.48 (d, J=8.5 Hz, 1H), 6.27 (s, 2H), 4.22 (s, 4H), 4.07 (s, 2H), 3.73 (s, 4H), 2.91 (s, 2H), 2.01 (s, 2H), 1.92 (s, 2H). LCMS: R$_T$=6.23 min, M+H$^+$=352.1

Example 108

5-(4-morpholino-8,9-dihydro-6h-[1,4]oxazino[3,4-e]purin-2-yl)-4-(trifluoromethyl)pyridyl-2-amine 108

2-Chloro-4-morpholino-8,9-dihydro-6H-[1,4]oxazino[3,4-e]purine (80 mg, 0.0003 mol) and 5-(4,4,5,5-tetramethyl-1,3,2-dioxaborolan-2-yl)-4-(trifluoromethyl)romoace-2-amine (120 mg, 0.0004 mol) were reacted under microwave Suzuki palladium conditions to give 108 (40 mg, 40% yield). LC/MS (ESI+): m/z 422 (M+H). $^1$H NMR (400 MHz, DMSO) δ 8.56-8.42 (m, 1H), 6.81 (s, 1H), 6.76 (s, 2H), 4.93 (s, 2H), 4.16 (d, J=20.6 Hz, 8H), 3.80-3.58 (m, 4H)

Example 109

5-(4-morpholino-7,8-dihydro-6h-pyrrolo[2,1-e]purin-2-yl)pyrimidin-2-amine 109

Step 1: 4-(9-allyl-2-chloro-8-iodo-9H-purin-6-yl)morpholine

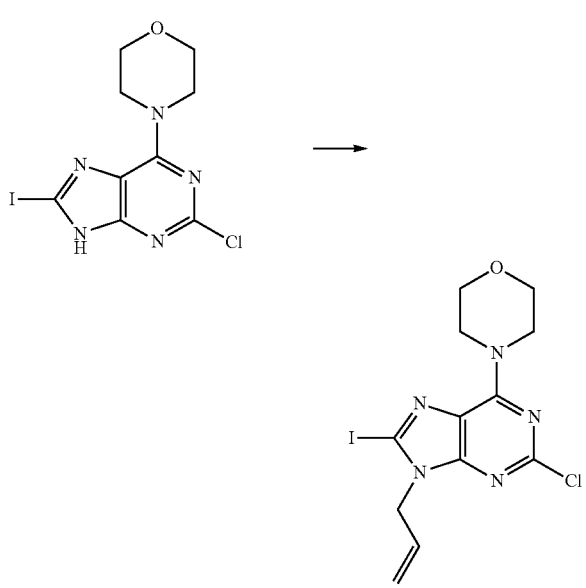

4-(2-chloro-8-iodo-9H-purin-6-yl)morpholine (500 mg, 1.0 mmol) was stirred together with cesium carbonate (890 mg, 2.7 mmol) in DMF (4.2 mL) at ambient temperature for 10 minutes. Allyl bromide (0.36 mL, 4.1 mmol) was introduced and the reaction mixture was heated at 50° C. for 2 hr. The mixture was cooled to ambient temperature and diluted with brine and DCM and the layers separated. The aqueous phase was extracted into DCM (3×), dried over sodium sulfate, filtered, and absorbed onto celite for purification by flash chromatography to afford 4-(9-allyl-2-chloro-8-iodo-9H-purin-6-yl)morpholine as a white foam (480 mg, 90%). $^1$H NMR (500 MHz, DMSO) δ 5.94 (d, J=10.6 Hz, 2H), 5.76 (s, 1H), 5.19 (d, J=10.3 Hz, 2H), 4.79 (d, J=16.9 Hz, 2H), 4.69 (s, 2H), 3.73 (s, 4H). LC/MS (ESI+): m/z 406 (M+H)

Step 2: 4-(2-chloro-7,8-dihydro-6H-pyrrolo[2,1-e]purin-4-yl)morpholine

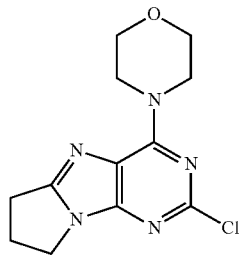

4-(9-Allyl-2-chloro-8-iodo-9H-purin-6-yl)morpholine (230 mg, 0.57 mmol) was added to a solution of 0.50M 9-borabicyclo[3.3.1]nonane in hexane (1.7 mL) at ambient temperature. THF was added to solubilize the reaction mixture. No conversion prompted addition of 0.50M 9-borabicyclo[3.3.1]nonane in hexane (1.7 mL) and the reaction mixture stirred for 15 hr. Potassium phosphate monohydrate (200 mg, 0.85 mmol) and tetrakis(triphenylphosphine)-palladium(0) (16 mg, 14 umol, 2.5 mol %) were added and the reaction mixture was heated at 60° C. for 15 hr. The mixture was cooled to ambient temperature and diluted with water and DCM and the layers separated. The aqueous phase was extracted into DCM (3×), dried over sodium sulfate, filtered, and absorbed onto celite for purification by flash chromatography to afford 4-(2-chloro-7,8-dihydro-6H-pyrrolo[2,1-e]purin-4-yl)morpholine as a solid (32 mg, 20%). LC/MS (ESI+): m/z 280 (M+H)

Step 3: 4-(2-chloro-7,8-dihydro-6H-pyrrolo[2,1-e]purin-4-yl)morpholine (32 mg, 0.11 mmol), 5-(4,4,5,5-tetramethyl-1,3,2-dioxaborolan-2-yl)pyrimidin-2-amine (33 mg, 0.15 mmol), and tetrakis(triphenylphosphine)-palladium(0) (6.6 mg, 5.7 umol, 5.0 mol %) suspended in MeCN (0.28 mL) and 1.0M Na$_2$CO$_3$ (0.22 mL) was heated under microwave irradiation at 140° C. for 15 minutes. The cooled reaction mixture was concentrated to dryness in vacuo. The resultant residue was purified via HPLC to afford 109 as a white solid (1.7 mg, 4.4%). $^1$H NMR (400 MHz, DMSO) δ 8.99 (s, 1H), 7.75 (s, 1H), 6.95 (d, J=1.5 Hz, 1H), 6.92 (s, 1H), 6.88 (s, 1H), 6.02 (s, 1H), 5.85 (hept, J=6.6 Hz, 1H), 4.65 (s, 1H), 4.50-4.36 (m, 6H), 3.73 (s, 6H), 2.24 (s, 3H), 1.44 (d, J=6.6 Hz, 6H). LCMS: R$_T$=3.48 min, M+H$^+$=339.1

Example 110

6,6-dimethyl-4-morpholino-2-(1H-pyrrolo[2,3-b]pyridin-5-yl)-8,9-dihydro-6H-[1,4]oxazino[3,4-e]purine 110

2-Chloro-6,6-dimethyl-4-morpholino-8,9-dihydro-6H-[1,4]oxazino[3,4-e]purine (100 mg, 0.0003 mol) and 5-(4,4,5,5-tetramethyl-1,3,2-dioxaborolan-2-yl)-1H-pyrrolo[2,3-b]pyridine (110 mg, 0.00046 mol) were reacted under microwave Suzuki palladium conditions to give 110 (54 mg, 50% yield). LC/MS (ESI+): m/z 406 (M+H). $^1$H NMR (400 MHz, DMSO) δ 11.75 (s, 1H), 9.27 (d, J=1.8 Hz, 1H), 8.88 (d, J=1.6 Hz, 1H), 7.60-7.41 (m, 1H), 6.57 (d, J=1.6 Hz, 1H), 4.29 (s, 4H), 4.17 (dd, J=18.0, 5.1 Hz, 4H), 3.88-3.69 (m, 4H), 1.60 (s, 6H)

Example 111

5-(6,6-dimethyl-4-morpholino-8,9-dihydro-6H-[1,4]oxazino[3,4-e]purin-2-yl)pyridin-2-amine 111

2-Chloro-6,6-dimethyl-4-morpholino-8,9-dihydro-6H-[1,4]oxazino[3,4-e]purine (100 mg, 0.0003 mol) and 5-(4,4,5,5-tetramethyl-1,3,2-dioxaborolan-2-yl)romoace-2-amine (110 mg, 0.0005 mol) were reacted under microwave Suzuki palladium conditions to give 111 (75 mg, 70% yield). LC/MS (ESI+): m/z 382 (M+H). $^1$H NMR (400 MHz, DMSO) δ 8.92 (d, J=2.1 Hz, 1H), 8.27 (dd, J=8.7, 2.2 Hz, 1H), 8.16 (s, 1H), 6.49 (d, J=8.7 Hz, 1H), 6.26 (s, 2H), 4.22 (s, 4H), 4.12 (s, 4H), 3.86-3.65 (m, 4H), 1.57 (s, 6H)

Example 112

5-(4-morpholino-8,9-dihydrospiro[[1,3]oxazino[2,3-e]purine-7,1'-cyclopropane]-2-yl)pyrimidin-2-amine 112

Step 1: 1-(2-(2-chloro-6-morpholino-9H-purin-9-yl)ethyl)cyclopropanol

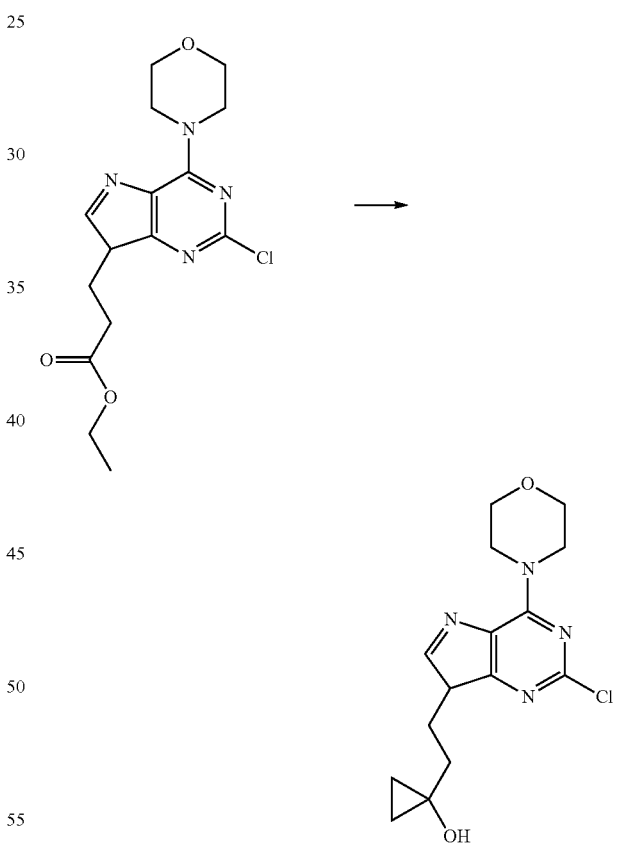

A solution of ethyl 3-(2-chloro-6-morpholino-9H-purin-9-yl)propanoate (500 mg, 1.5 mmol) in diethylether (37 mL) was treated with titanium (IV) ethoxide (31 uL, 0.15 mmol) followed by the dropwise addition of 3.0M ethylmagnesium bromide in ether (0.98 mL, 2.9 mmol) at ambient temperature for 90 minutes. Partial conversion prompted the addition of titanium (IV) ethoxide (31 uL, 0.15 mmol) and 3.0M ethylmagnesium bromide in ether (0.98 mL, 2.9 mmol). After 2 hr, the reaction mixture was quenched with an aqueous 1.0M solution of HCl (20 mL) and filtered through a plug of celite, washing with ethyl acetate. The mixture was diluted with water and ethyl acetate and the layers separated. The aqueous phase was extracted into EtOAc (3×), dried over sodium sulfate, filtered, and absorbed onto celite for purification by flash chromatography to afford 1-(2-(2-chloro-6-morpholino-9H-purin-9-yl)ethyl)cyclopropanol as a colorless oil (220 mg, 46%). LC/MS (ESI+): m/z 324 (M+H)

Step 2: 1-(2-(2-chloro-8-iodo-6-morpholino-9H-purin-9-yl)ethyl)cyclopropanol

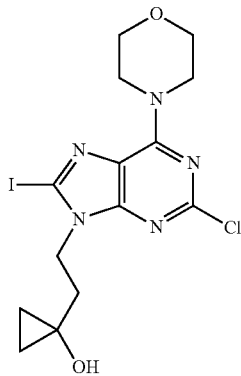

A solution of 1-(2-(2-chloro-6-morpholino-9H-purin-9-yl)ethyl)cyclopropanol (220 mg, 0.68 mmol) and N,N,N',N'-tetramethylethylene-diamine (0.15 mL, 1.0 mmol) in THF (4.9 mL) was cooled to −42° C. and treated with a solution of 2.5M n-butyllithium in hexane (1.5 mL, 3.7 mmol) dropwise over 5 minutes. After 30 minutes at −42° C., 1-chloro-2-iodoethane (0.31 mL, 3.3 mmol) was added and the reaction mixture was slowly warmed to 0° C. over 1 hr. The mixture was quenched with a saturated solution of NH₄Cl, and diluted with ethyl acetate. The aqueous layer was extracted into ethyl acetate (3×), and the combined organics were dried over sodium sulfate, filtered, and absorbed onto celite for purification by flash chromatography to afford 1-(2-(2-chloro-8-iodo-6-morpholino-9H-purin-9-yl)ethyl)cyclopropanol as a colorless oil (220 mg, 71%). LC/MS (ESI+): m/z 450 (M+H)

Step 3: 2-chloro-4-morpholino-8,9-dihydrospiro[[1,3]oxazino[2,3-e]purine-7,1'-cyclopropane]

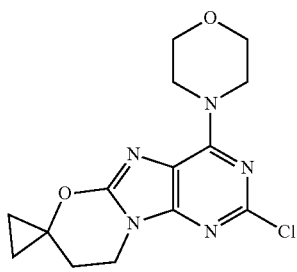

Copper (I) iodide (4.6 mg, 24 umol), picolinic acid (6.0 mg, 48 umol), and potassium phosphate (210 mg, 0.97 mmol) were combined in an oven-dried round bottom flask and evacuated/recycled with N₂ (3×). Subsequently, a solution of 1-(2-(2-chloro-8-iodo-6-morpholino-9H-purin-9-yl)ethyl)cyclopropanol (220 mg, 0.48 mmol) dissolved in DMSO (3.4 mL) was introduced via syringe. The reaction mixture was heated at 80° C. for 20 hr. The reaction mixture was cooled to ambient temperature and diluted with water and ethyl acetate and the layers separated. The aqueous phase was extracted into EtOAc (3×), dried over sodium sulfate, filtered, and absorbed onto celite for purification by flash chromatography to afford 2-chloro-4-morpholino-8,9-dihydrospiro[[1,3]oxazino[2,3-e]purine-7,1'-cyclopropane] as a yellow solid (41 mg, 26%). LC/MS (ESI+): m/z 322 (M+H)

Step 4: 2-chloro-4-morpholino-8,9-dihydrospiro[[1,3]oxazino[2,3-e]purine-7,1'-cyclopropane](37 mg, 0.11 mmol), 5-(4,4,5,5-tetramethyl-1,3,2-dioxaborolan-2-yl)pyrimidin-2-amine (33 mg, 0.15 mmol), and tetrakis(triphenylphosphine)-palladium(0) (6.6 mg, 5.7 umol, 5.0 mol %) suspended in MeCN (0.28 mL) and 1.0M Na₂CO₃ (0.22 mL) was heated under microwave irradiation at 140° C. for 15 minutes. The cooled reaction mixture was concentrated to dryness in vacuo. The resultant residue was purified via HPLC to afford 112 as a white solid (22 mg, 50%). $^1$H NMR (400 MHz, DMSO) δ 9.07 (s, 2H), 6.96 (s, 2H), 4.22 (t, J=6.0 Hz, 2H), 4.11 (s, 4H), 3.75-3.65 (m, 4H), 2.26 (t, J=5.9 Hz, 2H), 1.08 (t, J=6.4 Hz, 2H), 0.90 (t, J=6.6 Hz, 2H). LCMS: $R_T$=3.57 min, M+H⁺=381.1.

Example 113

5-(4-morpholino-8,9-dihydro-6h-[1,4]oxazino[3,4-e]purin-2-yl)pyrimidin-2-amine 113

Step 1: 2-chloro-6-morpholino-9-(tetrahydro-2H-pyran-2-yl)-9H-purine-8-carbaldehyde

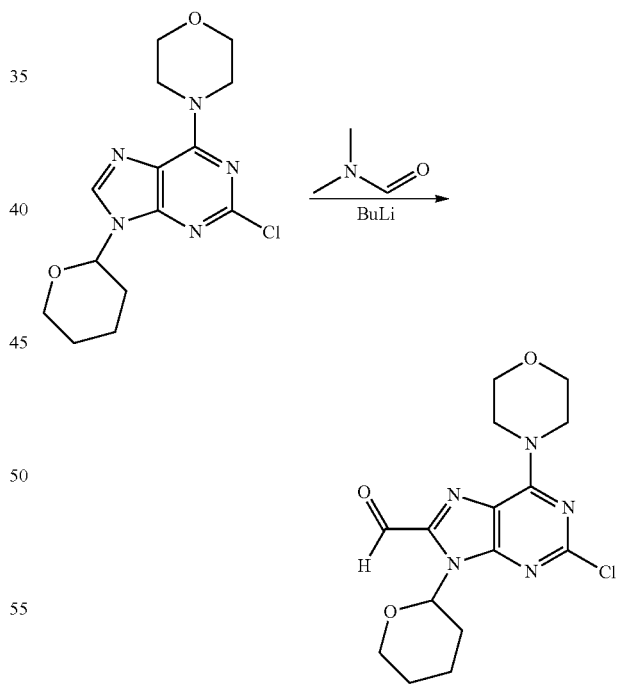

To a mixture of 4-(2-chloro-9-(tetrahydro-2H-pyran-2-yl)-9H-purin-6-yl)morpholine (5 g, 20 mmol) in THF (100 mL) at −78° C. was added tetramethylethylenediamine (3.5 mL, 23 mmol) followed by 2.5 M of n-BuLi (9.3 mL, 23 mmol) dropwise. The reaction was stirred at −78° C. for 1 hour and then N,N-dimethylformamide (2.4 mL, 31 mmol) was added, continue stirred for 1 hours at −78° C. The reaction was quenched with water and extracted with EtOAc. The organic extracts were washed with water, brine, dried over MgSO$_4$ and concentrated. The crude material was triturated with EtOAc to give pure 2-chloro-6-morpholino-9-(tetrahydro-2H-pyran-2-yl)-9H-purine-8-carbaldehyde as a white solid (4.5 g, 80% yield). LC/MS (ESI+): m/z 353 (M+H)

Step 2: (2-chloro-6-morpholino-9-(tetrahydro-2H-pyran-2-yl)-9H-purin-8-yl)methanol

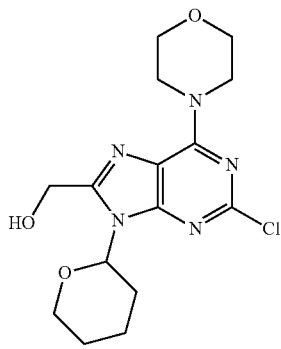

2-Chloro-6-morpholino-9-(tetrahydro-2H-pyran-2-yl)-9H-purine-8-carbaldehyde (3.8 g, 11 mmol) in MeOH (22 mL) was treated with sodium tetrahydroborate (0.817 g, 22 mmol), and stirred at room temperature for 1 hour. The reaction was quenched with water and extracted with EtOAc. The organic extracts were washed with water, brine, dried over MgSO$_4$ and concentrated. The crude material was purified with isco with 0-80% EtOAc/hexane to give the pure (2-chloro-6-morpholino-9-(tetrahydro-2H-pyran-2-yl)-9H-purin-8-yl)methanol (3.4 g, 89% yield). LC/MS (ESI+): m/z 354 (M+H)

Step 3: (2-chloro-6-morpholino-9H-purin-8-yl)methanol

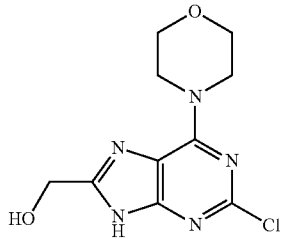

(2-Chloro-6-morpholino-9-(tetrahydro-2H-pyran-2-yl)-9H-purin-8-yl)methanol (3.4 g, 0.0096 mol) in MeOH (20 mL) was treated with a catalytic amount of p-toluenesulfonic acid (0.25 g, 0.00144 mol). The reaction mixture was heated to 50° C. overnight and was then concentrated under reduce pressure. The residue was partitioned between water and EtOAc. The organic extracts were washed with water, brine, dried over MgSO$_4$ and concentrated to dryness to give (2-chloro-6-morpholino-9H-purin-8-yl)methanol (2.6 g, 100% yield). LC/MS (ESI+): m/z 271 (M+H)

Step 4: 2-chloro-4-morpholino-8,9-dihydro-6H-[1,4]oxazino[3,4-e]purine

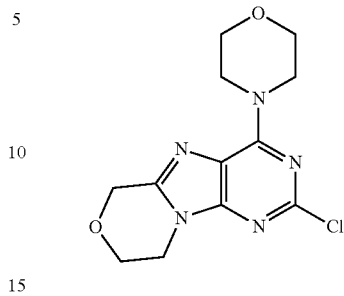

A mixture of (2-chloro-6-morpholino-9H-purin-8-yl)methanol (1 g, 0.004 mol), 1,2-dibromoethane (0.64 mL, 0.0074 mol) and cesium carbonate (3.6 g, 0.011 mol) in DMF (14 mL) was heated at 90° C. for 12 hours. The reaction mixture was filtered and partitioned between water and EtOAc. The organic extracts were washed with water, brine and dried over MgSO$_4$ and concentrated. The crude product was purified by isco with 0-50% EtOAc/hexane to give 2-chloro-4-morpholino-8,9-dihydro-6H-[1,4]oxazino [3,4-e]purine (0.7 g, 60%). LC/MS (ESI+): m/z 297 (M+H)

Step 5: 2-Chloro-4-morpholino-8,9-dihydro-6H-[1,4]oxazino[3,4-e]purine (160 mg, 0.00056 mol) and 5-(4,4,5,5-tetramethyl-1,3,2-dioxaborolan-2-yl)pyrimidin-2-amine (180 mg, 0.00083 mol) were reacted under microwave Suzuki palladium conditions to give 113 (40 mg, 15% yield) along with some side product, (2-(2-aminopyrimidin-5-yl)-6-morpholino-9-vinyl-9H-purin-8-yl)methanol (7 mg). LC/MS (ESI+): m/z 355 (M+H). $^1$H NMR (400 MHz, DMSO) δ 9.10 (s, 2H), 7.00 (s, 2H), 4.91 (s, 2H), 4.34-4.07 (m, 8H), 3.90-3.63 (m, 4H). $^1$H NMR (400 MHz, DMSO) δ 9.10 (s, 2H), 7.35 (dd, J=15.9, 9.5 Hz, 1H), 7.05 (s, 2H), 6.47 (d, J=15.9 Hz, 1H), 5.73 (t, J=5.6 Hz, 1H), 5.28 (d, J=9.4 Hz, 1H), 4.71 (d, J=5.6 Hz, 2H), 4.27 (s, 4H), 3.88-3.63 (m, 4H)

Example 114

5-(4-morpholino-8,9-dihydrospiro[[1,4]oxazino[3,4-e]purine-6,3'-oxetane]-2-yl)pyrimidin-2-amine 114

Step 1: 3-(2-chloro-6-morpholino-9-(tetrahydro-2H-pyran-2-yl)-9H-purin-8-yl)oxetan-3-ol

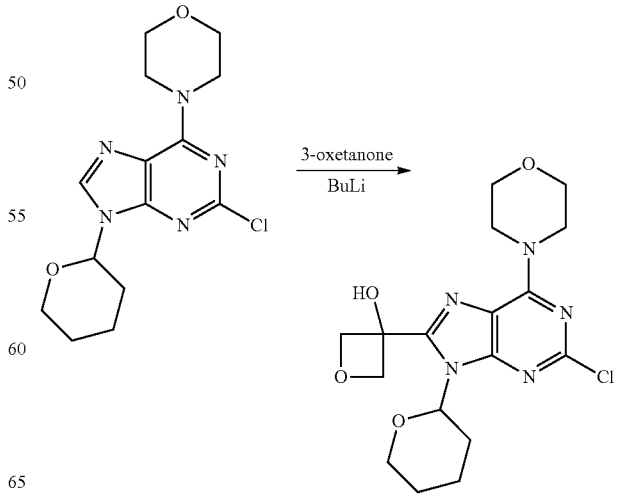

To a mixture of 4-(2-chloro-9-(tetrahydro-2H-pyran-2-yl)-9H-purin-6-yl)morpholine (2.9 g, 9 mmol) in THF (50 mL) at −78° C. was added 2.5 M of n-BuLi (9 mL, 22 mmol) dropwise. The reaction was stirred at −78° C. for 30 minutes and then 3-oxetanone (1.3 mL, 18 mmol) was added, continue stirred for 2 hours at −78° C. The reaction was quenched with water and extracted with EtOAc. The organic extracts were washed with water, brine, dried over MgSO$_4$ and concentrated. The crude material was purified by Isco chromatography with 0-100% EtOAc/hexane to give pure 3-(2-chloro-6-morpholino-9-(tetrahydro-2H-pyran-2-yl)-9H-purin-8-yl)oxetan-3-ol as a white solid (2.5 g, 70% yield). LC/MS (ESI+): m/z 397 (M+H)

Step 2: 3-(2-chloro-6-morpholino-9H-purin-8-yl)oxetan-3-ol

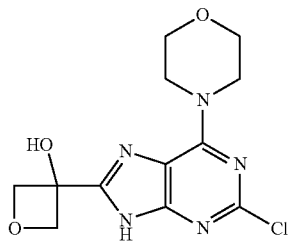

3-(2-Chloro-6-morpholino-9-(tetrahydro-2H-pyran-2-yl)-9H-purin-8-yl)oxetan-3-ol (1.8 g, 0.0045 mol) in MeOH (50 mL) was treated with cat. amount of p-toluenesulfonic acid (78 mg, 0.00044 mol). The reaction mixture was heated to 50° C. overnight and was then concentrated under reduce pressure. The residue was partitioned between water and EtOAc. The organic extracts were washed with water, brine, dried over MgSO$_4$ and concentrated to dryness to give 3-(2-chloro-6-morpholino-9H-purin-8-yl)oxetan-3-ol (1.2 g, 84% yield). LC/MS (ESI+): m/z 312 (M+H)

Step 3: 2-chloro-4-morpholino-8,9-dihydrospiro[[1,4]oxazino[3,4-e]purine-6,3'-oxetane]

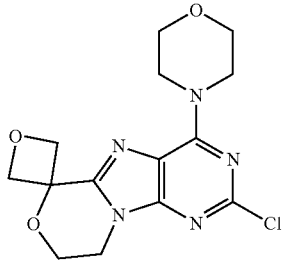

A mixture of 3-(2-chloro-6-morpholino-9H-purin-8-yl)oxetan-3-ol (356 mg, 0.0011 mol), 1,2-dibromoethane (0.21 mL, 0.0024 mol) and cesium carbonate (1.13 g, 0.0034 mol) in DMF (4 mL) was heated at 90° C. for 12 hours. The reaction mixture was filtered and partitioned between water and EtOAc. The organic extracts were washed with water, brine and dried over MgSO$_4$ and concentrated. The crude product was purified by isco with 0-80% EtOAc/hexane to give 2-chloro-4-morpholino-8,9-dihydrospiro[[1,4]oxazino[3,4-e]purine-6,3'-oxetane](0.34 g, 85%). LC/MS (ESI+): m/z 339 (M+H)

Step 4: 2-Chloro-4-morpholino-8,9-dihydrospiro[[1,4]oxazino[3,4-e]purine-6,3'-oxetane](200 mg, 0.0006 mol) and 5-(4,4,5,5-tetramethyl-1,3,2-dioxaborolan-2-yl)pyrimidin-2-amine (210 mg, 0.00095 mol) were reacted under microwave Suzuki palladium conditions to give 114 (0.123 mg, 60% yield). LC/MS (ESI+): m/z 397 (M+H). $^1$H NMR (400 MHz, DMSO) δ 9.10 (s, 2H), 7.02 (s, 2H), 4.97 (d, J=7.1 Hz, 2H), 4.72 (d, J=7.1 Hz, 2H), 4.29 (s, 4H), 4.16 (s, 4H), 3.90-3.62 (m, 4H)

Example 115

5-(7,7-dimethyl-4-morpholino-8,9-dihydro-7h-[1,3]oxazino[2,3-e]purin-2-yl)pyrimidin-2-amine 115

Step 1: ethyl 3-(2-chloro-6-morpholino-9H-purin-9-yl)propanoate

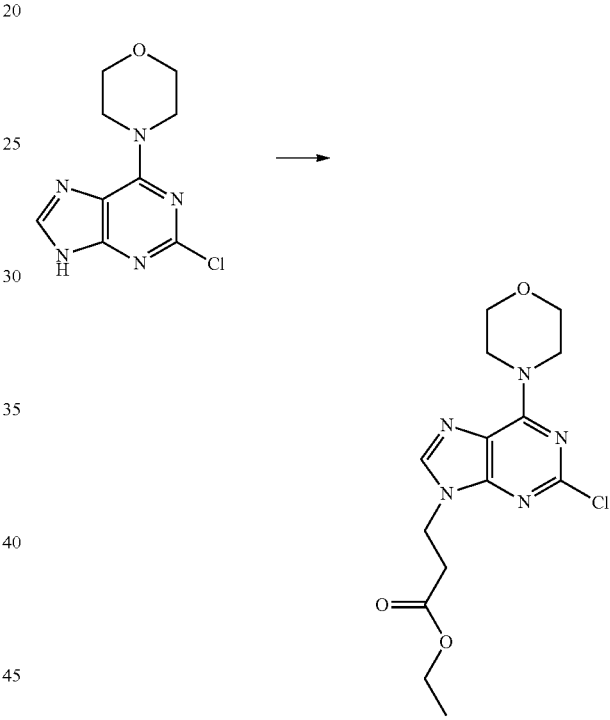

A solution of 4-(2-chloro-9H-purin-6-yl)morpholine (3.0 g, 13 mmol) in DMF (39 mL) was treated with cesium carbonate (8.2 g, 25 mmol) and stirred at ambient temperature for 10 minutes. 3-bromopropanoic acid, ethyl ester (6.8 g, 38 mmol) was introduced and the reaction mixture was heated at 50° C. for 2 hr. Partial conversion prompted the addition of cesium carbonate (8.2 g, 25 mmol) and 3-bromopropanoic acid, ethyl ester (6.8 g, 38 mmol), and the reaction mixture was heated at 70° C. The reaction mixture was cooled to ambient temperature and diluted with brine and DCM and the layers separated. The aqueous phase was extracted into DCM (3×), dried over sodium sulfate, filtered, and absorbed onto celite for purification by flash chromatography to afford ethyl 3-(2-chloro-6-morpholino-9H-purin-9-yl)propanoate as a white solid (3.5 g, 83%). LC/MS (ESI+): m/z 340 (M+H)

Step 2: 4-(2-chloro-6-morpholino-9H-purin-9-yl)-2-methylbutan-2-ol

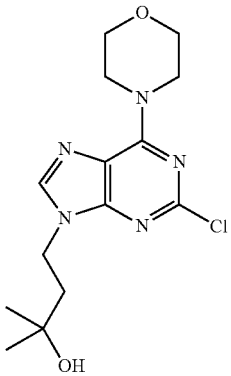

A solution of ethyl 3-(2-chloro-6-morpholino-9H-purin-9-yl)propanoate (500 mg, 1.5 mmol) in THF (30 mL) at 0° C. was treated drop-wise with a solution of 3.0M methylmagnesium chloride in THF (2.0 mL). After 90 minutes at 0° C., the reaction mixture was treated with a saturated solution of NH₄Cl and diluted with brine and DCM and the layers separated. The aqueous phase was extracted into DCM (3×), dried over sodium sulfate, filtered, and absorbed onto celite for purification by flash chromatography to afford 4-(2-chloro-6-morpholino-9H-purin-9-yl)-2-methylbutan-2-ol as a white foam (452 mg, 94%). LC/MS (ESI+): m/z 326 (M+H)

Step 3: 4-(2-chloro-8-iodo-6-morpholino-9H-purin-9-yl)-2-methylbutan-2-ol

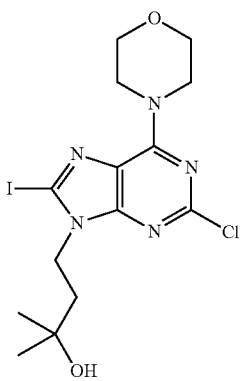

A solution of 4-(2-chloro-6-morpholino-9H-purin-9-yl)-2-methylbutan-2-ol (360 mg, 1.1 mmol) and N,N,N',N'-tetramethylethylenediamine (0.25 mL, 1.7 mmol) in THF (8.1 mL) was cooled to −42° C. and treated with a solution of 2.5M n-butyllithium in hexane (BuLi, 2.0 mL, 5.0 mmol) dropwise over 5 minutes. After 30 minutes at −42° C., 1-chloro-2-iodoethane (0.51 mL, 5.4 mmol) was added and the reaction mixture was slowly warmed to 0° C. over 1 hr. The mixture was quenched with a saturated solution of NH₄Cl, and diluted with ethyl acetate. The aqueous layer was extracted into ethyl acetate (3×), and the combined organics were dried over sodium sulfate, filtered, and absorbed onto celite for purification by flash chromatography to afford 4-(2-chloro-8-iodo-6-morpholino-9H-purin-9-yl)-2-methylbutan-2-ol as a white foam (390 mg, 78%). LC/MS (ESI+): m/z 452 (M+H)

Step 4: 2-chloro-7,7-dimethyl-4-morpholino-8,9-dihydro-7H-[1,3]oxazino[2,3-e]purine

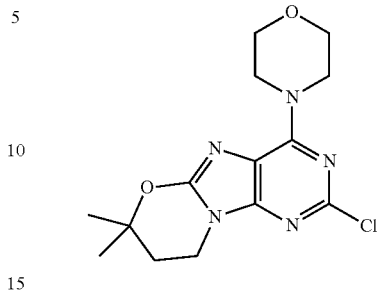

Copper (I) iodide (3.2 mg, 17 umol), picolinic acid (4.1 mg, 33 umol), and potassium phosphate (140 mg, 0.67 mmol) were combined in an oven-dried round bottom flask and evacuated/recycled with N₂ (3×). Subsequently, a solution of 4-(2-chloro-8-iodo-6-morpholino-9H-purin-9-yl)-2-methylbutan-2-ol (150 mg, 0.33 mmol) dissolved in DMSO (2.4 mL) was introduced via syringe. The reaction mixture was heated at 80° C. for 20 hr. Partial conversion prompted the addition of copper (I) iodide (3.2 mg, 17 umol), picolinic acid (4.1 mg, 33 umol), and potassium phosphate (140 mg, 0.67 mmol) and the reaction mixture continued to stir at 80° C. for 20 hr. The reaction mixture was cooled to ambient temperature and diluted with water and ethyl acetate and the layers separated. The aqueous phase was extracted into EtOAc (3×), dried over sodium sulfate, filtered, and absorbed onto celite for purification by flash chromatography to afford 2-chloro-7,7-dimethyl-4-morpholino-8,9-dihydro-7H-[1,3]oxazino[2,3-e]purine as a white solid (61 mg, 56%). LC/MS (ESI+): m/z 324 (M+H)

Step 5: 2-Chloro-7,7-dimethyl-4-morpholino-8,9-dihydro-7H-[1,3]oxazino[2,3-e]purine (61 mg, 0.19 mmol), 5-(4,4,5,5-tetramethyl-1,3,2-dioxaborolan-2-yl)pyrimidin-2-amine (54 mg, 0.24 mmol), and tetrakis(triphenylphosphine)-palladium(0) (11 mg, 9.4 umol, 5.0 mol %) suspended in MeCN (0.46 mL) and 1.0M Na₂CO₃(aq) (0.36 mL) was heated under microwave irradiation at 140° C. for 15 minutes. The cooled reaction mixture was concentrated to dryness in vacuo. The resultant residue was purified via HPLC to afford 115 as a white solid (27 mg, 37%). ¹H NMR (400 MHz, DMSO) δ 9.06 (s, 2H), 6.95 (s, 2H), 4.18-4.06 (m, 6H), 3.75-3.65 (m, 4H), 2.15 (t, J=6.2 Hz, 2H), 1.46 (s, 6H). LCMS: R$_T$=2.75 min, M+H⁺=383.1

Example 116

5-(4-morpholino-6-(trifluoromethyl)-8,9-dihydro-6H-[1,4]oxazino[3,4-e]purin-2-yl)pyridin-2-amine
116

2-Chloro-4-morpholino-6-(trifluoromethyl)-8,9-dihydro-6H-[1,4]oxazino[3,4-e]purine, from Examples 139 and 140 (100 mg, 0.0003 mol) and 5-(4,4,5,5-tetramethyl-1,3,2-dioxaborolan-2-yl)romoace-2-amine (120 mg, 0.00055 mol) were reacted under microwave Suzuki palladium conditions to give 116 (56 mg, 56% yield). LC/MS (ESI+): m/z 422 (M+H). ¹H NMR (400 MHz, DMSO) δ 8.94 (d, J=2.0 Hz, 1H), 8.28 (dd, J=8.7, 2.2 Hz, 1H), 6.50 (d, J=8.7 Hz, 1H), 6.32 (s, 2H), 5.87 (q, J=6.9 Hz, 1H), 4.49-4.10 (m, 8H), 3.75 (t, J=4.6 Hz, 4H)

Example 117

5-(6,6-(hexadeuterio)dimethyl-4-morpholino-8,9-dihydro-6h-[1,4]oxazino[3,4-e]purin-2-yl)pyrimidin-2-amine 117

Step 1: 2-(2-chloro-6-morpholino-9-(tetrahydro-2H-pyran-2-yl)-9H-purin-8-yl)-1,3-hexadeuterio-propan-2-ol

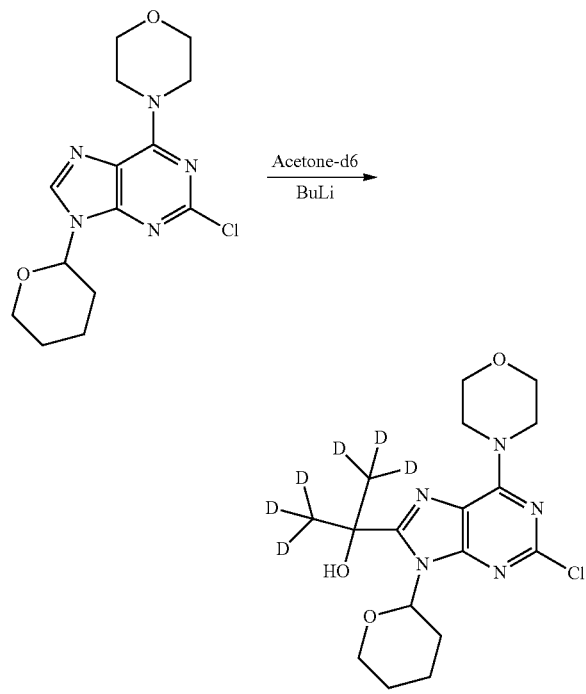

To a mixture of 4-(2-chloro-9-(tetrahydro-2H-pyran-2-yl)-9H-purin-6-yl)morpholine (5 g, 0.02 mol) in THF (100 mL) at −78° C. was added 2.5 M of n-BuLi (12 mL, 0.031 mol) dropwise. The reaction was stirred at −78° C. for 30 minutes and then acetone-d6 (2.5 mL, 0.034 mol) was added, continue stirred for 2 hours at −78° C. The reaction was quenched with water and extracted with EtOAc. The organic extracts were washed with water, brine, dried over MgSO₄ and concentrated. The crude material was purified by Isco chromatography with 0-100% EtOAc/hexane to give pure 2-(2-chloro-6-morpholino-9-(tetrahydro-2H-pyran-2-yl)-9H-purin-8-yl)-1,3-hexadeuterio-propan-2-ol as a white solid (5.7 g, 95% yield). LC/MS (ESI+): m/z 389 (M+H)

Step 2: 2-(2-chloro-6-morpholino-9H-purin-8-yl)-1,3-hexadeuterio-propan-2-ol

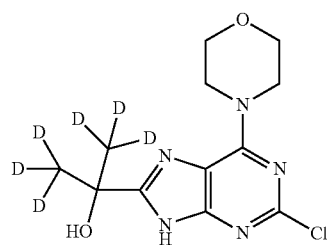

2-(2-Chloro-6-morpholino-9-(tetrahydro-2H-pyran-2-yl)-9H-purin-8-yl)-1,3-hexadeuterio-propan-2-ol (5.7 g, 0.015 mol) in MeOH (59 mL) was treated with a catalytic amount of p-toluenesulfonic acid (253 mg, 0.00147 mol). The reaction mixture was heated to 50° C. overnight and was then concentrated under reduce pressure. The residue was partitioned between water and EtOAc. The organic extracts were washed with water, brine, dried over MgSO₄ and concentrated to dryness to give 2-(2-chloro-6-morpholino-9H-purin-8-yl)-1,3-hexadeuterio-propan-2-ol (4.5 g, 100% yield). LC/MS (ESI+): m/z 304 (M+H)

Step 3: 2-chloro-6,6-(hexadeuterio)dimethyl-4-morpholino-8,9-dihydro-6H-10 [1,4]oxazino[3,4-e]purine

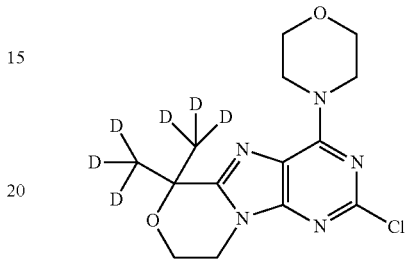

A mixture of 2-(2-chloro-6-morpholino-9H-purin-8-yl)-1,3-hexadeuterio-propan-2-ol (2 g, 0.006 mol), 1,2-dibromoethane (1.13 mL, 0.013 mol) and cesium carbonate (6.4 g, 0.02 mol) in DMF (4 mL) was heated at 90° C. for 12 hours. The reaction mixture was filtered and partitioned between water and EtOAc. The organic extracts were washed with water, brine and dried over MgSO₄ and concentrated. The crude product was purified by isco with 0-80% EtOAc/hexane to give the pure 2-chloro-6,6-(hexadeuterio)dimethyl-4-morpholino-8,9-dihydro-6H-[1,4]oxazino[3,4-e]purine (1.64 g, 82%). LC/MS (ESI+): m/z 331 (M+H)

Step 4: 2-Chloro-6,6-(hexadeuterio)dimethyl-4-morpholino-8,9-dihydro-6H-[1,4]oxazino[3,4-e]purine (1.6 g, 0.0048 mol) and 5-(4,4,5,5-tetramethyl-1,3,2-dioxaborolan-2-yl)pyrimidin-2-amine (1.6 g, 0.00073 mol) were reacted under Suzuki palladium conditions to give 117 (600 mg, 32% yield). LC/MS (ESI+): m/z 389 (M+H). ¹H NMR (400 MHz, DMSO) δ 9.09 (s, 1H), 7.00 (s, 1H), 4.23 (s, 2H), 4.10 (t, J=13.7 Hz, 2H), 3.85-3.67 (m, 2H)

Example 118

(S)-5-(6-ethyl-6-methyl-4-morpholino-8,9-dihydro-6H-[1,4]oxazino[3,4-e]purin-2-yl)pyrimidin-2-amine 118

Step 1: 2-(2-chloro-6-morpholino-9-(tetrahydro-2H-pyran-2-yl)-9H-purin-8-yl)butan-2-ol

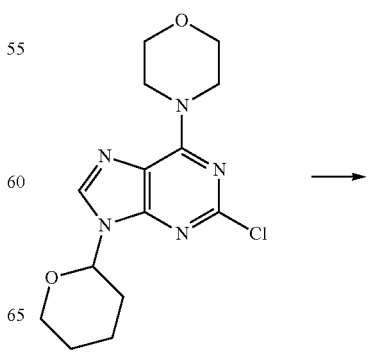

-continued

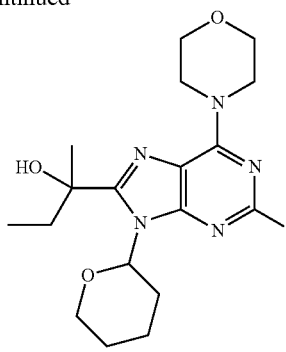

A solution of 4-(2-chloro-9-(tetrahydro-2H-pyran-2-yl)-9H-purin-6-yl)morpholine (5.0 g, 15 mmol) in THF (100 mL) was cooled to −42° C. and treated with a solution of 2.5M n-Butyllithium (n-BuLi) in hexane (12.35 mL, 31 mmol) dropwise over 5 minutes. After 15 min at −42° C., 2-butanone (3.1 mL, 34 mmol) was added and the reaction mixture was slowly warmed to 0° C. over 2 hr. The mixture was quenched with water, and diluted with ethyl acetate. The aqueous layer was extracted into ethyl acetate (3×), and the combined organics were dried over sodium sulfate, filtered, and concentrated in vacuo to provide 2-(2-chloro-6-morpholino-9-(tetrahydro-2H-pyran-2-yl)-9H-purin-8-yl)butan-2-ol as a yellow-orange foam (quant). LC/MS (ESI+): m/z 396 (M+H)

Step 2: 2-(2-chloro-6-morpholino-9H-purin-8-yl)butan-2-ol

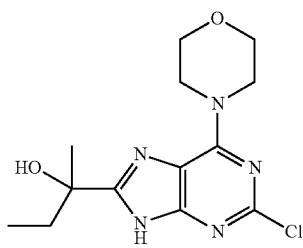

A suspension of 2-(2-chloro-6-morpholino-9-(tetrahydro-2H-pyran-2-yl)-9H-purin-8-yl)butan-2-ol (3.87 g, 9.8 mmol) in methanol (110 mL) was treated with p-toluenesulfonic acid (170 mg, 0.98 mmol) and heated overnight at 50° C. The solvent was removed in vacuo to afford 2-(2-chloro-6-morpholino-9H-purin-8-yl)butan-2-ol as a white solid, which was used in the next step without any further purification (3.0 g, quant). LC/MS (ESI+): m/z 312 (M+H)

Step 3: 2-chloro-6-ethyl-6-methyl-4-morpholino-8,9-dihydro-6H-[1,4]oxazino[3,4-e]purine

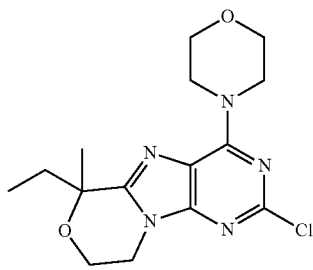

2-(2-chloro-6-morpholino-9H-purin-8-yl)butan-2-ol (1.0 g, 3.3 mmol) was dissolved in DMF (13 mL) and treated with 1,2-dibromoethane (0.57 mL, 6.6 mmol) and cesium carbonate (3.2 g, 9.9 mmol). The reaction mixture was heated at 90° C. for 2 hr and cooled to ambient temperature. The mixture was diluted with water and DCM and the layers separated. The aqueous phase was extracted into DCM (3×), dried over sodium sulfate, filtered, and absorbed onto celite for purification by flash chromatography to afford 2-chloro-6-ethyl-6-methyl-4-morpholino-8,9-dihydro-6H-[1,4]oxazino[3,4-e]purine as a white solid (730 mg, 66%). $^1$H NMR (400 MHz, DMSO) δ 4.22 (m, 4H), 4.01 (m, 2H), 3.78-3.63 (m, 4H), 2.01 (s, 2H), 1.87-1.73 (m, 2H), 1.49 (s, 3H), 0.77 (t, J=7.4 Hz, 3H). LC/MS (ESI+): m/z 338 (M+H)

Step 4: 2-chloro-6-ethyl-6-methyl-4-morpholino-8,9-dihydro-6H-[1,4]oxazino[3,4-e]purine (730 mg, 2.2 mmol), 5-(4,4,5,5-tetramethyl-1,3,2-dioxaborolan-2-yl)pyrimidin-2-amine (620 mg, 2.8 mmol), and tetrakis(triphenylphosphine)palladium(0) (120 mg, 0.11 mmol, 5.0 mol %) suspended in MeCN (5.2 mL) and 1.0M Na$_2$CO$_{3(aq)}$ (4.1 mL) was heated under microwave irradiation at 140° C. for 15 minutes. The cooled reaction mixture was concentrated to dryness in vacuo. The resultant residue was purified by SFC (conditions A) over 30 min, 35 mL/min] to separate the two enantiomers 118 and 120 to afford 118 as a white solid (120 mg and 116 mg, 30%). $^1$H NMR (400 MHz, DMSO) δ 9.09 (s, 2H), 7.00 (s, 2H), 4.29-4.01 (m, 8H), 3.80-3.68 (m, 4H), 2.00 (dq, J=14.5, 7.3 Hz, 1H), 1.84 (dt, J=14.4, 7.2 Hz, 1H), 1.52 (s, 3H), 0.82 (t, J=7.3 Hz, 3H). LCMS: R$_T$=9.49 min, M+H$^+$=397.1. Enantiomers 118 and 120 were analyzed and separated by chiral LCMS, rt=1.20 min and 1.65 min with mobile phase A=CO2, mobile phase B=methanol, isocratic 25% B, 5 ml/min flow rate, 40° C., ChiralCel OJ (4.6×50 mm, 3 micron particle, 230 nm UV detection, Berger Analytical SFC/MS Example 119

5-(6,6,9-trimethyl-4-morpholino-6h-[1,4]oxazino[3,4-e]purin-2-yl)pyrimidin-2-amine 119

Step 1: methyl 2-(2-chloro-8-(2-hydroxypropan-2-yl)-6-morpholino-9H-purin-9-yl)propanoate

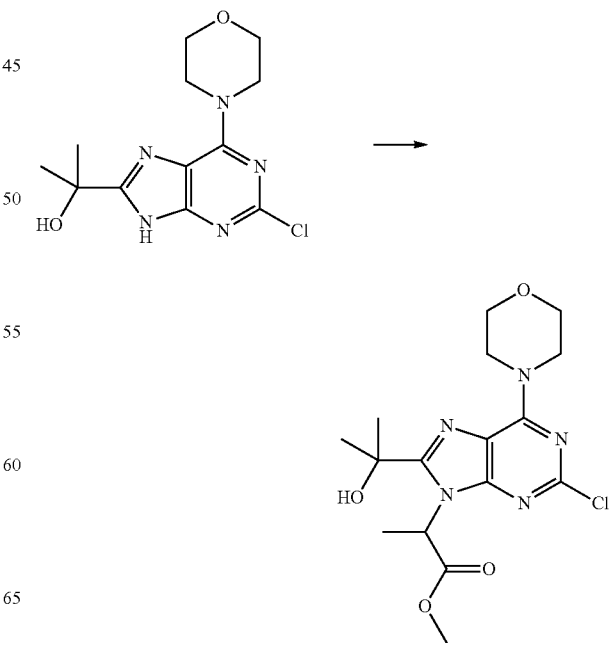

2-(2-chloro-6-morpholino-9H-purin-8-yl)propan-2-ol (4.6 g, 15 mmol) was dissolved in DMF (16 mL), treated with cesium carbonate (10 g, 31 mmol) and methyl 2-bromopropanoate (7.6 g, 46 mmol), and heated at 50° C. for 3 hr. Partial conversion prompted addition of cesium carbonate (10 g, 31 mmol) and methyl 2-bromopropanoate (7.6 g, 46 mmol) and the reaction mixture was heated at 50° C. for 20 hr. The reaction mixture was cooled to ambient temperature and diluted with water and ethyl acetate and the layers separated. The aqueous phase was extracted into ethyl acetate (3×), dried over sodium sulfate, filtered, and absorbed onto celite for purification by flash chromatography to afford methyl 2-(2-chloro-8-(2-hydroxypropan-2-yl)-6-morpholino-9H-purin-9-yl)propanoate as a yellow foam (1.6 g, 26%). LC/MS (ESI+): m/z 384 (M+H)

Step 2: 2-(2-chloro-8-(2-hydroxypropan-2-yl)-6-morpholino-9H-purin-9-yl)propanal

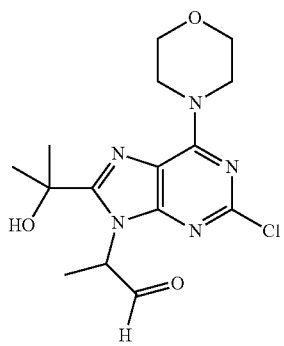

Methyl 2-(2-chloro-8-(2-hydroxypropan-2-yl)-6-morpholino-9H-purin-9-yl)propanoate (1.6 g, 4.1 mmol) was dissolved in THF (30 mL) and cooled to −78° C. The reaction mixture was treated with a 1.0M solution of lithium tetrahydroaluminate in THF (8.6 mL) and stirred at −78° C. for 1 hr. A saturated solution of NH4Cl was added and the mixture was diluted with DCM. The reaction mixture was treated with a saturated solution of Rochelle's salt and stirred on high at ambient temperature for 1 hr. The layers were separated and the aqueous phase was extracted into DCM/MeOH (3×), dried over sodium sulfate, filtered, and absorbed onto celite for purification by flash chromatography to afford 2-(2-chloro-8-(2-hydroxypropan-2-yl)-6-morpholino-9H-purin-9-yl)propanal as a white foam (900 mg, 62%). LC/MS (ESI+): m/z 384 (M+H)

Step 3: 2-chloro-6,6,9-trimethyl-4-morpholino-6H-[1,4]oxazino[3,4-e]purine

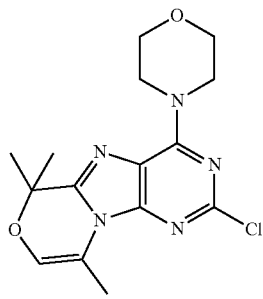

A solution of 2-(2-chloro-8-(2-hydroxypropan-2-yl)-6-morpholino-9H-purin-9-yl)propanal (900 mg, 2.5 mmol) in toluene (8.1 mL), was treated with trifluoroacetic acid (0.58 mL, 7.6 mmol) and heated at 110° C. for 4 hr. Partial conversion prompted addition of trifluoroacetic acid (1.0 mL) and the mixture was allowed to stir overnight at 110° C. The reaction mixture was cooled to ambient temperature and concentrated to dryness in vacuo. The resultant residue was re-dissolved in DCM and absorbed onto celite for purification by flash chromatography to afford 2-chloro-6,6,9-trimethyl-4-morpholino-6H-[1,4]oxazino[3,4-e]purine as a solid (190 mg, 22%). LC/MS (ESI+): m/z 336/338 (M+H)

Step 4: 2-chloro-6,6,9-trimethyl-4-morpholino-6H-[1,4]oxazino[3,4-e]purine (190 mg, 0.55 mmol), 5-(4,4,5,5-tetramethyl-1,3,2-dioxaborolan-2-yl)pyrimidin-2-amine (160 mg, 0.71 mmol), and tetrakis(triphenylphosphine)-palladium(0) (32 mg, 27 umol, 5.0 mol %) suspended in MeCN (1.3 mL) and 1.0M Na$_2$CO$_{3(aq)}$ (1.0 mL) was heated under microwave irradiation at 140° C. for 15 minutes. The cooled reaction mixture was concentrated to dryness in vacuo. The resultant residue was purified via HPLC to afford 119 as a white solid (120 mg, 54%). LC/MS (ESI+): m/z 395 (M+H). $^1$H NMR (400 MHz, DMSO) δ 9.06 (s, 2H), 7.03 (s, 2H), 6.34 (s, 1H), 4.24 (s, 4H), 3.80-3.70 (m, 4H), 2.52 (s, 3H), 1.62 (s, 6H). LCMS: R$_T$=4.57 min, M+H$^+$=395.2

Example 120

(R)-5-(6-ethyl-6-methyl-4-morpholino-8,9-dihydro-6H-[1,4]oxazino[3,4-e]purin-2-yl)pyrimidin-2-amine 120

Following the procedures of Example 118, the R-enantiomer 120 was isolated.

Example 121

5-(1-morpholin-4-yl-5,6,8a,9-tetrahydro-8h-7,10-dioxa-2,4,4b-triaza-phenanthren-3-yl)-pyrimidin-2-ylamine 121

Step 1: [4-(2,6-Dichloro-5-methoxy-pyrimidin-4-yl)-morpholin-3-yl]-methanol

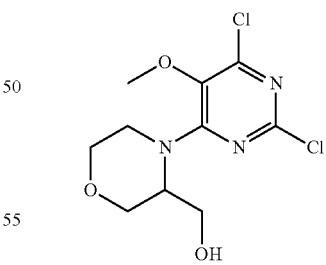

A mixture of 2,4,6-trichloro-5-methoxy-pyrimidine (1 g, 4.68 mmol), morpholin-3-yl-methanol hydrochloride (0.86 g, 5.6 mmol) and triethylamine (0.9 mL, 6.5 mmol) in IMS (30 mL) was stirred at RT for 3 h, then concentrated in vacuo. The resulting residue was purified by column chromatography (SiO$_2$, 0 to 50% ethyl acetate in cyclohexane) affording [4-(2,6-Dichloro-5-methoxy-pyrimidin-4-yl)-morpholin-3-yl]-methanol (614 mg, 45%). LCMS (method A): R$_T$=2.63 min, [M+H]$^+$=294/296.

Step 2: 1,3-Dichloro-5,6,8a,9-tetrahydro-8H-7,10-dioxa-2,4,4b-triaza-phenanthrene

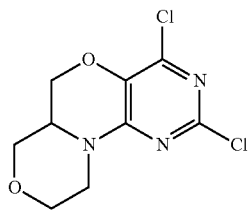

A mixture of [4-(2,6-dichloro-5-methoxy-pyrimidin-4-yl)-morpholin-3-yl]-methanol (614 mg, 2.09 mmol) and lithium chloride (246 mg, 5.80 mmol) in anhydrous DMF (5 mL) was heated at 160° C. for 10 mins in a microwave reactor, then concentrated in vacuo to give 2,4-dichloro-6-(3-hydroxymethyl-morpholin-4-yl)-pyrimidin-5-ol. DIAD (452 µL, 2.3 mmol) was added to a solution of 2,4-dichloro-6-(3-hydroxymethyl-morpholin-4-yl)-pyrimidin-5-ol (2 mmol) and triphenyl phosphine (603 mg, 2.3 mmol) in 1,4-dioxane (5 mL) and the mixture stirred at RT for 1 h, then concentrated in vacuo. The resulting residue was purified by column chromatography (SiO$_2$, 0 to 50% ethyl acetate in cyclohexane) affording 1,3-Dichloro-5,6,8a,9-tetrahydro-8H-7,10-dioxa-2,4,4b-triaza-phenanthrene (200 mg, 37%). LCMS (method A): R$_T$=2.91 min, [M+H]$^+$=262/264.

Step 3: 3-Chloro-1-morpholin-4-yl-5,6,8a,9-tetrahydro-8H-7,10-dioxa-2,4,4b-triaza-phenanthrene

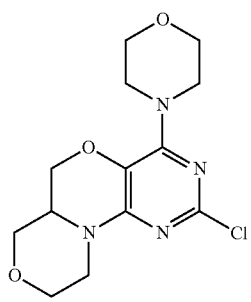

A mixture of 1,3-dichloro-5,6,8a,9-tetrahydro-8H-7,10-dioxa-2,4,4b-triaza-phenanthrene (100 mg, 0.38 mmol), morpholine (80 µL, 0.92 mmol) and triethylamine (70 µL, 0.50 mmol) in IMS (5 mL) was heated at 140° C. for 25 mins in a microwave reactor, then concentrated in vacuo. The resulting residue was purified by column chromatography (SiO$_2$, 0 to 10 to 15 to 25% ethyl acetate in pentane) affording 3-Chloro-1-morpholin-4-yl-5,6,8a,9-tetrahydro-8H-7,10-dioxa-2,4,4b-triaza-phenanthrene (45 mg, 38%). LCMS (method A): R$_T$=2.92 min, [M+H]$^+$=313. H NMR (400 MHz, CDCl$_3$): δ 4.37 (1H, dd, J=13.2, 3.0 Hz), 4.19 (1H, dd, J=10.8, 3.3 Hz), 3.99 (1H, dd, J=11.1, 3.9 Hz), 3.88 (1H, dd, J=10.8, 3.2 Hz), 3.80 (dd, J=11.1, 8.4 Hz), 3.75 (4H, m), 3.66-3.53 (6H, m), 3.24 (1H, t, J=11.1 Hz), 3.00 (1H, m).

Step 4: A mixture of 3-chloro-1-morpholin-4-yl-5,6,8a,9-tetrahydro-8H-7,10-dioxa-2,4,4b-triaza-phenanthrene (45 mg, 0.144 mmol), 5-(4,4,5,5-tetramethyl-[1,3,2]dioxaborolan-2-yl)-pyrimidin-2-ylamine (60 mg, 0.271 mmol), PdCl$_2$(PPh$_3$)$_2$ (10 mg, 0.014 mmol) and sodium carbonate (460 µL, 0.46 mmol, 1M aqueous solution) in acetonitrile (2 mL) was degassed and heated at 120° C. for 30 mins in a microwave reactor. The reaction mixture was loaded onto an Isolute® SCX-2 cartridge which was washed with methanol and the product eluted with 2M ammonia in methanol. The basic fractions were combined and concentrated in vacuo. The resulting residue was purified by reverse phase HPLC (Phenomenex Gemini 5 µm C18, 0.1% HCO$_2$H in water on a gradient acetonitrile 5-98%) affording 121 as a white solid (3 mg, 6%). LCMS (method B): R$_T$=3.08 min, [M+H]$^+$=372. $^1$H NMR (400 MHz, CDCl$_3$): δ 9.11 (2H, s), 5.18 (2H, broad s), 4.55 (1H, dd, J=13.5, 2.4 Hz), 4.22 (1H, dd, J=10.8, 3.1 Hz), 4.05 (1H, dd, J=11.5, 3.5 Hz), 3.88 (2H, m), 3.81 (4H, m), 3.69-3.56 (6H, m), 3.29 (1H, t, J=11.5 Hz), 3.02 (1H, m).

Example 122

5-((S)-6-Morpholin-4-yl-2,3,3a,4-tetrahydro-1H-5-oxa-7,9,9b-triaza-cyclopenta[a]naphthalen-8-yl)-pyrimidin-2-ylamine 122

Step 1: [(S)-1-(2,6-Dichloro-5-methoxy-pyrimidin-4-yl)-pyrrolidin-2-yl]-methanol

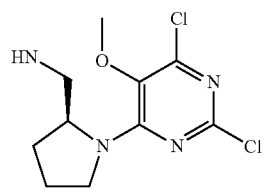

A mixture of 2,4,6-trichloro-5-methoxy-pyrimidine (1.2 g, 5.62 mmol), (S)-1-pyrrolidin-2-yl-methanol (1.1 mL, 11.3 mmol) and triethylamine (1.08 mL, 7.75 mmol) in IMS (36 mL) was stirred at RT for 20 mins, then concentrated in vacuo. The resulting residue was purified by column chromatography (SiO$_2$, 0 to 50% ethyl acetate in cyclohexane) affording [(S)-1-(2,6-Dichloro-5-methoxy-pyrimidin-4-yl)-pyrrolidin-2-yl]-methanol (1.08 mg, 70%). LCMS (method A): R$_T$=2.98 min, [M+H]$^+$=278/280.

Step 2: (S)-6,8-Dichloro-2,3,3a,4-tetrahydro-1H-5-oxa-7,9,9b-triaza-cyclopenta[a]naphthalene

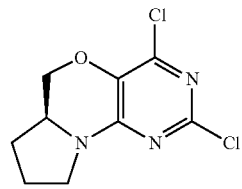

A mixture of [(S)-1-(2,6-dichloro-5-methoxy-pyrimidin-4-yl)-pyrrolidin-2-yl]-methanol (900 mg, 3.24 mmol) and lithium chloride (360 mg, 8.48 mmol) in anhydrous DMF (10 mL) was heated at 160° C. for 10 mins in a microwave reactor, then concentrated in vacuo to give 2,4-dichloro-6-((S)-2-hydroxymethyl-pyrrolidin-1-yl)-pyrimidin-5-ol. DIAD (700 µL, 3.56 mmol) was added to a solution of 2,4-dichloro-6-((S)-2-hydroxymethyl-pyrrolidin-1-yl)-pyrimidin-5-ol (3 mmol) and triphenyl phosphine (900 mg, 3.43 mmol) in 1,4-dioxane (10 mL) and the mixture stirred at RT for 1 h, then concentrated in vacuo. The resulting residue was purified by column chromatography (SiO$_2$, 0 to 20% ethyl acetate in cyclohexane) affording (S)-6,8-dichloro-2,3,3a,4-tetrahydro-1H-5-oxa-7,9,9b-triaza-cyclopenta[a]naphthalene. LCMS (method A): $R_T$=2.98 min, [M+H]$^+$=246/248.

Step 3: A mixture of (S)-6,8-dichloro-2,3,3a,4-tetrahydro-1H-5-oxa-7,9,9b-triaza-cyclopenta[a]naphthalene (290 mg, 1.18 mmol), morpholine (275 μL, 3.14 mmol) and triethylamine (242 μL, 1.74 mmol) in IMS (11 mL) was heated at 140° C. for 20 mins in a microwave reactor, then concentrated in vacuo. The resulting residue re-dissolved in acetonitrile (2 mL) and 5-(4,4,5,5-tetramethyl-[1,3,2]dioxaborolan-2-yl)-pyrimidin-2-ylamine (500 mg, 2.26 mmol), PdCl$_2$(PPh$_3$)$_2$ (88 mg, 0.125 mmol) and sodium carbonate (4 mL, 4.0 mmol, 1M aqueous solution) were added. The reaction mixture was degassed and heated at 120° C. for 30 mins in a microwave reactor. The reaction mixture was loaded onto an Isolute® SCX-2 cartridge which was washed with methanol and the product eluted with 2M ammonia in methanol. The basic fractions were combined and concentrated in vacuo. The resulting residue was purified by reverse phase HPLC (Phenomenex Gemini 5 μm C18, 0.1% HCO$_2$H in water gradient acetonitrile 5-60%) affording 122 as a white solid (30 mg, 8%). LCMS (method B): $R_T$=3.34 min, [M+H]$^+$=356. $^1$H NMR (400 MHz, CDCl$_3$): δ 9.15 (2H, s), 5.14 (2H, broad s), 4.48 (1H, dd, J=10.4, 3.5 Hz), 3.87-3.68 (10H, m), 3.62 (1H, m), 3.31 (1H, t, J=10.1 Hz), 2.21-1.94 (3H, m), 1.50 (1H, m).

Also isolated was the regioisomer, 5-((S)-8-morpholin-4-yl-2,3,3a,4-tetrahydro-1H-5-oxa-7,9,9b-triaza-cyclopenta[a]romoacetyl-6-yl)-pyrimidin-2-ylamine (25 mg, 6%). LCMS (method B): $R_T$=2.47 min, [M+H]$^+$=356. $^1$H NMR (400 MHz, CDCl$_3$): δ 9.09 (2H, s), 5.14 (2H, broad s), 4.49 (1H, dd, J=10.8, 3.8 Hz), 3.80-3.65 (10H, m), 3.66 (1H, m), 3.34 (1H, t, J=9.7 Hz), 2.20-1.94 (3H, m), 1.48 (1H, m).

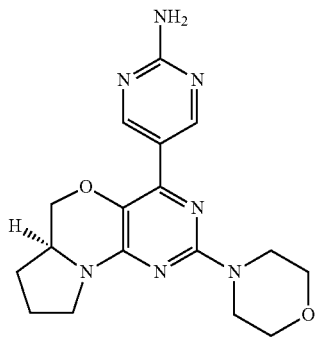

Example 123

4-(6,6-dimethyl-4-morpholino-8,9-dihydro-6h-[1,4]oxazino[3,4-e]purin-2-yl)aniline 123

To 2-chloro-6,6-dimethyl-4-morpholino-8,9-dihydro-6H-[1,4]oxazino[3,4-e]purine from Example 103 and following General Procedure A (266 mg, 0.82 mmol) in acetonitrile (2.5 mL) was added 4-aminophenylboronic acid, pinacol ester (270 mg, 1.2 mmol) and 1.0 M of cesium carbonate in water (2.5 mL). The reaction mixture was degassed for 5 min and recycled with nitrogen atmosphere. Subsequently, bis(di-tert-butyl(4-dimethylaminophenyl)phosphine)palladium(II) dichloride (29 mg, 0.041 mmol) was added, and the mixture was degassed and recycled again. The reaction vial was then subjected to microwave irradiation for 25 mins at 100° C. The vessel was cooled to room temperature and extracted twice with EtOAc. Dried over MgSO$_4$, filtered and concentrated in vacuo. Purified by rp-HPLC to provide 123 (151 mg, 48% yield). MS (ESI+): m/z 381.2 (M+H$^+$). $^1$H NMR (400 MHz, DMSO) δ 8.08 (d, J=8.5 Hz, 1H), 6.59 (d, J=8.5 Hz, 1H), 5.42 (s, 1H), 4.22 (s, 2H), 4.11 (s, 2H), 3.80-3.67 (m, 2H), 1.57 (s, 3H)

Example 124

1-(4-(6,6-dimethyl-4-morpholino-8,9-dihydro-6h-[1,4]oxazino[3,4-e]purin-2-yl)phenyl)-3-methylurea 124

To a solution of 4-(6,6-dimethyl-4-morpholino-8,9-dihydro-6H-[1,4]oxazino[3,4-e]purin-2-yl)aniline 123 (0.44 g, 1.2 mmol) in 1,2-dichloroethane (10 mL) was added triethylamine (0.35 mL, 2.5 mmol) and the reaction mixture was cooled to 0° C. Triphosgene (0.17 g, 0.57 mmol) was added slowly and the mixture was subsequently warmed to 70° C. for 1 h. The reaction mixture was then cooled to room temperature for the addition of 2.0 M of methylamine in THF (2.2 mL, 4.4 mmol) and the resulting reaction mixture was stirred for 16 h at ambient temperature. LC-MS indicated complete conversion and as a result the reaction mixture was diluted with water and EtOAc. The phases were separated and the aqueous layer was extracted 3× with EtOAc. The organic extracts were collected and dried over MgSO$_4$, filtered and concentrated in vacuo. Purified by rp-HPLC to provide 124 (122 mg, 25% yield). MS (ESI+): m/z 438.2 (M+H$^+$). $^1$H NMR (400 MHz, DMSO) δ 8.68 (s, 1H), 8.24 (d, J=8.7 Hz, 2H), 7.48 (d, J=8.7 Hz, 2H), 6.04 (q, J=4.4 Hz, 1H), 4.25 (s, 4H), 4.14 (d, J=3.4 Hz, 4H), 3.82-3.67 (m, 4H), 2.66 (d, J=4.6 Hz, 3H), 1.58 (s, 6H)

Example 125

6,6-dimethyl-4-morpholino-2-(1H-pyrazol-4-yl)-8,9-dihydro-6H-[1,4]oxazino[3,4-e]purine 125

Following General Procedure A, 2-chloro-6,6-dimethyl-4-morpholino-8,9-dihydro-6H-[1,4]oxazino[3,4-e]purine (102 mg, 0.31 mmol), 4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 125. 1H NMR (400 MHz, DMSO) δ 12.98 (s, 1H), 8.23 (s, 1H), 8.01 (s, 1H), 4.22 (s, 4H), 4.10 (s, 4H), 3.80-3.67 (m, 4H), 1.57 (s, 6H). LCMS: $R_T$=3.67 min, M+H$^+$=356

Example 126

4-(6,6-dimethyl-4-morpholino-8,9-dihydro-6H-[1,4]oxazino[3,4-e]purin-2-yl)pyridin-2-amine 126

Following General Procedure A, 2-chloro-6,6-dimethyl-4-morpholino-8,9-dihydro-6H-[1,4]oxazino[3,4-e]purine (102 mg, 0.31 mmol), 4-(4,4,5,5-tetramethyl-1,3,2-dioxaborolan-2-yl)romoace-2-amine (0.31 mmole), and bis(di-tert-butyl(4-dimethylaminophenyl)phosphine)dichloropalladium (II) (11 mg, 16 umol) were reacted to give 126. 1H NMR (400 MHz, DMSO) δ 7.99 (d, J=5.3 Hz, 1H), 7.41 (s, 1H), 7.38 (d, J=5.3 Hz, 1H), 5.97 (s, 2H), 4.27 (s, 4H), 4.15 (d, J=3.5 Hz, 4H), 3.82-3.71 (m, 4H), 1.59 (s, 6H). LCMS: $R_T$=3.64 min, M+H$^+$=382

Example 127

6,6-dimethyl-2-(1-methyl-1H-pyrazol-4-yl)-4-morpholino-8,9-dihydro-6H-[1,4]oxazino[3,4-e]purine 127

Following General Procedure A, 2-chloro-6,6-dimethyl-4-morpholino-8,9-dihydro-6H-[1,4]oxazino[3,4-e]purine (102 mg, 0.31 mmol), 1-methyl-4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 127. 1H NMR (400 MHz, DMSO) δ 8.23 (s, 1H), 7.93 (s, 1H), 4.21 (s, 4H), 4.10 (s, 4H), 3.88 (s, 3H), 3.73 (dd, J=12.3, 7.7 Hz, 4H), 1.57 (s, 6H). LCMS: $R_T$=3.94 min, M+H$^+$=370

Example 128

3-(6,6-dimethyl-4-morpholino-8,9-dihydro-6H-[1,4]oxazino[3,4-e]purin-2-yl)phenol 128

Following General Procedure A, 2-chloro-6,6-dimethyl-4-morpholino-8,9-dihydro-6H-[1,4]oxazino[3,4-e]purine (102 mg, 0.31 mmol), 3-(4,4,5,5-tetramethyl-1,3,2-dioxaborolan-2-yl)phenol (0.31 mmole), and bis(di-tert-butyl(4-dimethylaminophenyl)phosphine)dichloropalladium (II) (11 mg, 16 umol) were reacted to give 128. 1H NMR (400 MHz, DMSO) δ 9.41 (s, 1H), 7.82 (dd, J=4.5, 2.5 Hz, 2H), 7.28-7.20 (m, 1H), 6.82 (dd, J=7.7, 1.8 Hz, 1H), 4.26 (s, 4H), 4.19-4.08 (m, 4H), 3.82-3.71 (m, 4H), 1.59 (s, 6H). LCMS: $R_T$=4.46 min, M+H$^+$=382

Example 129

2-(1H-indazol-5-yl)-6,6-dimethyl-4-morpholino-8,9-dihydro-6H-[1,4]oxazino[3,4-e]purine 129

Following General Procedure A, 2-chloro-6,6-dimethyl-4-morpholino-8,9-dihydro-6H-[1,4]oxazino[3,4-e]purine (102 mg, 0.31 mmol), 5-(4,4,5,5-tetramethyl-1,3,2-dioxaborolan-2-yl)-1H-indazole (0.31 mmole), and bis(di-tert-butyl(4-dimethylaminophenyl)phosphine)dichloropalladium (II) (11 mg, 16 umol) were reacted to give 129. 1H NMR (400 MHz, DMSO) δ 13.11 (s, 1H), 8.81 (s, 1H), 8.48-8.43 (m, 1H), 8.19 (s, 1H), 7.58 (d, J=8.8 Hz, 1H), 4.29 (s, 4H), 4.17 (dd, J=16.1, 5.1 Hz, 4H), 3.82-3.74 (m, 4H), 1.60 (s, 6H). LCMS: $R_T$=4.47 min, M+H$^+$=406

Example 130

6,6-dimethyl-2-(2-(4-methylpiperazin-1-yl)romoace-4-yl)-4-morpholino-8,9-dihydro-6H-[1,4]oxazino[3,4-e]purine 130

Following General Procedure A, 2-chloro-6,6-dimethyl-4-morpholino-8,9-dihydro-6H-[1,4]oxazino[3,4-e]purine (102 mg, 0.31 mmol), 1-methyl-4-(4-(4,4,5,5-tetramethyl-1,3,2-dioxaborolan-2-yl)romoace-2-yl)piperazine (0.31 mmole), and bis(di-tert-butyl(4-dimethylaminophenyl)phosphine)dichloropalladium (II) (11 mg, 16 umol) were reacted to give 130. 1H NMR (400 MHz, DMSO) δ 8.21 (d, J=4.7 Hz, 1H), 7.68 (d, J=4.7 Hz, 1H), 4.27 (s, 4H), 4.16 (d, J=26.1 Hz, 4H), 3.77 (s, 4H), 3.55 (s, 4H), 2.46 (s, 4H), 2.25 (s, 3H), 1.59 (s, 6H). LCMS: $R_T$=3.40 min, M+H$^+$=465

Example 131

N-(2-(6,6-dimethyl-4-morpholino-8,9-dihydro-6H-[1,4]oxazino[3,4-e]purin-2-yl)phenyl)methanesulfonamide 131

Following General Procedure A, 2-chloro-6,6-dimethyl-4-morpholino-8,9-dihydro-6H-[1,4]oxazino[3,4-e]purine (102 mg, 0.31 mmol), N-(2-(4,4,5,5-tetramethyl-1,3,2-dioxaborolan-2-yl)phenyl)methanesulfonamide (0.31 mmole), and bis(di-tert-butyl(4-dimethylaminophenyl)phosphine)dichloropalladium (II) (11 mg, 16 umol) were reacted to give 131. 1H NMR (400 MHz, DMSO) δ 12.87 (s, 1H), 8.58 (d, J=8.0 Hz, 1H), 7.60 (d, J=8.1 Hz, 1H), 7.48 (t, J=7.5 Hz, 1H), 7.22 (t, J=7.4 Hz, 1H), 4.26 (s, 4H), 4.16 (s, 4H), 3.78 (s, 4H), 3.07 (s, 3H), 1.62 (d, J=11.5 Hz, 6H). LCMS: $R_T$=5.36 min, M+H$^+$=459

Example 132

6,6-dimethyl-4-morpholino-2-(6-morpholinopyridin-3-yl)-8,9-dihydro-6H-[1,4]oxazino[3,4-e]purine 132

Following General Procedure A, 2-chloro-6,6-dimethyl-4-morpholino-8,9-dihydro-6H-[1,4]oxazino[3,4-e]purine (102 mg, 0.31 mmol), 4-(5-(4,4,5,5-tetramethyl-1,3,2-dioxaborolan-2-yl)romoace-2-yl)morpholine (0.31 mmole), and bis(di-tert-butyl(4-dimethylaminophenyl)phosphine)dichloropalladium (II) (11 mg, 16 umol) were reacted to give 132. 1H NMR (400 MHz, DMSO) δ 9.11 (s, 1H), 8.42 (d, J=8.7 Hz, 1H), 6.89 (d, J=8.9 Hz, 1H), 4.24 (s, 4H), 4.14 (s, 4H), 3.74 (d, J=14.7 Hz, 8H), 3.55 (d, J=3.9 Hz, 4H), 1.60 (d, J=15.6 Hz, 6H). LCMS: $R_T$=3.79 min, M+H$^+$=452

Example 133

2-(1-benzyl-1H-pyrazol-4-yl)-6,6-dimethyl-4-morpholino-8,9-dihydro-6H-[1,4]oxazino[3,4-e]purine 133

Following General Procedure A, 2-chloro-6,6-dimethyl-4-morpholino-8,9-dihydro-6H-[1,4]oxazino[3,4-e]purine (102 mg, 0.31 mmol), 1-benzyl-4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 133. 1H NMR (400 MHz, DMSO) δ 8.37 (s, 1H), 7.99 (s, 1H), 7.35 (d, J=7.6 Hz, 2H), 7.29 (d, J=6.9 Hz, 3H), 5.37 (s, 2H), 4.21 (s, 4H), 4.09 (s, 4H), 3.74 (s, 4H), 1.58 (d, J=9.4 Hz, 6H). LCMS: $R_T$=4.82 min, M+H$^+$=446

Example 134

2-(2-isopropoxypyridin-3-yl)-6,6-dimethyl-4-morpholino-8,9-dihydro-6H-[1,4]oxazino[3,4-e]purine 134

Following General Procedure A, 2-chloro-6,6-dimethyl-4-morpholino-8,9-dihydro-6H-[1,4]oxazino[3,4-e]purine (102 mg, 0.31 mmol), 2-isopropoxy-3-(4,4,5,5-tetramethyl-1,3,2-dioxaborolan-2-yl)pyridine (0.31 mmole), and bis(di-tert-butyl(4-dimethylaminophenyl)phosphine)dichloropalladium (II) (11 mg, 16 umol) were reacted to give 134. 1H NMR (400 MHz, DMSO) δ 8.20 (s, 1H), 8.03 (d, J=7.2 Hz, 1H), 7.07-6.99 (m, 1H), 5.43-5.31 (m, 1H), 4.22 (s, 4H), 4.11 (s, 4H), 3.73 (s, 4H), 1.59 (s, 6H), 1.26 (d, J=6.1 Hz, 6H). LCMS: $R_T$=4.56 min, M+H$^+$=425

Example 135

N-(2-(6,6-dimethyl-4-morpholino-8,9-dihydro-6H-[1,4]oxazino[3,4-e]purin-2-yl)phenyl)acetamide 135

Following General Procedure A, 2-chloro-6,6-dimethyl-4-morpholino-8,9-dihydro-6H-[1,4]oxazino[3,4-e]purine (102 mg, 0.31 mmol), N-(2-(4,4,5,5-tetramethyl-1,3,2-dioxaborolan-2-yl)phenyl)acetamide (0.31 mmole), and bis(di-tert-butyl(4-dimethylaminophenyl)phosphine)dichloropalladium (II) (11 mg, 16 umol) were reacted to give 135. 1H NMR (400 MHz, DMSO) δ 12.45 (s, 1H), 8.53 (d, J=8.2 Hz, 1H), 8.44 (d, J=8.2 Hz, 1H), 7.40 (t, J=7.5 Hz, 1H), 7.15 (t, J=7.5 Hz, 1H), 4.23 (t, J=18.4 Hz, 4H), 4.16 (s, 2H), 3.78 (s, 4H), 2.21 (s, 3H), 1.62 (d, J=10.6 Hz, 6H). LCMS: $R_T$=5.16 min, M+H$^+$=423

Example 136

2-(3,5-dimethyl-1H-pyrazol-4-yl)-6,6-dimethyl-4-morpholino-8,9-dihydro-6H-[1,4]oxazino[3,4-e]purine 136

Following General Procedure A, 2-chloro-6,6-dimethyl-4-morpholino-8,9-dihydro-6H-[1,4]oxazino[3,4-e]purine (102 mg, 0.31 mmol), 3,5-dimethyl-4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 136. LCMS: $R_T$=3.81 min, M+H$^+$=384

Example 137

5-(6,6-dimethyl-4-morpholino-8,9-dihydro-6H-[1,4]oxazino[3,4-e]purin-2-yl)romoace-2-ol 137

Following General Procedure A, 2-chloro-6,6-dimethyl-4-morpholino-8,9-dihydro-6H-[1,4]oxazino[3,4-e]purine (102 mg, 0.31 mmol), 5-(4,4,5,5-tetramethyl-1,3,2-dioxaborolan-2-yl)romoace-2-ol (0.31 mmole), and bis(di-tert-butyl(4-dimethylaminophenyl)phosphine)dichloropalladium (II) (11 mg, 16 umol) were reacted to give 137. 1H NMR (400 MHz, DMSO) δ 11.82 (s, 1H), 8.34 (d, J=9.7 Hz, 1H), 8.27 (s, 1H), 6.41 (d, J=9.6 Hz, 1H), 4.22 (s, 4H), 4.12 (s, 4H), 3.75 (s, 4H), 1.57 (s, 6H). LCMS: $R_T$=3.95 min, M+H$^+$=383

Example 138

6-(6,6-dimethyl-4-morpholino-8,9-dihydro-6H-[1,4]oxazino[3,4-e]purin-2-yl)romoace-3-amine 138

Following General Procedure A, 2-chloro-6,6-dimethyl-4-morpholino-8,9-dihydro-6H-[1,4]oxazino[3,4-e]purine (102 mg, 0.31 mmol), 6-(4,4,5,5-tetramethyl-1,3,2-dioxaborolan-2-yl)romoace-3-amine (0.31 mmole), and bis(di-tert-butyl(4-dimethylaminophenyl)phosphine)dichloropalladium (II) (11 mg, 16 umol) were reacted to give 138. 1H NMR (400 MHz, DMSO) δ 9.20 (s, 1H), 8.91 (s, 1H), 8.22 (d, J=8.4 Hz, 1H), 8.07 (d, J=3.8 Hz, 1H), 7.25 (dd, J=8.1, 4.3 Hz, 1H), 4.25-3.97 (m, 8H), 3.74 (d, J=3.9 Hz, 4H), 1.55 (s, 6H). LCMS: $R_T$=3.44 min, M+H$^+$=382

Examples 139 and 140

(R)-5-(4-morpholino-6-(trifluoromethyl)-8,9-dihydro-6H-[1,4]oxazino[3,4-e]purin-2-yl)pyrimidin-2-amine 139 and (S)-5-(4-morpholino-6-(trifluoromethyl)-8,9-dihydro-6H-[1,4]oxazino[3,4-e]purin-2-yl)pyrimidin-2-amine 140

Step 1: 1-(2-chloro-6-morpholino-9-(tetrahydro-2H-pyran-2-yl)-9H-purin-8-yl)-2,2,2-trifluoroethanone

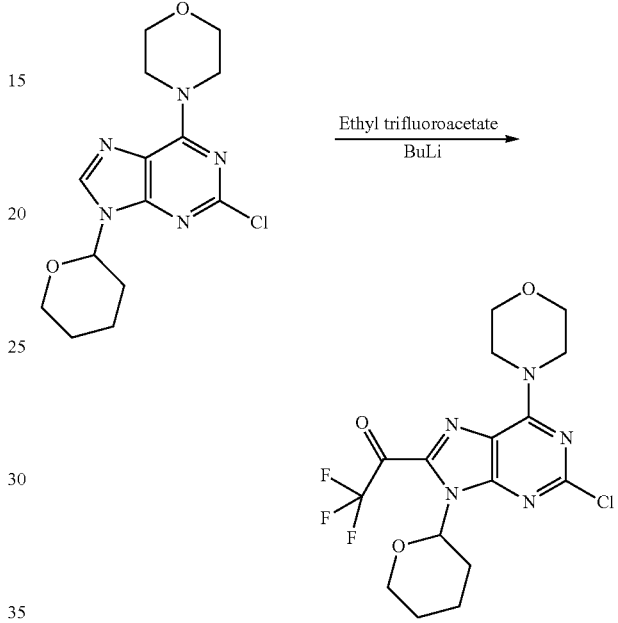

To a mixture of 4-(2-chloro-9-(tetrahydro-2H-pyran-2-yl)-9H-purin-6-yl)morpholine (1 g, 9 mmol) in THF (25 mL) at −78° C. was added Tetramethylethylenediamine (0.93 mL, 0.0062 mol) followed by 2.5 M of n-BuLi (2.5 mL, 0.0062 mol) dropwise. The reaction was stirred at −78° C. for 30 minutes and then ethyl trifluoroacetate (0.74 mL, 0.0062 mol) was added, continue stirred for 2 hours at −78° C. The reaction was quenched with water and extracted with EtOAc. The organic extracts were washed with water, brine, dried over MgSO$_4$ and concentrated. The crude material was purified by ISCO with 0-100% EtOAc/hexane to give pure 1-(2-chloro-6-morpholino-9-(tetrahydro-2H-pyran-2-yl)-9H-purin-8-yl)-2,2,2-trifluoroethanone as a white solid (2.5 g, 70% yield). LC/MS (ESI+): m/z 421 (M+H)

Step 2: 1-(2-chloro-6-morpholino-9-(tetrahydro-2H-pyran-2-yl)-9H-purin-8-yl)-2,2,2-trifluoroethanol

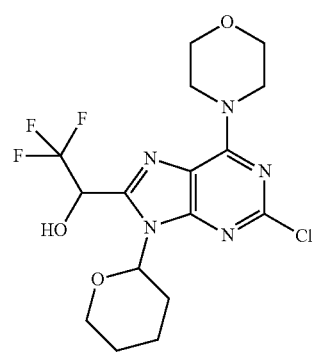

1-(2-Chloro-6-morpholino-9-(tetrahydro-2H-pyran-2-yl)-9H-purin-8-yl)-2,2,2-trifluoroethanone (1.5 g, 0.0036 mol) in MeOH (22 mL) was treated with sodium tetrahydroborate (0.27 g, 0.0072 mol), and stirred at room temperature for 1 hour. The reaction was quenched with water and extracted with EtOAc. The organic extracts were washed with water, brine, dried over MgSO₄ and concentrated. The crude material was purified with ISCO with 0-80% EtOAc/hexane to give the pure 1-(2-chloro-6-morpholino-9-(tetrahydro-2H-pyran-2-yl)-9H-purin-8-yl)-2,2,2-trifluoroethanol (1.3 g, 86% yield). LC/MS (ESI+): m/z 423 (M+H)

Step 3: 1-(2-chloro-6-morpholino-9H-purin-8-yl)-2,2,2-trifluoroethanol

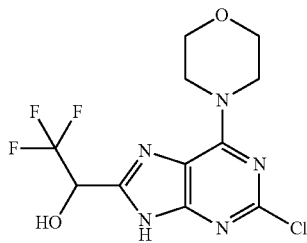

1-(2-Chloro-6-morpholino-9-(tetrahydro-2H-pyran-2-yl)-9H-purin-8-yl)-2,2,2-trifluoroethanol (1.3 g, 0.0031 mol) in MeOH (12 mL) was treated with cat. amount of p-toluenesulfonic acid (53 mg, 0.00031 mol). The reaction mixture was heated to 50° C. overnight and was then concentrated under reduce pressure. The residue was partitioned between water and EtOAc. The organic extracts were washed with water, brine, dried over MgSO₄ and concentrated to dryness to give 1-(2-chloro-6-morpholino-9H-purin-8-yl)-2,2,2-trifluoroethanol (1 g, 100% yield). LC/MS (ESI+): m/z 338 (M+H)

Step 4: 2-chloro-4-morpholino-6-(trifluoromethyl)-8,9-dihydro-6H-[1,4]oxazino[3,4-e]purine

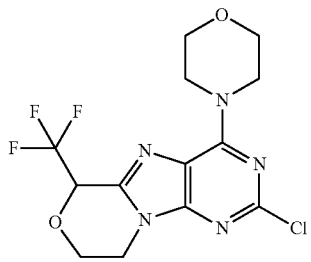

A mixture of 1-(2-chloro-6-morpholino-9H-purin-8-yl)-2,2,2-trifluoroethanol (1 g, 0.003 mol), 1,2-dibromoethane (0.51 mL, 0.006 mol) and cesium carbonate (2.9 g, 0.089 mol) in DMF (18 mL) was heated at 90° C. for 12 hours. The reaction mixture was filtered and partitioned between water and EtOAc. The organic extracts were washed with water, brine and dried over MgSO₄ and concentrated. The crude product was purified by isco with 0-50% EtOAc/hexane to give the pure 2-chloro-4-morpholino-6-(trifluoromethyl)-8,9-dihydro-6H-[1,4]oxazino[3,4-e]purine (0.3 g, 30%). LC/MS (ESI+): m/z 364 (M+H)

Step 5: 2-Chloro-4-morpholino-6-(trifluoromethyl)-8,9-dihydro-6H-[1,4]oxazino[3,4-e]purine (140 mg, 0.0004 mol) and 5-(4,4,5,5-tetramethyl-1,3,2-dioxaborolan-2-yl)pyrimidin-2-amine (130 mg, 0.00058 mol) were reacted under microwave Suzuki palladium conditions to give the racemic 5-(4-morpholino-6-(trifluoromethyl)-8,9-dihydro-6H-[1,4]oxazino[3,4-e]purin-2-yl)pyrimidin-2-amine (36 mg, 32% yield) which was separated into the (R) enantiomer 139 and the (S) enantiomer 140. LC/MS (ESI+): m/z 423 (M+H). ¹H NMR (400 MHz, DMSO) δ 9.11 (s, 2H), 7.05 (s, 2H), 5.88 (d, J=6.8 Hz, 1H), 4.38 (t, J=12.2 Hz, 2H), 4.35-4.09 (m, 6H), 3.76 (s, 4H)

Example 141

2-(1-ethyl-1H-pyrazol-4-yl)-6,6-dimethyl-4-morpholino-8,9-dihydro-6H-[1,4]oxazino[3,4-e]purine 141

Following General Procedure A, 2-chloro-6,6-dimethyl-4-morpholino-8,9-dihydro-6H-[1,4]oxazino[3,4-e]purine (102 mg, 0.31 mmol), 1-ethyl-4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 141. 1H NMR (400 MHz, DMSO) δ 8.26 (s, 1H), 7.95 (s, 1H), 4.28-4.12 (m, 6H), 4.10 (s, 4H), 3.78-3.69 (m, 4H), 1.58 (s, 6H), 1.40 (t, J=7.3 Hz, 3H). LCMS: R$_T$=4.13 min, M+H⁺=384

Example 142

4-(6,6-dimethyl-4-morpholino-8,9-dihydro-6H-[1,4]oxazino[3,4-e]purin-2-yl)-N,N-dimethylbenzamide 142

Following General Procedure A, 2-chloro-6,6-dimethyl-4-morpholino-8,9-dihydro-6H-[1,4]oxazino[3,4-e]purine (102 mg, 0.31 mmol), N,N-dimethyl-4-(4,4,5,5-tetramethyl-1,3,2-dioxaborolan-2-yl)benzamide (0.31 mmole), and bis(di-tert-butyl(4-dimethylaminophenyl)phosphine)dichloropalladium (II) (11 mg, 16 umol) were reacted to give 142. 1H NMR (400 MHz, DMSO) δ 8.42 (d, J=8.2 Hz, 2H), 7.49 (d, J=8.2 Hz, 2H), 4.28 (s, 4H), 4.16 (m, 4H), 3.81-3.73 (m, 4H), 3.06-2.87 (m, 6H), 1.60 (s, 6H). LCMS: R$_T$=4.60 min, M+H⁺=437

Example 143 tert-butyl 4-(6,6-dimethyl-4-morpholino-8,9-dihydro-6H-[1,4]oxazino[3,4-e]purin-2-yl)phenyl(methyl)carbamate 143

Following General Procedure A, 2-chloro-6,6-dimethyl-4-morpholino-8,9-dihydro-6H-[1,4]oxazino[3,4-e]purine (102 mg, 0.31 mmol), tert-butyl methyl(4-(4,4,5,5-tetramethyl-1,3,2-dioxaborolan-2-yl)phenyl)carbamate (0.31 mmole), and bis(di-tert-butyl(4-dimethylaminophenyl)phosphine)dichloropalladium (II) (11 mg, 16 umol) were reacted to give 143. LCMS: R$_T$=6.07 min, M+H⁺=495

Example 144

2-(3-(6,6-dimethyl-4-morpholino-8,9-dihydro-6H-[1,4]oxazino[3,4-e]purin-2-yl)phenyl)acetonitrile 144

Following General Procedure A, 2-chloro-6,6-dimethyl-4-morpholino-8,9-dihydro-6H-[1,4]oxazino[3,4-e]purine (102 mg, 0.31 mmol), 2-(3-(4,4,5,5-tetramethyl-1,3,2-dioxaborolan-2-yl)phenyl)acetonitrile (0.31 mmole), and bis(di-tert-butyl(4-dimethylaminophenyl)phosphine)dichloropalladium (II) (11 mg, 16 umol) were reacted to give 144. 1H NMR (400 MHz, DMSO) δ 8.37 (s, 1H), 8.35 (d, J=7.8 Hz, 1H), 7.50 (t, J=7.6 Hz, 1H), 7.43 (d, J=7.5 Hz, 1H), 4.28 (s, 4H), 4.21-4.11 (m, 6H), 3.84-3.70 (m, 4H), 1.59 (s, 6H). LCMS: $R_T$=5.11 min, M+H$^+$=405

Example 145

6,6-dimethyl-4-morpholino-2-(3-morpholinophenyl)-8,9-dihydro-6H-[1,4]oxazino[3,4-e]purine 145

Following General Procedure A, 2-chloro-6,6-dimethyl-4-morpholino-8,9-dihydro-6H-[1,4]oxazino[3,4-e]purine (102 mg, 0.31 mmol), 4-(3-(4,4,5,5-tetramethyl-1,3,2-dioxaborolan-2-yl)phenyl)morpholine (0.31 mmole), and bis(di-tert-butyl(4-dimethylaminophenyl)phosphine)dichloropalladium (II) (11 mg, 16 umol) were reacted to give 145. 1H NMR (400 MHz, DMSO) δ 7.96 (s, 1H), 7.86 (d, J=7.7 Hz, 1H), 7.32 (t, J=7.9 Hz, 1H), 7.04 (dd, J=8.1, 2.2 Hz, 1H), 4.25 (s, 4H), 4.15 (m, 4H), 3.77 (m, 8H), 3.21-3.12 (m, 4H), 1.59 (s, 6H). LCMS: $R_T$=4.66 min, M+H$^+$=451

Example 146

6,6-dimethyl-4-morpholino-2-(3-(morpholinomethyl)phenyl)-8,9-dihydro-6H-[1,4]oxazino[3,4-e]purine 146

Following General Procedure A, 2-chloro-6,6-dimethyl-4-morpholino-8,9-dihydro-6H-[1,4]oxazino[3,4-e]purine (102 mg, 0.31 mmol), 4-(3-(4,4,5,5-tetramethyl-1,3,2-dioxaborolan-2-yl)benzyl)morpholine (0.31 mmole), and bis(di-tert-butyl(4-dimethylaminophenyl)phosphine)dichloropalladium (II) (11 mg, 16 umol) were reacted to give 146. 1H NMR (400 MHz, DMSO) δ 8.30 (s, 1H), 8.27 (d, J=7.3 Hz, 1H), 7.46-7.34 (m, 2H), 4.27 (s, 4H), 4.16 (m, 4H), 3.83-3.72 (m, 4H), 3.58 (m, 4H), 3.55 (s, 2H), 2.38 (m, 4H), 1.59 (s, 6H). LCMS: $R_T$=3.84 min, M+H$^+$=465

Example 147

2-(3-(benzyloxy)phenyl)-6,6-dimethyl-4-morpholino-8,9-dihydro-6H-[1,4]oxazino[3,4-e]purine 147

Following General Procedure A, 2-chloro-6,6-dimethyl-4-morpholino-8,9-dihydro-6H-[1,4]oxazino[3,4-e]purine (102 mg, 0.31 mmol), 2-(3-(benzyloxy)phenyl)-4,4,5,5-tetramethyl-1,3,2-dioxaborolane (0.31 mmole), and bis(di-tert-butyl(4-dimethylaminophenyl)phosphine)dichloropalladium (II) (11 mg, 16 umol) were reacted to give 147. 1H NMR (400 MHz, DMSO) δ 8.00-7.94 (m, 2H), 7.50 (d, J=7.2 Hz, 2H), 7.44-7.37 (m, 3H), 7.37-7.30 (m, 1H), 7.14-7.07 (m, 1H), 5.20 (s, 2H), 4.21 (s, 4H), 4.15 (m, 4H), 3.82-3.69 (m, 4H), 1.59 (s, 6H). LCMS: $R_T$=6.33 min, M+H$^+$=472

Example 148

2-(1-isobutyl-1H-pyrazol-4-yl)-6,6-dimethyl-4-morpholino-8,9-dihydro-6H-[1,4]oxazino[3,4-e]purine 148

Following General Procedure A, 2-chloro-6,6-dimethyl-4-morpholino-8,9-dihydro-6H-[1,4]oxazino[3,4-e]purine (102 mg, 0.31 mmol), 1-isobutyl-4-(4,4,5,5-tetramethyl-1,3,2-dioxaborolan-2-yl)-1H-pyrazole (0.31 mmole), and bis(di-tert-butyl(4-dimethylaminophenyl)phosphine)dichloropalladium (II) (11 mg, 16 umol) were reacted to give 148. 1H NMR (400 MHz, DMSO) δ 8.24 (s, 1H), 7.95 (d, J=8.5 Hz, 1H), 4.22 (s, 4H), 4.10 (s, 4H), 3.95 (d, J=7.2 Hz, 2H), 3.78-3.69 (m, 4H), 2.15 (dp, J=13.8, 6.8 Hz, 1H), 1.57 (s, 6H), 0.86 (d, J=6.7 Hz, 6H). LCMS: $R_T$=4.67 min, M+H$^+$=412

Example 149

6,6-dimethyl-2-(6-(4-methylpiperazin-1-yl)romoace-3-yl)-4-morpholino-8,9-dihydro-6H-[1,4]oxazino[3,4-e]purine 149

Following General Procedure A, 2-chloro-6,6-dimethyl-4-morpholino-8,9-dihydro-6H-[1,4]oxazino[3,4-e]purine (102 mg, 0.31 mmol), 1-methyl-4-(5-(4,4,5,5-tetramethyl-1,3,2-dioxaborolan-2-yl)romoace-2-yl)piperazine (0.31 mmole), and bis(di-tert-butyl(4-dimethylaminophenyl)phosphine)dichloropalladium (II) (11 mg, 16 umol) were reacted to give 149. 1H NMR (400 MHz, DMSO) δ 9.08 (d, J=2.3 Hz, 1H), 8.39 (dd, J=9.0, 2.3 Hz, 1H), 6.89 (t, J=7.1 Hz, 1H), 4.24 (s, 4H), 4.14 (t, J=5.2 Hz, 4H), 3.81-3.70 (m, 4H), 3.64-3.52 (m, 4H), 2.44-2.36 (m, 4H), 2.23 (s, 3H), 1.58 (s, 6H). LCMS: $R_T$=3.45 min, M+H$^+$=465

Example 150

2-(1H-indazol-4-yl)-6,6-dimethyl-4-morpholino-8,9-dihydro-6H-[1,4]oxazino[3,4-e]purine 150

Following General Procedure A, 2-chloro-6,6-dimethyl-4-morpholino-8,9-dihydro-6H-[1,4]oxazino[3,4-e]purine (102 mg, 0.31 mmol), 4-(4,4,5,5-tetramethyl-1,3,2-dioxaborolan-2-yl)-1H-indazole 24 (0.31 mmole), and bis(di-tert-butyl(4-dimethylaminophenyl)phosphine)dichloropalladium (II) (11 mg, 16 umol) were reacted to give 150. 1H NMR (400 MHz, DMSO) δ 13.16 (d, J=20.9 Hz, 1H), 8.91 (s, 1H), 8.20 (d, J=7.2 Hz, 1H), 7.64 (t, J=8.3 Hz, 1H), 7.45 (t, J=7.8 Hz, 1H), 4.28 (m, 6H), 4.17 (m, 2H), 3.85-3.75 (m, 4H), 1.61 (s, 6H). LCMS: $R_T$=4.61 min, M+H$^+$=406

Example 151

4-(6,6-dimethyl-4-morpholino-8,9-dihydro-6H-[1,4]oxazino[3,4-e]purin-2-yl)benzonitrile 151

Following General Procedure A, 2-chloro-6,6-dimethyl-4-morpholino-8,9-dihydro-6H-[1,4]oxazino[3,4-e]purine (102 mg, 0.31 mmol), 4-(4,4,5,5-tetramethyl-1,3,2-dioxaborolan-2-yl)benzonitrile (0.31 mmole), and bis(di-tert-butyl(4-dimethylaminophenyl)phosphine)dichloropalladium (II) (11 mg, 16 umol) were reacted to give 151. 1H NMR (400 MHz, DMSO) δ 8.54 (d, J=8.5 Hz, 2H), 7.94 (d, J=8.4 Hz, 2H), 4.28 (m, 4H), 4.16 (m, 4H), 3.77 (m, 4H), 1.60 (s, 6H). LCMS: $R_T$=5.53 min, M+H$^+$=391

Example 152

5-(6,6-dimethyl-4-morpholino-8,9-dihydro-6H-[1,4]oxazino[3,4-e]purin-2-yl)nicotinamide 152

Following General Procedure A, 2-chloro-6,6-dimethyl-4-morpholino-8,9-dihydro-6H-[1,4]oxazino[3,4-e]purine (102 mg, 0.31 mmol), 5-(4,4,5,5-tetramethyl-1,3,2-dioxaborolan-2-yl)nicotinamide (0.31 mmole), and bis(di-tert-butyl(4-dimethylaminophenyl)phosphine)dichloropalladium (II) (11 mg, 16 umol) were reacted to give 152. 1H NMR (400 MHz, DMSO) δ 9.61 (dd, J=5.2, 2.0 Hz, 1H), 9.08 (t, J=2.7 Hz, 1H), 9.02 (t, J=2.1 Hz, 1H), 8.30 (s, 1H), 7.65 (s, 1H), 4.30 (s, 4H), 4.18 (dt, J=9.7, 4.5 Hz, 4H), 3.81-3.71 (m, 4H), 1.60 (s, 6H). LCMS: R$_T$=3.71 min, M+H$^+$=410

Example 153

5-(6,6-dimethyl-4-morpholino-8,9-dihydro-6H-[1,4] oxazino[3,4-e]purin-2-yl)-N-methylpicolinamide 153

Following General Procedure A, 2-chloro-6,6-dimethyl-4-morpholino-8,9-dihydro-6H-[1,4]oxazino[3,4-e]purine (102 mg, 0.31 mmol), N-methyl-5-(4,4,5,5-tetramethyl-1,3,2-dioxaborolan-2-yl)picolinamide (0.31 mmole), and bis(di-tert-butyl(4-dimethylaminophenyl)phosphine)dichloropalladium (II) (11 mg, 16 umol) were reacted to give 153. 1H NMR (400 MHz, DMSO) δ 9.51 (s, 1H), 8.81 (d, J=6.1 Hz, 1H), 8.79-8.72 (m, 1H), 8.13 (d, J=8.2 Hz, 1H), 4.28 (m, 4H), 4.17 (m, 4H), 3.78 (m, 4H), 2.86 (d, J=4.9 Hz, 3H), 1.60 (s, 6H). LCMS: R$_T$=4.64 min, M+H$^+$=424

Example 154

2-(4-(benzyloxy)phenyl)-6,6-dimethyl-4-morpholino-8,9-dihydro-6H-[1,4]oxazino[3,4-e]purine 154

Following General Procedure A, 2-chloro-6,6-dimethyl-4-morpholino-8,9-dihydro-6H-[1,4]oxazino[3,4-e]purine (102 mg, 0.31 mmol), 2-(4-(benzyloxy)phenyl)-4,4,5,5-tetramethyl-1,3,2-dioxaborolane (0.31 mmole), and bis(di-tert-butyl(4-dimethylaminophenyl)phosphine)dichloropalladium (II) (11 mg, 16 umol) were reacted to give 154. 1H NMR (400 MHz, DMSO) δ 8.31 (t, J=7.6 Hz, 2H), 7.48 (d, J=7.2 Hz, 2H), 7.41 (t, J=7.4 Hz, 2H), 7.34 (t, J=7.2 Hz, 1H), 7.10 (t, J=7.4 Hz, 2H), 5.17 (s, 2H), 4.25 (s, 4H), 4.14 (dd, J=6.7, 2.6 Hz, 4H), 3.81-3.71 (m, 4H), 1.58 (s, 6H). LCMS: R$_T$=6.21 min, M+H$^+$=472

Example 155

3-(6,6-dimethyl-4-morpholino-8,9-dihydro-6H-[1,4] oxazino[3,4-e]purin-2-yl)-N,N-dimethylaniline 155

Following General Procedure A, 2-chloro-6,6-dimethyl-4-morpholino-8,9-dihydro-6H-[1,4]oxazino[3,4-e]purine (102 mg, 0.31 mmol), N,N-dimethyl-3-(4,4,5,5-tetramethyl-1,3,2-dioxaborolan-2-yl)aniline (0.31 mmole), and bis(di-tert-butyl(4-dimethylaminophenyl)phosphine)dichloropalladium (II) (11 mg, 16 umol) were reacted to give 155. 1H NMR (400 MHz, DMSO) δ 7.80 (s, 1H), 7.71 (d, J=7.7 Hz, 1H), 7.26 (t, J=7.9 Hz, 1H), 6.82 (dd, J=8.2, 2.5 Hz, 1H), 4.25 (s, 4H), 4.23-4.06 (m, 4H), 3.84-3.69 (m, 4H), 2.96 (s, 6H), 1.59 (s, 6H). LCMS: R$_T$=3.88 min, M+H$^+$=409

Example 156

6,6-dimethyl-2-(4-(4-methylpiperazin-1-yl)phenyl)-4-morpholino-8,9-dihydro-6H-[1,4]oxazino[3,4-e] purine 156

Following General Procedure A, 2-chloro-6,6-dimethyl-4-morpholino-8,9-dihydro-6H-[1,4]oxazino[3,4-e]purine (102 mg, 0.31 mmol), 1-methyl-4-(4-(4,4,5,5-tetramethyl-1, 3,2-dioxaborolan-2-yl)phenyl)piperazine (0.31 mmole), and bis(di-tert-butyl(4-dimethylaminophenyl)phosphine)dichloropalladium (II) (11 mg, 16 umol) were reacted to give 156. 1H NMR (400 MHz, DMSO) δ 8.22 (d, J=8.9 Hz, 2H), 6.98 (d, J=8.9 Hz, 2H), 4.24 (s, 4H), 4.13 (d, J=3.2 Hz, 4H), 3.80-3.72 (m, 4H), 3.26-3.20 (m, 4H), 2.48-2.43 (m, 4H), 2.23 (s, 3H), 1.58 (s, 6H). LCMS: R$_T$=3.76 min, M+H$^+$=464

Example 157

6,6-dimethyl-4-morpholino-2-(4-(piperidin-1-yl) phenyl)-8,9-dihydro-6H-[1,4]oxazino[3,4-e]purine 157

Following General Procedure A, 2-chloro-6,6-dimethyl-4-morpholino-8,9-dihydro-6H-[1,4]oxazino[3,4-e]purine (102 mg, 0.31 mmol), 1-(4-(4,4,5,5-tetramethyl-1,3,2-dioxaborolan-2-yl)phenyl)piperidine (0.31 mmole), and bis(di-tert-butyl(4-dimethylaminophenyl)phosphine)dichloropalladium (II) (11 mg, 16 umol) were reacted to give 157. 1H NMR (400 MHz, DMSO) δ 8.21 (d, J=8.9 Hz, 2H), 6.96 (d, J=9.0 Hz, 2H), 4.23 (s, 4H), 4.13 (t, J=4.8 Hz, 4H), 3.81-3.69 (m, 4H), 3.27-3.21 (m, 4H), 1.61 (m, 6H), 1.58 (s, 6H). LCMS: R$_T$=4.13 min, M+H$^+$=449

Example 158

N-(5-(6,6-dimethyl-4-morpholino-8,9-dihydro-6H-[1,4]oxazino[3,4-e]purin-2-yl)romoace-2-yl)acetamide 158

Following General Procedure A, 2-chloro-6,6-dimethyl-4-morpholino-8,9-dihydro-6H-[1,4]oxazino[3,4-e]purine (102 mg, 0.31 mmol), N-(5-(4,4,5,5-tetramethyl-1,3,2-dioxaborolan-2-yl)romoace-2-yl)acetamide (0.31 mmole), and bis(di-tert-butyl(4-dimethylaminophenyl)phosphine)dichloropalladium (II) (11 mg, 16 umol) were reacted to give 158. 1H NMR (400 MHz, DMSO) δ 10.64 (s, 1H), 9.23 (d, J=2.2 Hz, 1H), 8.63 (dd, J=8.7, 2.3 Hz, 1H), 8.17 (d, J=8.8 Hz, 1H), 4.27 (s, 4H), 4.15 (dd, J=15.2, 5.1 Hz, 4H), 3.81-3.71 (m, 4H), 2.12 (s, 3H), 1.59 (s, 6H). LCMS: R$_T$=3.95 min, M+H$^+$=424

Example 159

5-(6,6-dimethyl-4-morpholino-8,9-dihydro-6H-[1,4] oxazino[3,4-e]purin-2-yl)picolinamide 159

Following General Procedure A, 2-chloro-6,6-dimethyl-4-morpholino-8,9-dihydro-6H-[1,4]oxazino[3,4-e]purine (102 mg, 0.31 mmol), 5-(4,4,5,5-tetramethyl-1,3,2-dioxaborolan-2-yl)picolinamide (0.31 mmole), and bis(di-tert-butyl(4-dimethylaminophenyl)phosphine)dichloropalladium (II) (11 mg, 16 umol) were reacted to give 159. 1H NMR (400 MHz, DMSO) δ 9.52 (d, J=1.8 Hz, 1H), 8.81 (dd, J=8.2, 2.1 Hz, 1H), 8.14 (d, J=8.2 Hz, 1H), 8.12 (s, 1H), 7.69 (s, 1H), 4.29 (s, 4H), 4.18 (m, 4H), 3.83-3.71 (m, 4H), 1.60 (s, 6H). LCMS: R$_T$=4.39 min, M+H$^+$=410

Example 160

6-(6,6-dimethyl-4-morpholino-8,9-dihydro-6H-[1,4] oxazino[3,4-e]purin-2-yl)romoace-3-ol 160

Following General Procedure A, 2-chloro-6,6-dimethyl-4-morpholino-8,9-dihydro-6H-[1,4]oxazino[3,4-e]purine (102 mg, 0.31 mmol), 6-(4,4,5,5-tetramethyl-1,3,2-dioxaborolan-2-yl)romoace-3-ol (0.31 mmole), and bis(di-tert-butyl(4-dimethylaminophenyl)phosphine)dichloropalladium (II) (11 mg, 16 umol) were reacted to give 160. 1H NMR (400 MHz, DMSO) δ 8.24 (m, 2H), 7.24 (dd, J=8.6, 2.9 Hz, 1H), 6.62 (s, 1H), 4.25 (s, 4H), 4.14 (d, J=2.5 Hz, 4H), 3.81-3.70 (m, 4H), 1.59 (s, 6H). LCMS: $R_T$=3.73 min, M+H$^+$=383

Example 161

(4-(6,6-dimethyl-4-morpholino-8,9-dihydro-6H-[1,4] oxazino[3,4-e]purin-2-yl)phenyl)(4-methylpiperazin-1-yl)methanone 161

Following General Procedure A, 2-chloro-6,6-dimethyl-4-morpholino-8,9-dihydro-6H-[1,4]oxazino[3,4-e]purine (102 mg, 0.31 mmol), (4-methylpiperazin-1-yl)(4-(4,4,5,5-tetramethyl-1,3,2-dioxaborolan-2-yl)phenyl)methanone (0.31 mmole), and bis(di-tert-butyl(4-dimethylaminophenyl)phosphine)dichloropalladium (II) (11 mg, 16 umol) were reacted to give 161. 1H NMR (400 MHz, DMSO) δ 8.43 (d, J=8.2 Hz, 2H), 7.47 (d, J=8.2 Hz, 2H), 4.28 (s, 4H), 4.21-4.08 (m, 4H), 3.82-3.71 (m, 4H), 3.62 (s, 4H), 2.33 (s, 4H), 2.20 (s, 3H), 1.60 (s, 6H). LCMS: $R_T$=3.64 min, M+H$^+$=492

Example 162

N-cyclopropyl-3-(6,6-dimethyl-4-morpholino-8,9-dihydro-6H-[1,4]oxazino[3,4-e]purin-2-yl)benzamide 162

Following General Procedure A, 2-chloro-6,6-dimethyl-4-morpholino-8,9-dihydro-6H-[1,4]oxazino[3,4-e]purine (102 mg, 0.31 mmol), N-cyclopropyl-3-(4,4,5,5-tetramethyl-1,3,2-dioxaborolan-2-yl)benzamide (0.31 mmole), and bis(di-tert-butyl(4-dimethylaminophenyl)phosphine)dichloropalladium (II) (11 mg, 16 umol) were reacted to give 162. 1H NMR (400 MHz, DMSO) δ 8.77 (s, 1H), 8.53 (d, J=4.0 Hz, 1H), 8.50 (d, J=7.8 Hz, 1H), 7.84 (d, J=7.7 Hz, 1H), 7.53 (t, J=7.7 Hz, 1H), 4.28 (s, 4H), 4.17 (dt, J=9.5, 4.4 Hz, 4H), 3.84-3.70 (m, 4H), 2.88 (tq, J=7.8, 4.0 Hz, 1H), 0.76-0.67 (m, 2H), 0.64-0.54 (m, 2H). LCMS: $R_T$=4.68 min, M+H$^+$=449

Example 163

5-(6,6-dimethyl-4-morpholino-8,9-dihydro-6H-[1,4] oxazino[3,4-e]purin-2-yl)-N,N-dimethylpyrazin-2-amine 163

Following General Procedure A, 2-chloro-6,6-dimethyl-4-morpholino-8,9-dihydro-6H-[1,4]oxazino[3,4-e]purine (102 mg, 0.31 mmol), N,N-dimethyl-5-(4,4,5,5-tetramethyl-1,3,2-dioxaborolan-2-yl)pyrazin-2-amine (0.31 mmole), and bis(di-tert-butyl(4-dimethylaminophenyl)phosphine)dichloropalladium (II) (11 mg, 16 umol) were reacted to give 163. 1H NMR (400 MHz, DMSO) δ 9.04 (s, 1H), 8.21 (s, 1H), 4.24 (s, 4H), 4.14 (t, J=5.3 Hz, 4H), 3.81-3.66 (m, 4H), 3.15 (s, 6H), 1.59 (s, 6H). LCMS: $R_T$=3.93 min, M+H$^+$=411

Example 167

2-(2-aminopyrimidin-5-yl)-7-methyl-4-morpholino-8,9-dihydropyrazino[2,1-e]purin-6(7H)-one 167

Step 1: 2-Chloro-6-morpholin-4-yl-9-(tetrahydro-pyran-2-yl)-9H-purine-8-carboxylic acid methylamide

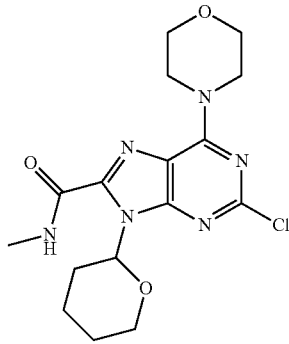

A solution of 2-chloro-6-morpholin-4-yl-9-(tetrahydro-pyran-2-yl)-9H-purine (0.50 g, 1.55 mmol) and N,N,N',N'-tetramethylethylenediamine (0.35 mL, 2.33 mmol) in dry THF (14 mL) was cooled to −78° C. Butyllithium (2.5M in hexanes, 1.22 mL, 3.05 mmol) was added dropwise and the dark yellow solution was stirred at −78° C. for 45 min. N-Succinimidyl N-methylcarbamate (0.4 g, 2.33 mmol) was added as a suspension in a small volume of THF and the mixture was allowed to warm to room temperature while stirring for 18 h. The reaction mixture was diluted with water, neutralized with 1M hydrochloric acid and extracted three times with ethyl acetate. The combined extracts were dried (Na$_2$SO$_4$), filtered and concentrated in vacuo. The resulting residue was subjected to flash chromatography (SiO$_2$, gradient 0-100% ethyl acetate in cyclohexane) to give 2-chloro-6-morpholin-4-yl-9-(tetrahydro-pyran-2-yl)-9H-purine-8-carboxylic acid methylamide (104 mg, 18%). LCMS $R_T$=3.26, [M+H]$^+$=381/383

Step 2: 2-Chloro-6-morpholin-4-yl-9H-purine-8-carboxylic acid methylamide

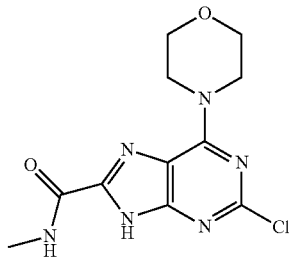

2-Chloro-6-morpholin-4-yl-9-(tetrahydro-pyran-2-yl)-9H-purine-8-carboxylic acid methylamide (104 mg, 0.27 mmol) was suspended in methanol (6 mL) and p-toluenesulfonic acid monohydrate (10 mg, 0.05 mmol) was added. The mixture was stirred at room temperature for 68 h, then diluted with water and neutralized with aqueous sodium bicarbonate. The solid precipitate was filtered off and dried at 50° C. under vacuum to give 2-chloro-6-morpholin-4-yl-9H-purine-8-carboxylic acid methylamide (56 mg, 70%). LCMS $R_T$=2.43, [M+H]$^+$=297/299

Step 3: 3-Chloro-7-methyl-1-morpholin-4-yl-6,7-dihydro-5H-2,4,4b,7,9-pentaaza-fluoren-8-one

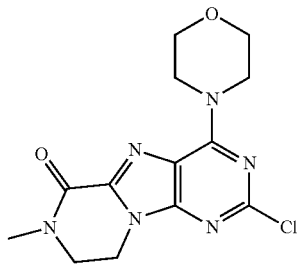

A mixture of 2-chloro-6-morpholin-4-yl-9H-purine-8-carboxylic acid methylamide (56 mg, 0.19 mmol) 1,2-dibromoethane (0.058 mL, 0.68 mmol) and cesium carbonate (0.25 g, 0.76 mmol) in DMF (2 mL) was heated at 100° C. for 2 h, then cooled, diluted with water and extracted five times with ethyl acetate. The combined extracts were dried (Na$_2$SO$_4$) and concentrated in vacuo. The resulting residue was triturated twice with diethyl ether and the solid was dried under vacuum to give 3-Chloro-7-methyl-1-morpholin-4-yl-6,7-dihydro-5H-2,4,4b,7,9-pentaaza-fluoren-8-one (47 mg, 77%). LCMS R$_T$=2.36, [M+H]$^-$323/325.

Step 4: A mixture of 3-chloro-7-methyl-1-morpholin-4-yl-6,7-dihydro-5H-2,4,4b,7,9-pentaaza-fluoren-8-one (47 mg, 0.15 mmol), 2-aminopyrimidine-5-boronic acid pinacol ester (39 mg, 0.18 mmol), and cesium carbonate (131 mg, 0.40 mmol) in 1,4-dioxane (1.5 mL) and water (1.5 mL) was purged with argon. Tetrakis(triphenylphosphine)palladium (0) (9 mg, 0.008 mmol) was added, the mixture was purged with argon again and then heated at 100° C. overnight. The mixture was cooled and diluted with water. The precipitate was filtered off, washed with water, and then triturated with ethanol. The solid was filtered off and dried (vacuum, 50° C.) to give 167 (15 mg, 26%). LCMS R$_T$=2.47, [M+H]$^-$382. $^1$H NMR (DMSO-d$_6$+d1-TFA, 400 MHz): δ 9.38 (2H, s), 4.79-4.06 (4H, v. broad), 4.44 (2H, t, J=6.0 Hz), 3.90 (2H, t, J=6.0 Hz), 3.80 (4H, t, J=4.7 Hz), 3.11 (3H, s).

Example 168

5-(8,8-Dimethyl-1-morpholin-4-yl-5,8-dihydro-6H-7-oxa-9-thia-2,4-diaza-fluoren-3-yl)-pyrimidin-2-ylamine 168

Step 1: 7-bromothieno[3,2-d]pyrimidine-2,4(1H,3H)-dione

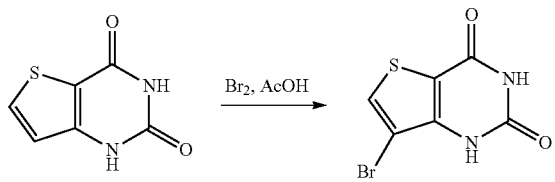

Thieno[3,2-d]pyrimidine-2,4(1H,3H)-dione (10.38 g, 61.72 mmol) was dissolved in acetic acid (230 mL) and Bromine (11.13 mL, 216 mmol) was added. The reaction was heated at 80° C. for 3.5 h. Complete reaction was confirmed by LCMS. The reaction mixture was poured onto ice water slowly and filtered off the precipitate which was dried overnight under vacuum to give 7-bromothieno[3,2-d]pyrimidine-2,4(1H,3H)-dione (9.1 g, 60% yield)

Step 2: 7-bromo-2,4-dichlorothieno[3,2-d]pyrimidine

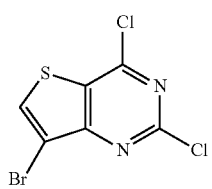

7-Bromothieno[3,2-d]pyrimidine-2,4(1H,3H)-dione (9.1 g, 37 mmol) was dissolved in POCl$_3$ (140 mL, 1500 mmol) and heated at 110° C. with a vigreux condensation column attached for 20 hrs. Complete reaction confirmed by LCMS. Poured onto ice water slowly and filtered off the precipitate. The product was purified by silica gel chromatography (0 to 100% ethyl acetate/heptanes) on the CombiFlash® (Teledyne Isco Co.) Rf system and concentrated in vacuo to give 7-bromo-2,4-dichlorothieno[3,2-d]pyrimidine (8.4 g, 80% yield)

Step 3: 4-(7-bromo-2-chlorothieno[3,2-d]pyrimidin-4-yl)morpholine

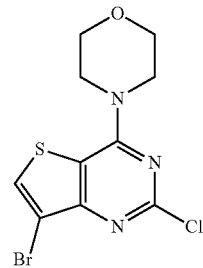

7-Bromo-2,4-dichlorothieno[3,2-d]pyrimidine (2.9 g, 10.0 mmol) was dissolved in methanol (100 mL, 2000 mmol) and added morpholine (2 mL, 22 mmol) and let the reaction mixture stir for 1.5 h. Complete reaction confirmed by LCMS. Concentrated in vacuo and diluted with water. Extracted with DCM and concentrated in vacuo again. The product was purified by silica gel chromatography (0 to 100% ethyl acetate/heptanes) on the CombiFlash® Rf system and concentrated in vacuo to give 4-(7-bromo-2-chlorothieno[3,2-d]pyrimidin-4-yl)morpholine (1.2 g, 35% yield). $^1$H NMR (400 MHz, CDCl$_3$) δ 7.78 (s, 1H), 4.01 (m, 4H), 3.85 (m, 4H)

Step 4: 4-(2-chloro-7-vinylthieno[3,2-d]pyrimidin-4-yl)morpholine

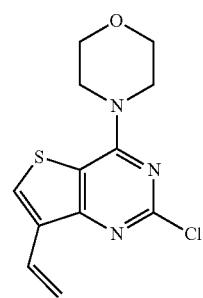

4-(7-bromo-2-chlorothieno[3,2-d]pyrimidin-4-yl)morpholine (3.55 g, 10.6 mmol), (2-Ethenyl)tri-n-butyltin (3.41 mL, 11.7 mmol), Pd(PPh$_3$)$_4$ (613 mg, 0.53 mmol), and 1,4-Dioxane (30 mL, 400 mmol) were combined in a sealed tube and heated at 100° C. 19.5 h. Complete reaction was confirmed by LCMS. Concentrated in vacuo and purified by silica gel chromatography (0 to 50% ethyl acetate/heptanes) on the CombiFlash® Rf system and concentrated in vacuo to give 4-(2-chloro-7-vinylthieno[3,2-d]pyrimidin-4-yl)morpholine (1.18 g, 39.5% yield)

Step 5: 2-(2-chloro-4-morpholinothieno[3,2-d]pyrimidin-7-yl)ethanol

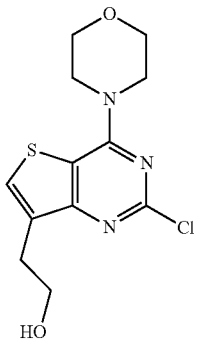

4-(2-chloro-7-vinylthieno[3,2-d]pyrimidin-4-yl)morpholine (170 mg, 0.6 mmol) was dissolved in tetrahydrofuran (10 mL, 100 mmol) and cooled to 0° C. under an atmosphere of nitrogen. 0.5 M 9-BBN in hexanes (3.4 mL, 2 mmol) was added and the reaction was allowed to warm up to room temperature and stir overnight. LCMS indicated mostly starting material so the reaction was cooled to 0° C. again and added 0.5 M 9-BBN in hexanes (8.0 mL, 4 mmol) and allowed to warm up to room temperature and stir overnight again. Added 20 M hydrogen peroxide (1.4 mL, 20 mmol) followed by 5 M sodium hydroxide in water (2.4 mL, 10 mmol). The reaction was diluted with water and extracted with ethyl acetate, dried over magnesium sulfate and concentrated in vacuo and was purified by silica gel chromatography (0 to 50% ethyl acetate/heptanes) on the CombiFlash® Rf system and concentrated in vacuo to give 2-(2-chloro-4-morpholinothieno[3,2-d]pyrimidin-7-yl)ethanol (110 mg, 61% yield)

Step 6: 2-(2-chloro-7-(2-hydroxyethyl)-4-morpholinothieno[3,2-d]pyrimidin-6-yl)propan-2-ol

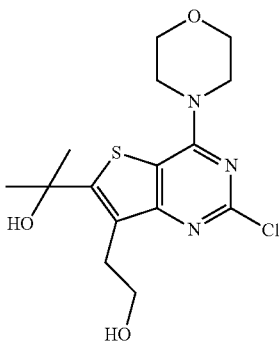

2-(2-chloro-4-morpholinothieno[3,2-d]pyrimidin-7-yl)ethanol (70 mg, 0.2 mmol) was dissolved in tetrahydrofuran (5 mL, 60 mmol) and cooled to −40° C. under an atmosphere of nitrogen. Added 2.5 M n-BuLi in hexanes (370 mL, 0.93 mmol) and allowed to stir for 1 h. Added acetone (86 uL, 1.2 mmol) and again stirred at −40° C. for 5 h. Reaction never went to completion and was quenched with saturated ammonium chloride and extracted with ethyl acetate, dried over magnesium sulfate and concentrated in vacuo to give an unpurified mixture of starting material and 2-(2-chloro-7-(2-hydroxyethyl)-4-morpholinothieno[3,2-d]pyrimidin-6-yl)propan-2-ol (30 mg)

Step 7: 3-Chloro-8,8-dimethyl-1-morpholin-4-yl-5,8-dihydro-6H-7-oxa-9-thia-2,4-diaza-fluorene

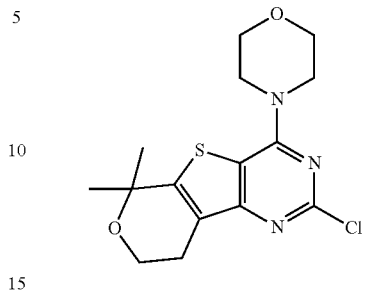

Impure 2-(2-chloro-7-(2-hydroxyethyl)-4-morpholinothieno[3,2-d]pyrimidin-6-yl)propan-2-ol (30 mg) was dissolved in toluene (5 mL, 50 mmol). Trifluoroacetic acid (0.5 mL, 6 mmol) was added and the reaction mixture was heated at 120° C. for two h. Complete reaction was confirmed by LCMS. Diluted with water and extracted with ethyl acetate, dried over magnesium sulfate, concentrated in vacuo and was purified by silica gel chromatography (0 to 100% ethyl acetate/heptanes) on the CombiFlash® Rf system using an amine column and concentrated in vacuo to give 3-Chloro-8,8-dimethyl-1-morpholin-4-yl-5,8-dihydro-6H-7-oxa-9-thia-2,4-diaza-fluorene (10 mg, 10% yield)

Step 8: 3-Chloro-8,8-dimethyl-1-morpholin-4-yl-5,8-dihydro-6H-7-oxa-9-thia-2,4-diaza-fluorene (10 mg, 0.03 mmol) was dissolved in acetonitrile (2 mL, 40 mmol) and added 1 M sodium carbonate in water (2 mL, 2 mmol), 5-(4,4,5,5-tetramethyl-1,3-dioxolan-2-yl)pyrimidin-2-amine (9.0 mg, 0.041 mmol), and Bis(di-tert-butyl(4-dimethylaminophenyl)phosphine)dichloropalladium(II) (1.1 mg, 0.001 6 mmol). The reaction was placed on the Biotage microwave at 120° C. for 15 minutes. The aqueous layer was pipetted off and the organic layer was concentrated in vacuo and was purified by silica gel chromatography (0 to 100% ethyl acetate/heptanes) on the CombiFlash® Rf system using a basic alumina column and concentrated in vacuo to give (85% pure) 168 (2.7 mg, 20% yield). M+1: 399.3. $^1$H NMR (400 MHz, CDCl$_3$) δ 9.30 (s, 2H), 5.34 (brs, 2H), 4.08 (t, 2H), 4.01 (m, 4H), 3.87 (m, 4H), 2.95 (t, 2H), 1.62 (s, 6H)

Example 169

2-(1H-indazol-4-yl)-4-morpholino-6-(trifluoromethyl)-8,9-dihydro-6H-[1,4]oxazino[3,4-e]purine 169

Step 1: 4-morpholino-2-(1-(tetrahydro-2H-pyran-2-yl)-1H-indazol-4-yl)-6-(trifluoromethyl)-8,9-dihydro-6H-[1,4]oxazino[3,4-e]purine

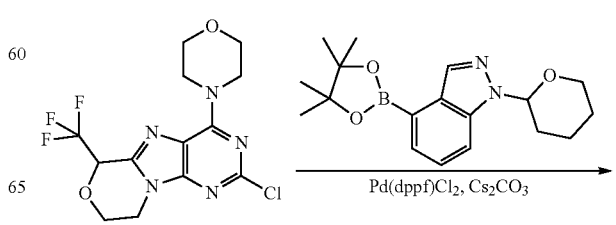

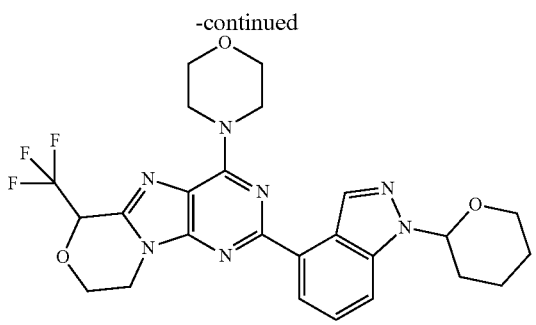

2-Chloro-4-morpholino-6-(trifluoromethyl)-8,9-dihydro-6H-[1,4]oxazino[3,4-e]purine, from Examples 139 and 140 (90 mg, 0.0002 mol) and 1-(tetrahydro-2H-pyran-2-yl)-4-(4,4,5,5-tetramethyl-1,3,2-dioxaborolan-2-yl)-1H-indazole (160 mg, 0.0005 mol) were reacted with Pd(dppf)Cl$_2$ ([1,1'-bis(diphenylphosphino)ferrocene]dichloropalladium(II), complex with dichloromethane) and cesium carbonate under microwave Suzuki palladium conditions to give 4-morpholino-2-(1-(tetrahydro-2H-pyran-2-yl)-1H-indazol-4-yl)-6-(trifluoromethyl)-8,9-dihydro-6H-[1,4]oxazino[3,4-e]purine (90 mg, 90% yield). LC/MS (ESI+): m/z 530 (M+H)

Step 2: 4-Morpholino-2-(1-(tetrahydro-2H-pyran-2-yl)-1H-indazol-4-yl)-6-(trifluoromethyl)-8,9-dihydro-6H-[1,4]oxazino[3,4-e]purine (100 mg, 0.0002 mol) in MeOH (1 mL) was treated with a catalytic amount of p-toluenesulfonic acid (3 mg, 0.02 mmol). The reaction mixture was heated to 50° C. overnight and was then concentrated under reduce pressure. The residue was partitioned between water and EtOAc. The organic extracts were washed with water, brine, dried over MgSO$_4$ and concentrated to dryness to give 169 (13 g, 16% yield). LC/MS (ESI+): m/z 446 (M+H). $^1$H NMR (400 MHz, DMSO) δ 13.16 (s, 1H), 8.92 (s, 1H), 8.22 (d, J=7.2 Hz, 1H), 7.66 (d, J=8.2 Hz, 1H), 7.47 (t, J=7.8 Hz, 1H), 5.93 (q, J=6.8 Hz, 1H), 4.55-4.17 (m, 8H), 3.80 (t, J=4.6 Hz, 4H)

Example 170
3-(4-morpholino-6-(trifluoromethyl)-8,9-dihydro-6H-[1,4]oxazino[3,4-e]purin-2-yl)phenol 170

2-Chloro-4-morpholino-6-(trifluoromethyl)-8,9-dihydro-6H-[1,4]oxazino[3,4-e]purine, from Examples 139 and 140 (50 mg, 0.00015 mol) and 3-(4,4,5,5-tetramethyl-1,3,2-dioxaborolan-2-yl)phenol (76 mg, 0.00034 mol) were reacted with Pd(dppf)Cl$_2$ and cesium carbonate under microwave Suzuki palladium conditions to give 170 (10 mg, 15% yield). LC/MS (ESI+): m/z 422 (M+H). $^1$H NMR (400 MHz, DMSO) δ 7.96-7.74 (m, 2H), 7.26 (t, J=8.1 Hz, 1H), 6.83 (dt, J=23.4, 11.6 Hz, 1H), 5.89 (q, J=6.9 Hz, 1H), 4.51-4.08 (m, 8H), 3.77 (t, J=4.6 Hz, 4H), 1.23-0.98 (m, 1H)

Example 171
5-(4-((2S,6R)-2,6-dimethylmorpholino)-6,6-dimethyl-8,9-dihydro-6H-[1,4]oxazino[3,4-e]purin-2-yl)pyrimidin-2-amine 171

Step 1: 2,6-Dichloro-9-(tetrahydro-pyran-2-yl)-9H-purine

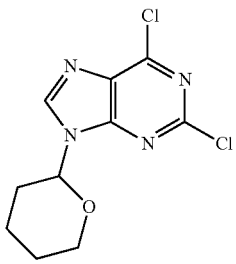

A mixture of 2,6-dichloro-9H-purine (10.0 g, 53 mmol), 3,4-dihydro-2H-pyran (9.5 mL, 93 mmol) and p-toluenesulfonic acid monohydrate (1.0 g, 5.0 mmol) in THF (100 mL) was heated at 100° C. for 18 h, then cooled to RT and concentrated in vacuo. The resulting residue was purified by column chromatography (SiO$_2$, 0 to 10% ethyl acetate in cyclohexane) affording 2,6-Dichloro-9-(tetrahydro-pyran-2-yl)-9H-purine as a cream solid (10.9 g, 75%). $^1$H NMR (400 MHz, CDCl$_3$): δ 8.33 (1H, s), 5.77 (1H, dd, J=10.4, 2.4 Hz), 4.19 (1H, m), 3.78 (1H, dt, J=11.6, 2.9 Hz), 2.17 (1H, m), 2.09 (1H, m), 1.98 (1H, m), 1.87-1.69 (3H, m).

Step 2: 2-[2,6-Dichloro-9-(tetrahydro-pyran-2-yl)-9H-purin-8-yl]-propan-2-ol

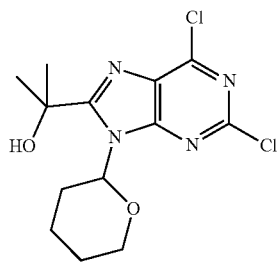

BuLi (20 mL, 40.0 mmol, 2 M in pentane) was added dropwise to a solution of 2,6-dichloro-9-(tetrahydro-pyran-2-yl)-9H-purine (8.0 g, 29.3 mmol) and TMEDA (6.4 mL, 42.4 mmol) in anhydrous THF (100 mL) at −78° C. The resulting dark solution was stirred at −78° C. for 45 min, then acetone (4 mL, 54.5 mmol) was added and the reaction mixture was stirred at −78° C. for 30 min, then at RT for 30 min. The reaction mixture was quenched with water and extracted with ethyl acetate. The combined organic extracts were dried (MgSO$_4$) and concentrated in vacuo. The resulting residue was purified by column chromatography (SiO$_2$, 0 to 20% ethyl acetate in cyclohexane) affording 2-[2,6-Dichloro-9-(tetrahydro-pyran-2-yl)-9H-purin-8-yl]-propan-2-ol as a dark solid (6.0 g, 62%). $^1$H NMR (400 MHz, CDCl$_3$): δ 6.19 (1H, dd, J=11.2, 2.8 Hz), 4.26 (1H, m), 3.77 (1H, m), 2.87 (1H, m), 2.09 (1H, m), 1.90-1.71 (11H, m).

Step 3: 2-(2,6-Dichloro-9H-purin-8-yl)-propan-2-ol

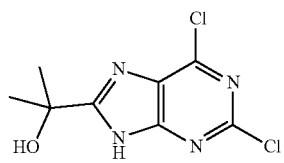

HCl (5 mL, 5 mmol, 1 M aqueous solution) was added to a solution of 2-[2,6-dichloro-9-(tetrahydro-pyran-2-yl)-9H-purin-8-yl]-propan-2-ol (6.0 g, 20.66 mmol) in a mixture of DCM (15 mL) and methanol (15 mL) and the resulting solution stirred at RT for 1 h, then concentrated in vacuo. The resulting residue was purified by column chromatography (SiO$_2$, gradient 0 to 50% methanol in DCM) affording 2-(2,6-Dichloro-9H-purin-8-yl)-propan-2-ol as a dark solid (3.38 g, 66%). LCMS (method A): R$_T$=2.12 min, [M−H]=245/247. $^1$H NMR (400 MHz, CDCl$_3$): δ 1.50 (6H, s)

Step 4: 1,3-Dichloro-8,8-dimethyl-5,6-dihydro-8H-7-oxa-2,4,4b,9-tetraaza-fluorene

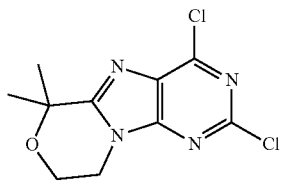

Cesium carbonate (9.3 g, 28.5 mmol) and 1,2-dibromoethane (4.1 mL, 47.6 mmol) were added to a solution of 2-(2,6-dichloro-9H-purin-8-yl)-propan-2-ol (3.3 g, 13.36 mmol) in DMF (100 mL) and the reaction mixture was heated at 100° C. for 2 h, then partitioned between water and ethyl acetate. The organic extract was separated and washed with brine, then dried (MgSO$_4$) and concentrated in vacuo. The resulting residue was purified by column chromatography (SiO$_2$, 0 to 10 to 20% ethyl acetate in cyclohexane) affording 1,3-Dichloro-8,8-dimethyl-5,6-dihydro-8H-7-oxa-2,4,4b,9-tetraaza-fluorene as a yellow solid (1.0 g, 27%). $^1$H NMR (400 MHz, CDCl$_3$): δ 4.26 (2H, dd, J=6, 4 Hz), 4.19 (2H, dd, J=6, 4 Hz).

Step 5: 3-Chloro-1-((2R,6S)-2,6-dimethyl-morpholin-4-yl)-8,8-dimethyl-5,6-dihydro-8H-7-oxa-2,4,4b,9-tetraaza-fluorene

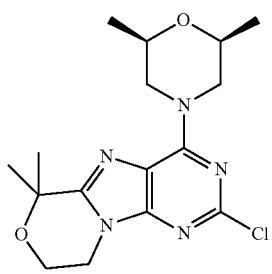

A mixture of 1,3-dichloro-8,8-dimethyl-5,6-dihydro-8H-7-oxa-2,4,4b,9-tetraaza-fluorene (100 mg, 0.366 mmol), (2R,6S)-2,6-dimethyl-morpholine (84 mg, 0.732 mmol) and triethylamine (77 μL, 0.55 mmol) in IMS (2 mL) was heated at 140° C. for 20 mins in a microwave reactor, then concentrated in vacuo. The resulting residue was purified by column chromatography (SiO$_2$, 10% ethyl acetate in cyclohexane) affording 3-Chloro-1-((2R,6S)-2,6-dimethyl-morpholin-4-yl)-8,8-dimethyl-5,6-dihydro-8H-7-oxa-2,4,4b,9-tetraaza-fluorene as a white solid (128 mg, 99%). LCMS (method A): R$_T$=3.62 min, [M+H]$^+$=352.

Step 6: A mixture of 3-chloro-1-((2R,6S)-2,6-dimethyl-morpholin-4-yl)-8,8-dimethyl-5,6-dihydro-8H-7-oxa-2,4,4b,9-tetraaza-fluorene (128 mg, 0.36 mmol), 5-(4,4,5,5-tetramethyl-[1,3,2]dioxaborolan-2-yl)-pyrimidin-2-ylamine (121 mg, 0.55 mmol), PdCl$_2$(PPh$_3$)$_2$ (26 mg, 0.036 mmol) and sodium carbonate (1 mL, 1.0 mmol, 1M aqueous solution) in acetonitrile (4 mL) was degassed and heated at 120° C. for 30 mins in a microwave reactor, then heated thermally at 100° C. for 18 hours. The reaction mixture was loaded onto an Isolute® SCX-2 cartridge which was washed with methanol and the product eluted with 2M ammonia in methanol. The basic fractions were combined and concentrated in vacuo. The resulting residue was purified by reverse phase HPLC (Phenomenex Gemini 5 μm C18, 0.1% HCO$_2$H in water gradient 5-98% acetonitrile) affording 171 as a white solid (10 mg, 7%). LCMS (method B): R$_T$=4.14 min, [M+H]$^+$=411. $^1$H NMR (400 MHz, CDCl$_3$): δ 9.26 (2H, s), 5.49-5.30 (2H, v. broad s), 5.20 (2H, broad s), 4.21 (2H, m), 4.15 (2H, m), 3.75 (2H, m), 2.80 (2H, m), 1.67 (6H, s), 1.30 (6H, d, J=6.8 Hz)

Example 172

5-(4-(2,2-dimethylmorpholino)-6,6-dimethyl-8,9-dihydro-6H-[1,4]oxazino[3,4-e]purin-2-yl)pyrimidin-2-amine 172

Step 1: 3-Chloro-1-(2,2-dimethyl-morpholin-4-yl)-8,8-dimethyl-5,6-dihydro-8H-7-oxa-2,4,4b,9-tetraaza-fluorene

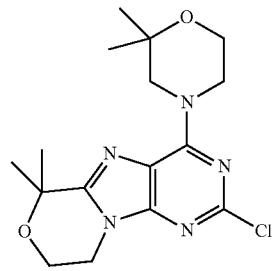

A mixture of 1,3-dichloro-8,8-dimethyl-5,6-dihydro-8H-7-oxa-2,4,4b,9-tetraaza-fluorene (100 mg, 0.366 mmol), 2,2-dimethyl-morpholine (84 mg, 0.732 mmol) and triethylamine (77 μL, 0.55 mmol) in IMS (2 mL) was heated at 140° C. for 20 mins in a microwave reactor, then concentrated in vacuo. The resulting residue was purified by column chromatography (SiO$_2$, 10% ethyl acetate in cyclohexane) affording 3-Chloro-1-(2,2-dimethyl-morpholin-4-yl)-8,8-dimethyl-5,6-dihydro-8H-7-oxa-2,4,4b,9-tetraaza-fluorene as a white solid (110 mg, 85%). LCMS (method A): R$_T$=3.51 min, [M+H]$^+$=352.

Step 2: A mixture of 3-chloro-1-(2,2-dimethyl-morpholin-4-yl)-8,8-dimethyl-5,6-dihydro-8H-7-oxa-2,4,4b,9-tetraaza-fluorene (110 mg, 0.31 mmol), 5-(4,4,5,5-tetramethyl-[1,3,2]dioxaborolan-2-yl)-pyrimidin-2-ylamine (104 mg, 0.47 mmol), PdCl$_2$(PPh$_3$)$_2$ (22 mg, 0.031 mmol) and sodium carbonate (1 mL, 1.0 mmol, 1M aqueous solution) in acetonitrile (4 mL) was degassed and heated at 120° C. for 30 mins in a microwave reactor, then heated at 100° C. for 18 hours. The reaction mixture was loaded onto an Isolute® SCX-2 cartridge which was washed with methanol and the product eluted with 2M ammonia in methanol. The basic fractions were combined and concentrated in vacuo. The resulting residue was purified by reverse phase HPLC (Phenomenex Gemini 5 μm C18, 0.1% HCO$_2$H in water gradient 5-98% acetonitrile) affording 172 as a white solid (11 mg, 9%). LCMS (method B): R$_T$=4.00 min, [M+H]$^+$=411. $^1$H NMR (400 MHz, CDCl$_3$): δ 9.25 (2H, s), 5.20 (2H, broad s), 4.46-4.13 (8H, m), 3.88 (2H, m), 1.66 (6H, s), 1.28 (6H, s).

Example 174

5-(4-((1S,4S)-2-oxa-5-azabicyclo[2.2.1]heptan-5-yl)-6,6-dimethyl-8,9-dihydro-6H-[1,4]oxazino[3,4-e]purin-2-yl)pyrimidin-2-amine 174

Step 1: 3-Chloro-8,8-dimethyl-1-(1S,4S)-2-oxa-5-aza-bicyclo[2.2.1]hept-5-yl-5,6-dihydro-8H-7-oxa-2,4,4b,9-tetraaza-fluorene

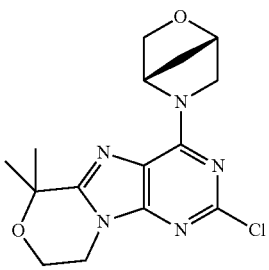

A mixture of 1,3-dichloro-8,8-dimethyl-5,6-dihydro-8H-7-oxa-2,4,4b,9-tetraaza-fluorene (100 mg, 0.366 mmol), (1S,4S)-2-oxa-5-aza-bicyclo[2.2.1]heptane (73 mg, 0.732 mmol) and triethylamine (77 μL, 0.55 mmol) in IMS (2 mL) was heated at 140° C. for 20 mins in a microwave reactor, then concentrated in vacuo. The resulting residue was purified by column chromatography (SiO$_2$, 10% ethyl acetate in pentane) affording 3-chloro-8,8-dimethyl-1-(1S,4S)-2-oxa-5-aza-bicyclo[2.2.1]hept-5-yl-5,6-dihydro-8H-7-oxa-2,4,4b,9-tetraaza-fluorene as a yellow solid (120 mg, 98%). LCMS (method A): R$_T$=2.81 min, [M+H]$^+$=336.

Step 2: A mixture of 3-chloro-8,8-dimethyl-1-(1S,4S)-2-oxa-5-aza-bicyclo[2.2.1]hept-5-yl-5,6-dihydro-8H-7-oxa-2,4,4b,9-tetraaza-fluorene (120 mg, 0.36 mmol), 5-(4,4,5,5-tetramethyl-[1,3,2]dioxaborolan-2-yl)-pyrimidin-2-ylamine (87 mg, 0.39 mmol), Pd(PPh$_3$)$_4$ (21 mg, 0.018 mmol) and cesium carbonate (163 mg, 0.5 mmol) in a mixture of 1,4-dioxane (1.5 mL) and water (0.5 mL) was degassed and heated at 130° C. for 20 mins in a microwave reactor. The reaction mixture was loaded onto an Isolute® SCX-2 cartridge which was washed with methanol and the product eluted with 2M ammonia in methanol. The basic fractions were combined and concentrated in vacuo. The resulting residue was purified by reverse phase HPLC (Phenomenex Gemini 5 μm C18, 0.1% HCO$_2$H in water gradient 5-98% acetonitrile) affording 174 as a white solid (45 mg, 32%). LCMS (method B): R$_T$=3.31 min, [M+H]$^+$=395. $^1$H NMR (400 MHz, DMSO-d$_6$, 80° C.): δ 9.08 (2H, s), 6.54 (2H, broad s), 5.75 (1H, broad s), 4.71 (1H, s), 4.12 (4H, m), 3.87 (1H, dd, J=7.4, 1.4 Hz), 3.79 (2H, s), 3.75 (1H, d, J=7.4 Hz), 1.95 (2H, s), 1.59 (6H, d, J=6.7 Hz)

Example 175

2-(2-aminopyrimidin-5-yl)-6-methyl-4-morpholino-6,7-dihydropyrazino[2,1-e]purin-8(9H)-one 175

Step 1: 1-[2-Chloro-6-morpholin-4-yl-9-(tetrahydro-pyran-2-yl)-9H-purin-8-yl]-ethanone

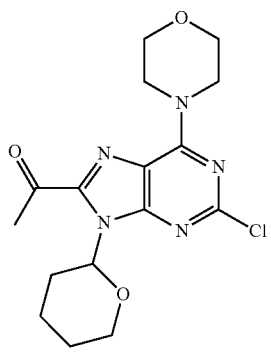

A solution of 2-Chloro-6-morpholin-4-yl-9-(tetrahydro-pyran-2-yl)-9H-purine (0.50 g, 1.55 mmol) and N,N,N',N'-tetramethylethylenediamine (0.35 mL, 2.33 mmol) in dry THF (14 mL) was cooled to −78° C. n-BuLi (2.5M in hexanes, 1.22 mL, 3.05 mmol) was added dropwise and the mixture was stirred at −78° C. for 40 min. N-methyl-N-methoxyacetamide (0.25 mL, 2.33 mmol) was added dropwise and the mixture was stirred at −78° C. for 1.5 h, then allowed to warm to −30° C. Water was added followed by 1M aqueous HCl and the mixture was extracted seven times with ethyl acetate. The combined organic extracts were dried (Na$_2$SO$_4$), filtered and concentrated in vacuo. The resulting residue was subjected to flash chromatography (SiO2), gradient 0-50% ethyl acetate in cyclohexane to give 1-[2-Chloro-6-morpholin-4-yl-9-(tetrahydro-pyran-2-yl)-9H-purin-8-yl]-ethanone (0.47 g, 83%). LCMS R$_T$=3.57 min, [M+H]$^+$=366/368

Step 2: 1-[2-Chloro-6-morpholin-4-yl-9-(tetrahydro-pyran-2-yl)-9H-purin-8-yl]-ethanol

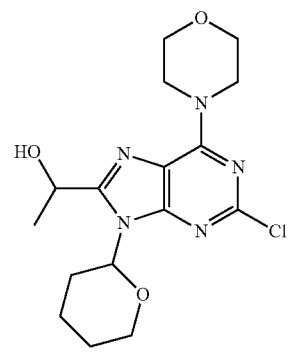

To a stirred suspension of 1-[2-chloro-6-morpholin-4-yl-9-(tetrahydro-pyran-2-yl)-9H-purin-8-yl]-ethanone (0.47 g, 1.29 mmol) in ethanol (8 mL) and THF (8 mL) was added sodium borohydride (49 mg, 1.30 mmol). The reaction mixture was stirred at room temperature for 1.5 h, then concentrated in vacuo. The resulting residue was dissolved in ethyl acetate and aqueous sodium bicarbonate and the phases were separated. The aqueous phase was extracted twice with ethyl acetate. The combined organic fractions were dried (Na$_2$SO$_4$), filtered and concentrated in vacuo to give 1-[2-Chloro-6-morpholin-4-yl-9-(tetrahydro-pyran-2-yl)-9H-purin-8-yl]-ethanol (0.50 g, quantitative). LCMS R$_T$=3.20 min, [M+H]$^+$=368/370

Step 3: 8-(1-Azido-ethyl)-2-chloro-6-morpholin-4-yl-9-(tetrahydro-pyran-2-yl)-9H-purine

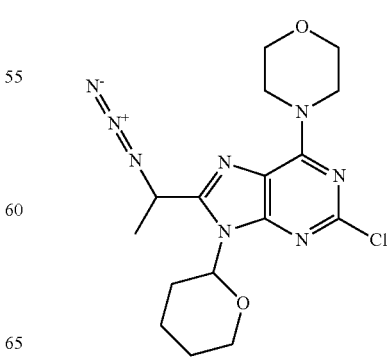

1-[2-Chloro-6-morpholin-4-yl-9-(tetrahydro-pyran-2-yl)-9H-purin-8-yl]-ethanol (0.37 g, 1.01 mmol) was dissolved in anhydrous toluene (5.6 mL) and DMF (0.9 mL) and the solution was cooled in ice. Diphenylphosphoryl azide (0.56 mL, 2.54 mmol) was added, followed by dropwise addition of 1,8-diazabicyclo[5.4.0]undec-7-ene (0.37 mL, 2.54 mmol).

The reaction mixture was stirred at room temperature for 16 h, then diluted with ethyl acetate followed by water and the phases were separated. The aqueous phase was extracted twice with ethyl acetate and the combined organic fractions were dried ($Na_2SO_4$), filtered and concentrated in vacuo. The resulting residue, together with crude product from a reaction performed similarly on a smaller scale (0.10 g, 0.27 mmol of 1-[2-chloro-6-morpholin-4-yl-9-(tetrahydro-pyran-2-yl)-9H-purin-8-yl]-ethanol), was subjected to flash chromatography (SiO2) gradient 0-50% ethyl acetate in cyclohexane to give 8-(1-Azido-ethyl)-2-chloro-6-morpholin-4-yl-9-(tetrahydro-pyran-2-yl)-9H-purine as two separated pairs of diastereomers (0.25 g and 0.27 g, total 0.52 g, 100%). LCMS $R_T$=4.05 min, $[M+H]^+$=393/395. LCMS $R_T$=4.16 min, $[M+H]^+$=393/395

Step 4: 1-[2-Chloro-6-morpholin-4-yl-9-(tetrahydro-pyran-2-yl)-9H-purin-8-yl]-ethylamine

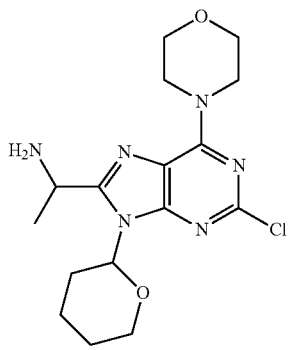

To a solution of 8-(1-azido-ethyl)-2-chloro-6-morpholin-4-yl-9-(tetrahydro-pyran-2-yl)-9H-purine (0.47 g, 1.20 mmol) in THF (13 mL) and water (4 mL) was added triphenylphosphine (0.33 g, 1.28 mmol). The reaction mixture was heated at 70° C. for 2 h, then cooled to RT. Ethyl acetate was added and the phases were separated. The aqueous phase was extracted three times with ethyl acetate. The combined organic fractions were dried ($Na_2SO_4$), filtered and concentrated in vacuo. The resulting residue, together with crude product from a reaction performed similarly on a smaller scale (0.05 g, 0.14 mmol of 8-(1-azido-ethyl)-2-chloro-6-morpholin-4-yl-9-(tetrahydro-pyran-2-yl)-9H-purine), was subjected to flash chromatography (SiO2) gradient 0-10% methanol in DCM). Eluted material containing title compound and triphenylphosphine oxide was subjected to flash chromatography (SiO2) gradient 0-20% methanol in TBME), and clean material from the two columns was combined to give 1-[2-Chloro-6-morpholin-4-yl-9-(tetrahydro-pyran-2-yl)-9H-purin-8-yl]-ethylamine (0.41 g, 84%, mixture of two pairs of diastereomers). LCMS $R_T$=2.15 min and 2.19 min, $[M+H]^+$=367/369

Step 5: 2-Bromo-N-{1-[2-chloro-6-morpholin-4-yl-9-(tetrahydro-pyran-2-yl)-9H-purin-8-yl]-ethyl}-acetamide

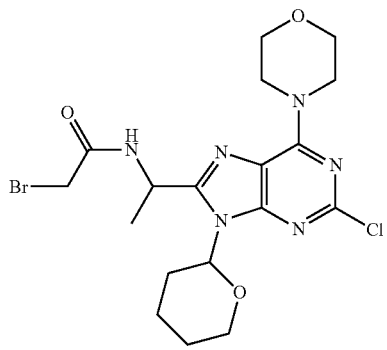

To a solution of 1-[2-chloro-6-morpholin-4-yl-9-(tetrahydro-pyran-2-yl)-9H-purin-8-yl]-ethylamine (0.25 g, 0.68 mmol) in anhydrous DCM were added romoacetyl bromide (62 µL, 0.74 mmol) and triethylamine (0.13 mL, 0.93 mmol). The mixture was stirred at RT. After 2 h, another portion of romoacetyl bromide (12 µL) was added and stirring continued for 1.5 h. Water was added, the phases were separated and the aqueous phase was extracted twice with DCM. The combined organic fractions were dried ($Na_2SO_4$), filtered and concentrated in vacuo to give 2-Bromo-N-{1-[2-chloro-6-morpholin-4-yl-9-(tetrahydro-pyran-2-yl)-9H-purin-8-yl]-ethyl}-acetamide (385 mg, mixture of two pairs of diastereomers), which was used in the next step without purification. LCMS $R_T$=3.45 min and 3.52 min, $[M+H]^+$=487/489/491

Step 6: 2-Bromo-N-[1-(2-chloro-6-morpholin-4-yl-9H-purin-8-yl)-ethyl]-acetamide

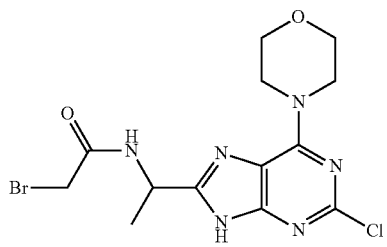

2-Bromo-N-{1-[2-chloro-6-morpholin-4-yl-9-(tetrahydro-pyran-2-yl)-9H-purin-8-yl]-ethyl}-acetamide (crude from step 5, 385 mg) was dissolved in methanol (15 mL) and p-toluenesulfonic acid monohydrate (35 mg) was added. The mixture was stirred at RT for 16 h. Water was added, aqueous sodium bicarbonate was added to give pH 7 and the precipitate was filtered off, washed with water and dried (in vacuo, 50° C.) to give 2-Bromo-N-[1-(2-chloro-6-morpholin-4-yl-9H-purin-8-yl)-ethyl]-acetamide (207 mg, 76%). The aqueous filtrate was extracted three times with ethyl acetate. The organic layer was separated and dried ($Na_2SO_4$), then concentrated in vacuo to afford a further crop of less pure 2-Bromo-N-[1-(2-chloro-6-morpholin-4-yl-9H-purin-8-yl)-ethyl]-acetamide (39 mg). LCMS $R_T$=2.57 min, $[M+H]^+$=403/405/407

Step 7: 3-Chloro-8-methyl-1-morpholin-4-yl-7,8-dihydro-2,4,4b,7,9-pentaaza-fluoren-6-one

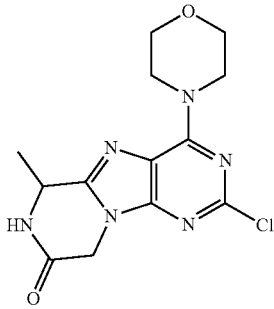

A mixture of 2-bromo-N-[1-(2-chloro-6-morpholin-4-yl-9H-purin-8-yl)-ethyl]-acetamide (275 mg, 0.68 mmol) and cesium carbonate (0.48 g, 1.36 mmol) in anhydrous DMF (10 mL) was stirred at RT for 2 h, then diluted with water and extracted five times with ethyl acetate. The combined organic extracts were dried ($Na_2SO_4$), filtered and concentrated in vacuo. The resulting residue was subjected to flash chromatography (SiO2) gradient 0-5% methanol in DCM) to give 3-Chloro-8-methyl-1-morpholin-4-yl-7,8-dihydro-2,4,4b,7,9-pentaaza-fluoren-6-one (93 mg, 42%). LCMS $R_T$=2.41 min, [M+H]$^+$=323/325

Step 8: A mixture of 3-chloro-8-methyl-1-morpholin-4-yl-7,8-dihydro-2,4,4b,7,9-pentaaza-fluoren-6-one (46 mg, 0.14 mmol), 2-aminopyrimidine-5-boronic acid pinacol ester (78 mg, 0.36 mmol), potassium fluoride (46 mg, 0.80 mmol) and Pd(PPh$_3$)$_4$ (18 mg, 0.016 mmol) in anhydrous 1,4-dioxane (5 mL) was heated at 100° C. for 16 h. After cooling to RT, the mixture was diluted with water and the precipitate formed was filtered off and washed with water. The solid was triturated with methanol, DCM and finally with acetonitrile to give 175 (8 mg, 15%). LCMS $R_T$=2.59 min, [M+H]$^+$=382. $^1$H NMR (DMSO-d6, 400 MHz): δ 9.11 (2H, s), 8.68 (1H, s), 7.05 (2H, s), 4.84 (1H, q, J=6.9 Hz), 4.76 (1H, d, J=17.2 Hz), 4 69 (1H, d, J=17.2 Hz), 4.25 (4H, broad), 3.75 (4H, t, J=4.5 Hz), 1.56 (3H, d, J=6.9 Hz).

Example 176

5-(6,7-dimethyl-4-morpholino-6,7,8,9-tetrahydropyrazino[2,1-e]purin-2-yl)pyrimidin-2-amine 176

Step 1: {1-[2-Chloro-6-morpholin-4-yl-9-(tetrahydropyran-2-yl)-9H-purin-8-yl]-ethyl}-carbamic acid tert-butyl ester

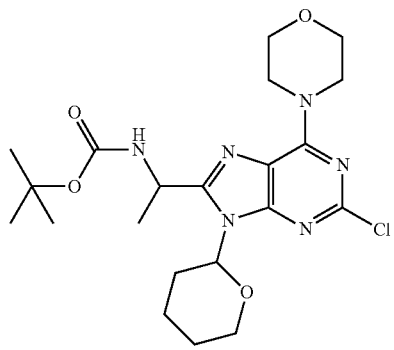

To solution of 1-[2-chloro-6-morpholin-4-yl-9-(tetrahydro-pyran-2-yl)-9H-purin-8-yl]-ethylamine (0.41 g, 1.12 mmol) in anhydrous DCM (10 mL) was added triethylamine (0.17 mL, 1.23 mmol) and di-tert-butyl dicarbonate (0.268 g, 1.23 mmol). The mixture was stirred at RT for 2 h, then washed with 10% aqueous citric acid. The aqueous phase was extracted three times with DCM, and the combined organic fractions were dried ($Na_2SO_4$), filtered and concentrated in vacuo. The resultant residue was triturated with diethyl ether, collected by filtration and dried (in vacuo, 50° C.) to give {1-[2-Chloro-6-morpholin-4-yl-9-(tetrahydro-pyran-2-yl)-9H-purin-8-yl]-ethyl}-carbamic acid tert-butyl ester (0.425 g, 81%, mixture of two pairs of diastereomers). LCMS $R_T$=4.06 and 4.13 min, [M+H]$^+$=467/469

Step 2: {1-[2-Chloro-6-morpholin-4-yl-9-(tetrahydropyran-2-yl)-9H-purin-8-yl]-ethyl}-methyl-carbamic acid tert-butyl ester

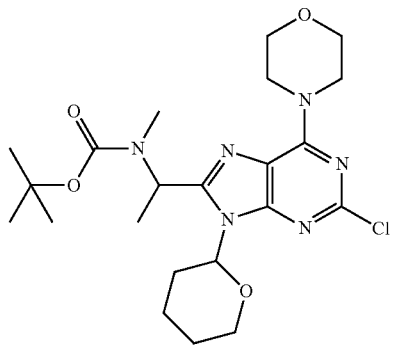

A solution of {1-[2-chloro-6-morpholin-4-yl-9-(tetrahydro-pyran-2-yl)-9H-purin-8-yl]-ethyl}-carbamic acid tert-butyl ester (218 mg, 0.47 mmol) in anhydrous THF (15 mL) was cooled to 0° C. Sodium hydride (60% suspension in oil, 22 mg, 0.56 mmol) was added and the mixture was stirred at 0° C. for 30 min. Iodomethane (10 vol. % solution in THF, 0.35 mL, 0.56 mmol) was added and the mixture was stirred for 16 h at RT. The reaction mixture was combined with another mixture, prepared in a similar manner from 210 mg of the carbamate starting-material, and diluted with water. After adjustment to pH7 by addition of 1M aqueous HCl and aqueous sodium bicarbonate, the mixture was extracted three times with ethyl acetate. The combined extracts were dried ($Na_2SO_4$), filtered and concentrated in vacuo, to give a 2:1 mixture of the title compound and carbamate starting-material (0.46 g). This mixture was dissolved in anhydrous THF (20 mL) and treated with sodium hydride (19 mg) and iodomethane (10 vol. % solution in THF, 0.29 mL) as before. After addition of more iodomethane (neat, 0.050 mL) and stirring for another 8 h, the reaction mixture was diluted with water, neutralized and extracted as before. The organic extracts were dried ($Na_2SO_4$), filtered and concentrated in vacuo. The resulting residue was subjected to flash chromatography (SiO2) gradient 0-20% ethyl acetate in cyclohexane) to give {1-[2-Chloro-6-morpholin-4-yl-9-(tetrahydro-pyran-2-yl)-9H-purin-8-yl]-ethyl}-methyl-carbamic acid tert-butyl ester (316 mg, 72%). LCMS $R_T$=4.48 min, [M+H]$^+$=481/483

Step 3: [1-(2-Chloro-6-morpholin-4-yl-9H-purin-8-yl)-ethyl]-methyl-amine

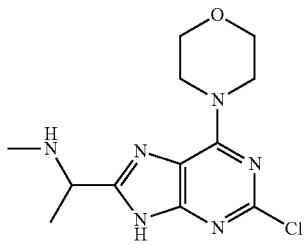

A mixture of {1-[2-chloro-6-morpholin-4-yl-9-(tetrahydro-pyran-2-yl)-9H-purin-8-yl]-ethyl}-methyl-carbamic acid tert-butyl ester (316 mg, 0.66 mmol) and p-toluenesulfonic acid monohydrate (30 mg) in methanol was stirred at room temperature for 3 h, then allowed to stand for 56 h. The reaction mixture was concentrated in vacuo to a small volume, then DCM (3 mL) and trifluoroacetic acid (3 mL) were added and the reaction mixture was stirred for 4.75 h at RT. Another portion of trifluoroacetic acid (3 mL) was added and stirring was continued for 2 h. The mixture was concentrated in vacuo and the resulting residue was triturated three times with diethyl ether. The resulting solid was partitioned between a 10% solution of methanol in DCM and aqueous sodium bicarbonate. The phases were separated, and the aqueous phase was extracted four times with a 10% solution of methanol in DCM. The combined organic fractions were dried ($Na_2SO_4$), filtered and concentrated in vacuo to give [1-(2-Chloro-6-morpholin-4-yl-9H-purin-8-yl)-ethyl]-methyl-amine (0.19 g, 97%). LCMS $R_T$=1.68 min, $[M+H]^+$=297

Step 4: 3-Chloro-7,8-dimethyl-1-morpholin-4-yl-5,6,7,8-tetrahydro-2,4,4b,7,9-pentaaza-fluorene

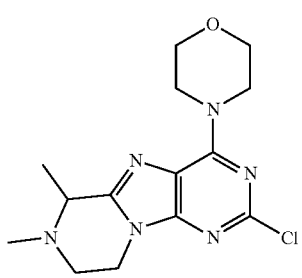

A mixture of: [1-(2-chloro-6-morpholin-4-yl-9H-purin-8-yl)-ethyl]-methyl-amine (95 mg, 0.32 mmol), cesium carbonate (652 mg, 2 mmol) and 1,2-dibromoethane (0.030 mL, 0.35 mmol) in DMF (5 mL) was stirred at RT for 4 h. Another portion of 1,2-dibromoethane (0.030 mL, 0.35 mmol) was added and stirring was continued for 20 h. The reaction mixture was diluted with water and extracted seven times with ether. The combined organic extracts were dried ($Na_2SO_4$), filtered and concentrated in vacuo. The resultant residue was subjected to flash chromatography (SiO2) gradient 0-4% methanol in DCM) to give 3-Chloro-7,8-dimethyl-1-morpholin-4-yl-5,6,7,8-tetrahydro-2,4,4b,7,9-pentaaza-fluorene (76 mg, 74%). LCMS $R_T$=1.82 min, $[M+H]^+$= 323/325

Step 5: A mixture of 3-chloro-7,8-dimethyl-1-morpholin-4-yl-5,6,7,8-tetrahydro-2,4,4b,7,9-pentaaza-fluorene (70 mg, 0.22 mmol), 2-aminopyrimidine-5-boronic acid pinacol ester (57 mg, 0.26 mmol) and cesium carbonate (216 mg, 0.66 mmol) in 1,4-dioxane (2.5 mL) and water (2.5 mL) was purged with argon. $Pd(PPh_3)_4$ (12 mg, 0.011 mmol) was added, the mixture was purged with argon again and then heated at 100° C. for 16 h. Further portions of the boronate ester (29 mg) and $Pd(PPh_3)_4$ (6 mg) were added and heating was continued for 5.5 h. The mixture was diluted with water and extracted five times with ethyl acetate. The combined organic extracts were dried ($Na_2SO_4$), filtered and concentrated in vacuo. The resultant residue was subjected to flash chromatography (SiO2) gradient 0-10% methanol in DCM) to give 176 (58 mg, 69%). LCMS $R_T$=2.11 min, $[M+H]^+$= 382. $^1$H NMR (DMSO-$d_6$, 400 MHz): δ 9.08 (2H, s), 7.01 (2H, s), 4.24 (4H, broad), 4.20 (1H, m), 4.00 (1H, m), 3.75 (4H, t, J=4.8 Hz), 3.55 (1H, q, J=6.6 Hz), 3.21 (1H, m), 2.78 (1H, m), 2.43 (3H, s), 1.50 (3H, d, J=6.6 Hz).

Example 177

5-(8,8-Dimethyl-1-morpholin-4-yl-5,6-dihydro-8H-7-oxa-2,4,4b-triaza-fluoren-3-yl)-pyrimidin-2-ylamine 177

Step 1: 7-Benzenesulfonyl-2,4-dichloro-7H-pyrrolo[2,3-d]pyrimidine

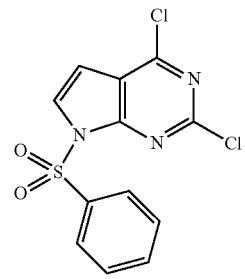

A solution of 2,4-dichloro-7H-pyrrolo[2,3-d]pyrimidine (1 g, 5.3 mmol) in anhydrous THF (5 mL) was added to a suspension of sodium hydride (234 mg, 5.83 mmol, 60% dispersion in mineral oil) in anhydrous THF (15 mL) at 0° C. The resulting mixture was stirred at 0° C. for 45 min, and benzenesulfonyl chloride (1.12 g, 6.36 mmol) was added dropwise. The reaction mixture was allowed to warm to ambient temperature and stirred at RT for 1 h. The reaction mixture was quenched with saturated aqueous ammonium chloride and extracted with ethyl acetate. The combined organic extracts were dried ($Na_2SO_4$) and concentrated in vacuo. The resulting residue was triturated with cyclohexane affording 7-Benzenesulfonyl-2,4-dichloro-7H-pyrrolo[2,3-d]pyrimidine as a yellow solid (1.52 g, 87%). $^1$H NMR (400 MHz, $CDCl_3$): δ 8.24 (2H, m), 7.76 (1H, d, J=4.0 Hz), 7.69 (1H, m), 7.58 (2H, m), 6.69 (1H, d, J=4.0 Hz).

Step 2: 2-(2,4-Dichloro-7H-pyrrolo[2,3-d]pyrimidin-6-yl)-propan-2-ol

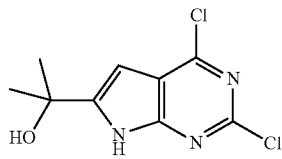

Lithium diisopropylamide (2 mL, 4.0 mmol, 2 M in THF) was added dropwise to a solution of 7-benzenesulfonyl-2,4-dichloro-7H-pyrrolo[2,3-d]pyrimidine (656 mg, 2.0 mmol) in anhydrous THF (15 mL) at −78° C. The resulting solution was stirred at −78° C. for 90 min, then acetone (0.4 mL, 5.5 mmol) was added and the reaction mixture was stirred at −78° C. for 30 min. The reaction mixture was quenched with saturated aqueous ammonium chloride and extracted with ethyl acetate. The combined organic extracts were dried (MgSO$_4$) and concentrated in vacuo affording 2-(7-benzenesulfonyl-2,4-dichloro-7H-pyrrolo[2,3-d]pyrimidin-6-yl)-propan-2-ol. To a solution of 2-(7-benzenesulfonyl-2,4-dichloro-7H-pyrrolo[2,3-d]pyrimidin-6-yl)-propan-2-ol (2 mmol) in a mixture of isopropyl alcohol (11 mL) and water (3 mL) was added sodium hydroxide (6 mL, 36 mmol, 6M aqueous solution). The resulting mixture was stirred at RT for 2 h, then concentrated in vacuo. The resulting residue was purified by column chromatography (SiO$_2$, gradient 0 to 40% ethyl acetate in cyclohexane) affording 2-(2,4-Dichloro-7H-pyrrolo[2,3-d]pyrimidin-6-yl)-propan-2-ol (304 mg, 64%). LCMS (method A): R$_T$=2.70 min, [M]$^-$=244/246.

Step 3: 3-Chloro-8,8-dimethyl-1-morpholin-4-yl-5,6-dihydro-8H-7-oxa-2,4,4b-triaza-fluorene

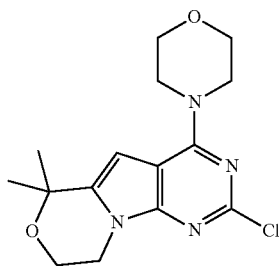

Cesium carbonate (1.2 g, 3.7 mmol) and 1,2-dibromoethane (316 µL, 3.7 mmol) were added to a solution of 2-(2,4-dichloro-7H-pyrrolo[2,3-d]pyrimidin-6-yl)-propan-2-ol (304 mg, 1.23 mmol) in DMF (4 mL) and the reaction mixture was heated at 100° C. for 45 min, then partitioned between water and ethyl acetate. The organic extract was separated and washed with brine, then dried (Na$_2$SO$_4$) and concentrated in vacuo affording 1,3-dichloro-8,8-dimethyl-5,6-dihydro-8H-7-oxa-2,4,4b-triaza-fluorene. A mixture of 1,3-dichloro-8,8-dimethyl-5,6-dihydro-8H-7-oxa-2,4,4b-triaza-fluorene (1.23 mmol), morpholine (236 µL, 2.69 mmol) and triethylamine (342 µL, 2.46 mmol) in IMS (3 mL) was heated at reflux for 3 h, then concentrated in vacuo. The resulting residue was purified by column chromatography (SiO$_2$, gradient 0 to 40% ethyl acetate in cyclohexane) affording 3-Chloro-8,8-dimethyl-1-morpholin-4-yl-5,6-dihydro-8H-7-oxa-2,4,4b-triaza-fluorene (159 mg, 40%). LCMS (method A): R$_T$=3.13 min, [M+H]$^+$=323.

Step 4: A mixture of 3-Chloro-8,8-dimethyl-1-morpholin-4-yl-5,6-dihydro-8H-7-oxa-2,4,4b-triaza-fluorene (75 mg, 0.23 mmol), 5-(4,4,5,5-tetramethyl-[1,3,2]dioxaborolan-2-yl)-pyrimidin-2-ylamine (115 mg, 0.52 mmol), bis(di-tert-butyl(4-dimethylaminophenyl)-phosphine)dichloropalladium(II) (25 mg, 0.035 mmol) and sodium carbonate (1 mL, 1.0 mmol, 1M aqueous solution) in acetonitrile (3 mL) was degassed and heated at 150° C. for 30 mins in a microwave reactor, then concentrated in vacuo. The resulting residue was purified by column chromatography (SiO$_2$, gradient 0 to 75% ethyl acetate in cyclohexane) followed by reverse phase HPLC (Phenomenex Gemini 5 µm C18, 0.1% HCO$_2$H in water on a gradient acetonitrile 5-98%) affording 177 as a off-white solid (13 mg, 15%). LCMS (method B): R$_T$=3.50 min, [M+H]$^+$=382. $^1$H NMR (400 MHz, CDCl$_3$): δ 9.27 (2H, s), 6.12 (1H, s), 5.27 (2H, broad s), 4.21 (2H, m), 4.14 (2H, m), 3.97 (4H, m), 3.88 (4H, m), 1.62 (6H, s)

Example 901 p110α (Alpha) PI3K Binding Assay

Binding Assays: Initial polarization experiments were performed on an Analyst HT® 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM tris pH 7.5, 50 mM NaCl, 4 mM MgCl$_2$, 0.05% Chaps, and 1 mM DTT) to 10 mM PIP$_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the protein concentration, and the EC$_{50}$ values were obtained by fitting the data to a 4-parameter equation using KaleidaGraph® software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110 alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume PROXIPLATES® (PerkinElmer, Wellesley, Mass.) Fluorescence polarization values were plotted as a function of the antagonist concentration, and the IC$_{50}$ values were obtained by fitting the data to a 4-parameter equation in Assay Explorer® software (MDL, San Ramon, Calif.).

Alternatively, inhibition of PI3K was determined in a radiometric assay using purified, recombinant enzyme and ATP at a concentration of 1 µM. The Formula I compound was serially diluted in 100% DMSO. The kinase reaction was incubated for 1 hr at room temperature, and the reaction was terminated by the addition of PBS. IC$_{50}$ values were subsequently determined using sigmoidal dose-response curve fit (variable slope).

Example 902

In Vitro Cell Proliferation Assay

Efficacy of Formula I compounds was measured by a cell proliferation assay employing the following protocol (Promega Corp. Technical Bulletin TB288; Mendoza et al (2002) Cancer Res. 62:5485-5488):

1. An aliquot of 100 μl of cell culture containing about $10^4$ cells (PC3, Detroit562, or MDAMB361.1) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo® Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 hr before reading at 544 nm excitation, 590 nm emission. $EC_{50}$ values were calculated using a sigmoidal dose response curve fit. The term $EC_{50}$ refers to the half maximal effective concentration and is the concentration at which a drug induces a response halfway between the baseline and maximum after some specified exposure time. It is commonly used as a measure of drug potency.

The anti-proliferative effects of Formula I exemplary compounds were measured by the CellTiter-Glo® Assay against various tumor cell lines, including the following:

| Compound No. | Cell line: MDA-MB-361.1<br>Tissue type: breast<br>Mutation Status: PI3K<br>EC50 (μmole) | Cell line: PC3<br>Tissue type: prostate<br>Mutation Status: PTEN<br>EC50 (μmole) |
|---|---|---|
| 101 | 0.315 | 0.208 |
| 102 | 0.081 | 2 |
| 103 | 0.269 | 0.44 |
| 115 | 0.958 | 1.8 |
| 121 | 0.36 | — |
| 122 | 3.2 | 2 |
| 138 | 10+ | 10+ |
| 139 | 0.424 | 0.697 |
| 148 | 10+ | 10+ |
| 163 | 10+ | 10+ |
| 165 | 1.2 | 1.3 |
| 168 | 0.237 | 0.215 |
| 169 | 4.4 | 6.9 |
| 170 | 0.92 | 1.1 |
| 171 | 3.1 | 3.8 |
| 172 | 1.5 | 1.4 |
| 174 | 3.4 | 3.6 |
| 176 | 0.889 | 1.9 |
| 177 | 0.094 | 0.185 |

Example 903

Caco-2 Permeability

Caco-2 cells are seeded onto Millipore Multiscreen® plates at $1 \times 10^5$ cells/cm$^2$, and cultured for 20 days. Assessment of compound permeability is subsequently conducted. The compounds are applied to the apical surface (A) of cell monolayers and compound permeation into the basolateral (B) compartment is measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0 \times 10^6$ cm/s) or high ($P_{app}>/=1.0 \times 10^6$ cm/s) absorption potential based on comparison with control compounds with established human absorption.

For assessment of a compound's ability to undergo active efflux, the ratio of basolateral (B) to apical (A) transport compared with A to B was determined. Values of B-A/A-B>/=1.0 indicate the occurrence of active cellular efflux.

Example 904

Hepatocyte Clearance

Suspensions of cryopreserved human hepatocytes are used. Incubations are performed at compound concentration of 1 mM or 3 μM at a cell density of $0.5 \times 10^6$ viable cells/mL. The final DMSO concentration in the incubation is about 0.25%. Control incubations are also performed in the absence of cells to reveal any non-enzymatic degradation. Duplicate samples (50 μL) are removed from the incubation mixture at 0, 5, 10, 20, 40 and 60 minutes (control sample at 60 minutes only) and added to methanol containing internal standard (100 μL)—to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance ($CL_{int}$) is calculated as follows: $CL_{int}$ (μl/min/million cells)=V×k, where k is the elimination rate constant, obtained from the gradient of ln concentration plotted against time; V is a volume term derived from the incubation volume and is expressed as uL $10^6$ cells$^{-1}$.

Example 905

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar™ in fluorescence mode.

Example 906

Cytochrome P450 Induction

Freshly isolated human hepatocytes from a single donor may be cultured for about 48 hr prior to addition of Formula I compound at three concentrations and incubated for 72 hr. Probe substrates for CYP3A4 and CYP1A2 are added for 30 minutes and 1 hr before the end of the incubation. At 72 hr, cells and media are removed and the extent of metabolism of each probe substrate quantified by LC-MS/MS. The experiment is controlled by using inducers of the individual P450s incubated at one concentration in triplicate.

Example 907

Plasma Protein Binding

Solutions of Formula I compound (5 um, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 hr in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compound is calculated.

Example 908 hERG Channel Blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 μL of pre-incubation buffer (containing low [$K^+$]) at room temperature. Following the final aspiration, 50 μL of working stock (2×) compound is added to each well and incubated at room temperature for 10 minutes. Stimulation buffer 50 μL (containing high [K+]) is then added to each well giving the final test compound concentrations. Cell plates are then incubated at room temperature for a further 10 minutes. Supernatant 80 μL from each well is then transferred to equivalent wells of a 96-well plate and analyzed via atomic emission spectroscopy. The compound is screened as 10 pt duplicate $IC_{50}$ curves, n=2, from a top concentration of 100 μM.

Example 909

In Vivo Tumor Xenograft

NCR nude mice (Taconic Farms, IN) were inoculated subcutaneously in the right lateral thorax with 5 million U-87 MG Merchant (an in-house variant derived from U-87 MG cells from ATCC, Manassas, Va.) cells in HBSS/Matrigel (1:1, v/v). Mice bearing tumor xenografts were dosed daily orally by gavage for <28 days with drug or vehicle after being separated into different dose groups of similarly sized tumors. Tumor sizes were recorded at least twice weekly over the course of the study. Mouse body weights were also recorded at least twice weekly, and the mice were observed daily. Tumor volume was measured in two perpendicular dimensions (length and width) using Ultra Cal-IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using GraphPad Prism™, Version 5.0c (GraphPad Software, Inc.; La Jolla, Calif.). The tumor volume was calculated with formula:Tumor size ($mm^3$)= (longer measurement×shorter measurement$^2$)×0.5

Animal body weights were measured using an Adventurer Pro™ AV812 scale (Ohaus Corporation; Pine Brook, N.J.). Graphs were generated using GraphPad Prism™, Version 5.0c. Percent weight change was calculated using formula: individual percent weight change=((new weight/initial weight)−1)×100.

Mice whose tumor volume exceeded 2000 $mm^3$ or whose body weight loss exceeded 20% of their starting weight were euthanized according to regulatory guidance.

The percent tumor growth inhibition (% TGI) at the end of study (EOS) was calculated using formula:
% TGI=(1−[(AUC/Day)$_{Treatment}$÷(AUC/Day)$_{Control}$])× 100, where AUC/Day is the area under the fitted tumor growth curve on the natural scale divided by the number of study days. Log 2(tumor volume) growth traces were fitted to each dose group with restricted cubic splines for the fixed time and dose effect in each group. Fitting was done via a linear mixed effects model, using the R package 'nlme', version 3.1-97 (11) in R version 2.12.0 (R Development Core Team 2008; R Foundation for Statistical Computing; Vienna, Austria).

A partial response (PR) was defined as a >50% reduction in starting tumor volume that never became a complete response (CR) at any day of the study. CR was defined as a 100% reduction in starting tumor volume at any day of the study. Study tumor incidence (STI) reflected the number of animals in a group with a measurable tumor for their last tumor volume measurement.

Linear mixed effect analysis was also employed to model the percent change in body weight over time and in response to dose.

Example 910

Phospho AKT Induction Assay

In a 6-well tissue culture plate cells were seeded at 5×10$^5$ cells per well overnight. Cells were treated with an EC$_{80}$ of the Formula I compound. Following treatment, cells were washed once with cold PBS and lysed in 1× Cell Extraction Buffer from Biosource (Carlsbad, Calif.) supplemented with protease inhibitors (Roche, Mannheim, Germany), 1 mM PMSF, and Phosphatase Inhibitor Cocktails 1 and 2 from Sigma (St. Louis, Mo.). Determination of protein concentration was performed using the Pierce BCA Protein Assay Kit (Rockford, Ill.). Levels of pAkt (Ser$^{473}$) and total Akt were assessed using bead kits from Biosource (Carlsbad, Calif.) and the Luminex™ Bio-Plex system (Bio-Rad, Hercules, Calif.).

Example 911

Blood-Brain Barrier Activity/Penetrant Assay
MDCKI-MDR1 and MDCKII-Bcrp1 Assays

Madin-Darby canine kidney (MDCK) cells heterologously expressing either human Pgp or mouse Bcrp1 were used to determine whether the compounds were substrate of these transporters, and thus assess the potential for blood-brain barrier permeation. MDR1-MDCKI cells were licensed from the NCI (National Cancer Institute, Bethesda, Md.) while Bcrp1-MDCKII cells were obtained from the Netherlands Cancer Institutes (Amsterdam, The Netherlands). Cells were seeded on 24-well Millipore filter plates 4 days prior to use (polyester membrane, 1 μM pore size; Millipore; Billerica, Mass.) at a seeding density of 1.3×10$^5$ cells/mL. Compounds were tested at 5 μM in the apical to basolateral (A-B) and basolateral to apical (B-A) directions. The compounds were dissolved in transport buffer consisting of Hank's balanced salt solution (HBSS) with 10 mM HEPES (Invitrogen Corporation, Grand Island, N.Y.). Lucifer Yellow (Sigma-Aldrich, St. Louis, Mo.) was used as the paracellular marker. The apparent permeability ($P_{app}$) in the A-B and B-A directions was calculated after a 2-hour incubation using the following equation:

$$P_{app} = (dQ/dt) \times 1/C_0 \times 1/A$$

where dQ/dt is the rate of compound appearance in the receiver compartment, Co is the concentration in the donor compartment and A is the surface area of the insert. The Efflux Ratio, defined as $P_{app(B-A)}/P_{app\ A-B}$, was used to assess the extent of active efflux undergone by the compounds with the transporter tested (P-glycoprotein or bcrp1). The compounds were analyzed by LC-MS/MS Example 912

Determination of Compound Concentration in the Brain

Brains were collected at 1 and 6 hours post-dose from 3 different animals at each time point, rinsed with ice-cold saline, weighed and store at −80° C. until analysis. For compound quantitation, mouse brains were homogenized in 3 volumes of water. The homogenates were extracted by protein precipitation with acetonitrile containing the internal standard. LC-MS/MS analysis was conducted. Brain homogenates concentrations were converted to brain concentrations for the calculations of brain-to-plasma ratios.

Example 913

Measurement of the Modulation of the PI3K Pathway in the Brain

For analysis of PI3K pathway modulation, cell extraction buffer (Invitrogen, Camarillo, Calif.) containing 10 mM Tris pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, and 0.5% deoxycholate was supplemented with phosphatase, protease inhibitors (Sigma, St. Louis, Mo.) and 1 mM PMSF and added to frozen brain biopsies. Brains collected at 1 and 6 hrs post-dose were homogenized with a small pestle (Konte Glass Company, Vineland, N.J.), sonicated briefly on ice, and centrifuged at 20,000 g for 20 minutes at 4° C. Protein concentration was determined using BCA protein assay (Pierce, Rockford, Ill.). Proteins were separated by electrophoresis and transferred to NuPage nitrocellulose membranes (Invitrogen, Camarillo, Calif.). Licor Odyssey™ Infrared detection system (Licor, Lincoln, Nebr.) was used to assess and quantify protein expression. PI3K pathway markers were evaluated by immunoblotting using antibodies against $pAkt^{ser473}$ and total Akt (Invitrogen, Camarillo, Calif. and Cell Signaling, Danvers, Mass.).

Example 914

Brain Tumor In Vivo Efficacy Assay

CD-1 Nude mice (Charles River Laboratories, Hollister, Calif.) were inoculated intracranially under stereotactic surgery with GS-2 (human glioblastoma muliforme) cells engineered in-house to express luciferase in HBSS. Mice with confirmed brain xenografts by magnetic resonance imaging (MRI) at four weeks post cell inoculation were dosed once daily orally by gavage for 28 days with drug or vehicle after being separated into groups of similarly sized tumors. MRI (4.7T, Varian, Inc., Palo Alto, Calif.) was repeated at the end of the 28-day dosing period to assess response to treatment.

Mouse body weights were recorded at least twice weekly, and the mice were observed daily. Animal body weights were measured using an Adventurer Pro™ AV812 scale (Ohaus Corporation; Pine Brook, N.J.). Graphs were generated using GraphPad Prism, Version 5.0c. Percent weight change was calculated using formula: individual percent weight change=((new weight/initial weight)−1)×100. Mice whose body weight loss exceeded 20% of their starting weight were euthanized according to regulatory guidance.

The tumor volume change was modeled as linear over the two times at which each animal was imaged. A linear mixed effects model was fitted to these data using the R package 'nlme', version 3.1-97 in R version 2.12.0 (R Development Core Team 2010; R Foundation for Statistical Computing; Vienna, Austria). A mixed effect model takes into account repeated measures on individual mice over time and handles the intra-mouse correlation appropriately. Linear mixed effect analysis was also employed to model the percent change in body weight over time.

Plasma and brain samples were collected at 2 and 8 hours post administration of the final treatment for pharmacokinetic (PK), pharmacodynamic (PD), and/or immunohistochemical (IHC) analysis.

Example 915

In Vivo Tumor Xenograft PK/PD Study

NCR nude mice (Taconic Farms, IN) were inoculated subcutaneously in the right lateral thorax with 5 million U-87 MG Merchant (an in-house variant derived from U-87 MG cells from ATCC, Manassas, Va.) cells in HBSS/Matrigel™, BD Biosciences (1:1, v/v). Mice bearing tumor xenografts >600 $mm^3$ were dosed once with drug or vehicle after being separated into groups of similarly sized tumors. Plasma, subcutaneous tumor xenograft, skeletal muscle, and brain samples were collected at 1, 4, 12, and 24 hours post treatment administration for PK, PD, and/or IHC analysis.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of treating cancer characterized by over expression of PI3 kinase in a patient, the method comprising administering to said patient a therapeutically effective amount of a compound of Formula I:

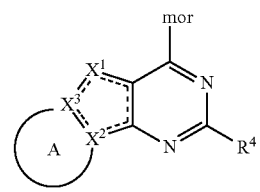

and stereoisomers, geometric isomers, tautomers, and pharmaceutically acceptable salts thereof, wherein:
the dashed lines indicate an optional double bond, and at least one dashed line is a double bond;
$X^1$ is S, O, N, $NR^a$, $CR^1$, $C(R^1)_2$, or —$C(R^1)_2O$—;
$X^2$ is C, $CR^2$ or N;
$X^3$ is C, $CR^3$ or N;

A is a 5, 6, or 7-membered carbocyclyl or heterocyclyl ring fused to $X^2$ and $X^3$, optionally substituted with one or more $R^5$ groups;

$R^a$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^1$, $R^2$, and $R^3$ are independently selected from H, F, Cl, Br, I, —$CH_3$, —$CH_2CH_3$, —$C(CH_3)_3$, —$CH_2OH$, —$CH_2CH_2OH$, —$C(CH_3)_2OH$, —$CH_2OCH_3$, —CN, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

$R^4$ is selected from $C_6$-$C_{20}$ aryl, $C_2$-$C_{20}$ heterocyclyl and $C_1$-$C_{20}$ heteroaryl, each of which are optionally substituted with one or more $R^6$ groups independently selected from F, Cl, Br, I, —$CH_3$, —$CH_2CH_3$, —$CH(CH_3)_2$, —$CH_2CH(CH_3)_2$, —$CH_2CN$, —CN, —$CF_3$, —$CH_2OH$, —$CO_2H$, —$CONH_2$, —$CONH(CH_3)$, —$CON(CH_3)_2$, —$NO_2$, —$NH_2$, —$NHCH_3$, —$NHCOCH_3$, —OH, —$OCH_3$, —$OCH_2CH_3$, —$OCH(CH_3)_2$, —SH, —NHC(=O)$NHCH_3$, —NHC(=O)$NHCH_2CH_3$, —NHC(=O)$NHCH(CH_3)_2$, —$NHS(O)_2CH_3$, —$N(CH_3)C(=O)OC(CH_3)_3$, —$S(O)_2CH_3$, benzyl, benzyloxy, morpholinyl, morpholinomethyl, and 4-methylpiperazin-1-yl; and $R^5$ is independently selected from $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene) -C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl); or two geminal $R^5$ groups form a 3, 4, 5, or 6-membered carbocyclyl or heterocyclyl ring, where alkyl, alkenyl, alkynyl, alkylene, carbocyclyl, heterocyclyl, aryl, and heteroaryl are optionally substituted with one or more groups independently selected from F, Cl, Br, I, —$CH_3$—$CH_2CH_3$, —$C(CH_3)_3$, —$CH_2OH$, —$CH_2CH_2OH$, —$C(CH_3)_2OH$, —$CH_2OCH_3$, —CN, —$CH_2F$, —$CHF_2$, —$CF_3$, —$CO_2H$, —$COCH_3$, —$COC(CH_3)_3$, —$CO_2CH_3$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$S(O)_2CH_3$, cyclopropyl, cyclobutyl, oxetanyl, morpholino, and 1,1-dioxo-thiopyran-4-yl;

mor is selected from:

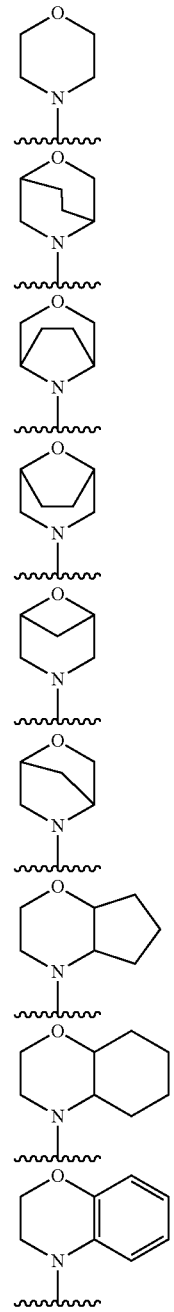

wherein mor is optionally substituted with one or more $R^7$ groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2OH$, —$CH(CH_3)OH$, —$CH(CH_2CH_3)OH$, —$CH_2CH(OH)CH_3$, —$C(CH_3)_2OH$, —$C(CH_3)_2OCH_3$, —$CH(CH_3)F$, —$C(CH_3)F_2$, —$CH(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —N(CH₃)₂, —NHCH₂CH₃, —NHCH(CH₃)₂, —NHCH₂CH₂OH, —NHCH₂CH₂OCH₃, NHCOCH₃, —NHCOCH₂CH₃, —NHCOCH₂OH, —NHS(O)₂CH₃, —N(CH₃)S(O)₂CH₃, =O, —OH, —OCH₃, —OCH₂CH₃, —OCH(CH₃)₂, —SH, —NHC(=O)NHCH₃, —NHC(=O)NHCH₂CH₃, —S(O)CH₃, —S(O)CH₂CH₃, —S(O)₂CH₃, —S(O)₂NH₂, —S(O)₂NHCH₃, —S(O)₂N(CH₃)₂, and —CH₂S(O)₂CH₃; and wherein the cancer is characterized by over expression of PI3 kinase and is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, renal, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's and leukemia.

2. The method of claim 1 wherein the cancer is a brain cancer.

3. The method of claim 1 further comprising administering to the patient an additional therapeutic agent selected from a chemotherapeutic agent, an anti-angiogenesis therapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

4. The method of claim 3 wherein the additional therapeutic agent is bevacizumab.

5. The method of claim 1 wherein the PI3 kinase is p110 alpha.

6. The method of claim 1 wherein:
the bond between X¹ and X³ is a double bond and the bond between X² and X³ is a single bond;
X¹ is selected from N and CR¹;
X² is N;
X³ is C;
A is a 5- or 6-membered carbocyclyl or heterocyclyl optionally substituted with one or more R⁵ groups;
R¹ is H;
R⁴ is selected from C₆-C₂₀ aryl and C₅-C₆ heteroaryl each of which are optionally substituted with one or more R⁶ groups independently selected from —CH₃, —CH₂CH₃, —CH(CH₃)₂, —CH₂CH(CH₃)₂, —CF₃, —NH₂, —NHC(=O)NHCH₃, —NHC(=O)NHCH₂CH₃ and —NHC(=O)NHCH(CH₃)₂;
R⁵ is C₁-C₁₂ alkyl or two germinal R⁵ groups forma a 3-, 4-, 5- or 6-membered carbocyclyl or heterocyclyl ring optionally substituted with one or more groups selected from F, Cl, Br, I and —OH; and
mor is:

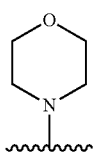

wherein mor is optionally substituted with one or more R⁷ groups independently selected from —CH₃, —CH₂CH₃, —CH₂CH₂CH₃, —CH(CH₃)₂ and —C(CH₃)₃.

7. The method of claim 1 wherein the compound of Formula I is selected from:

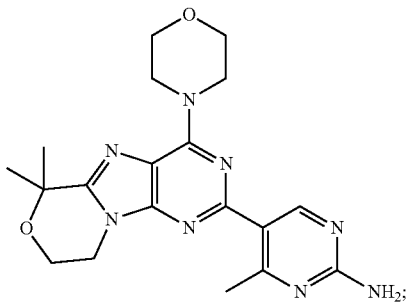

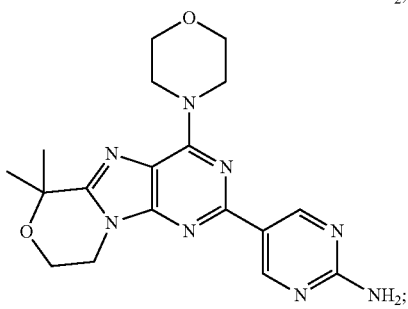

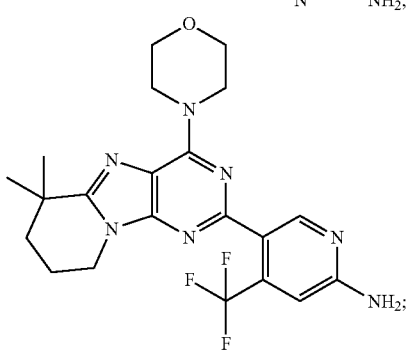

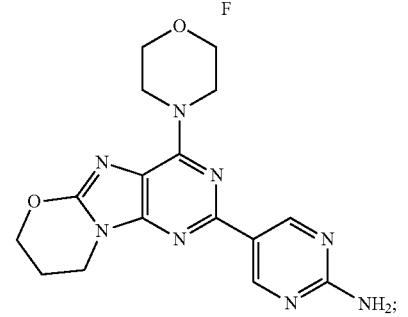

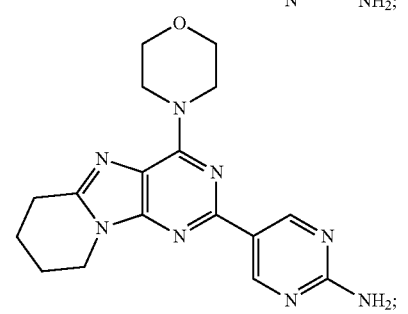

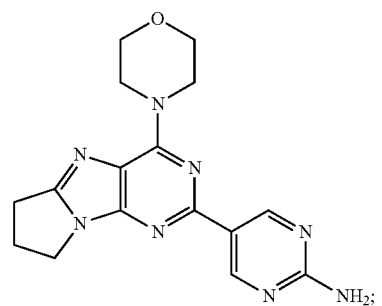
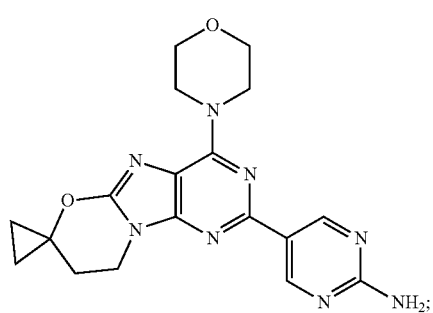
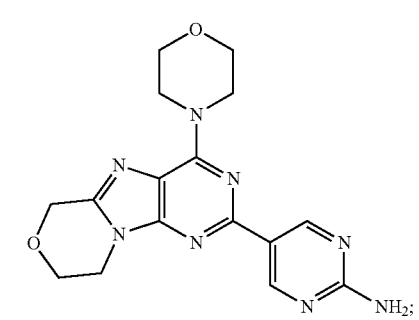
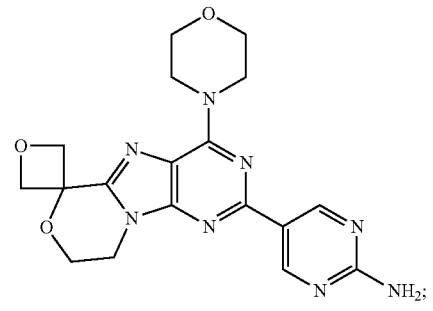
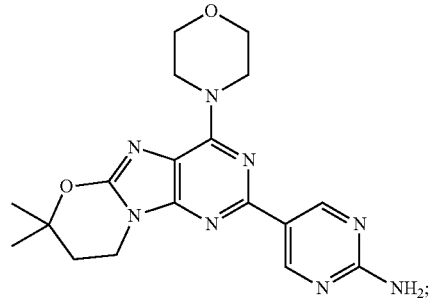
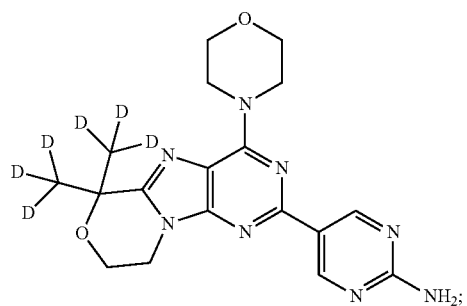
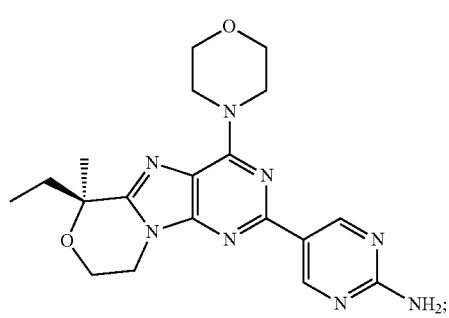
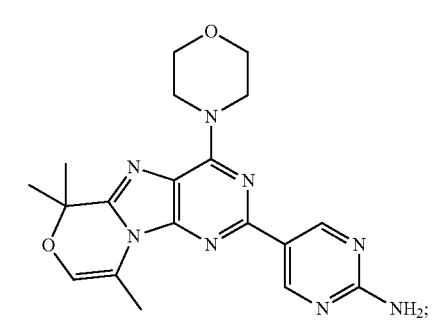
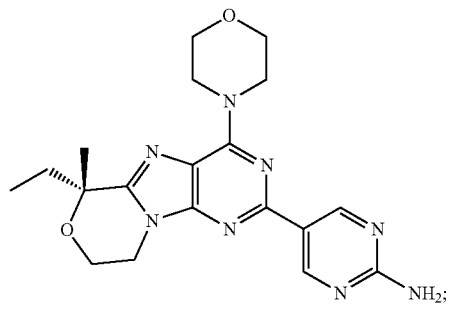
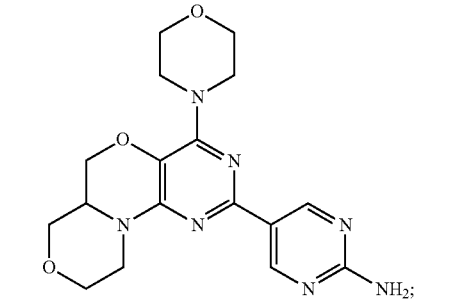

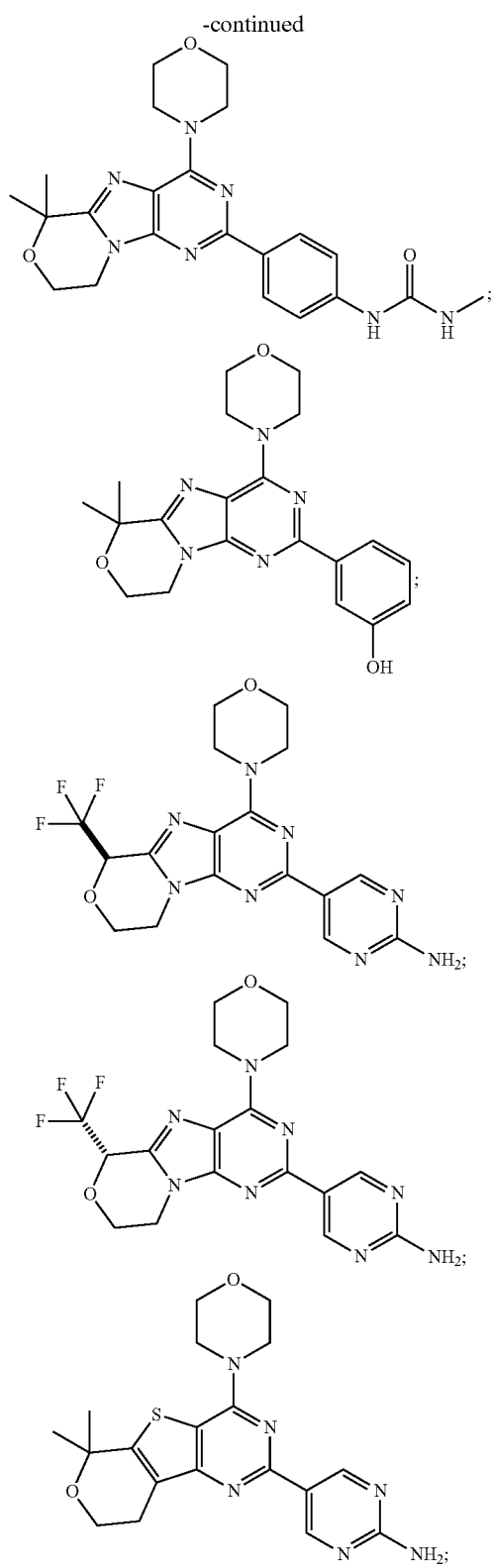
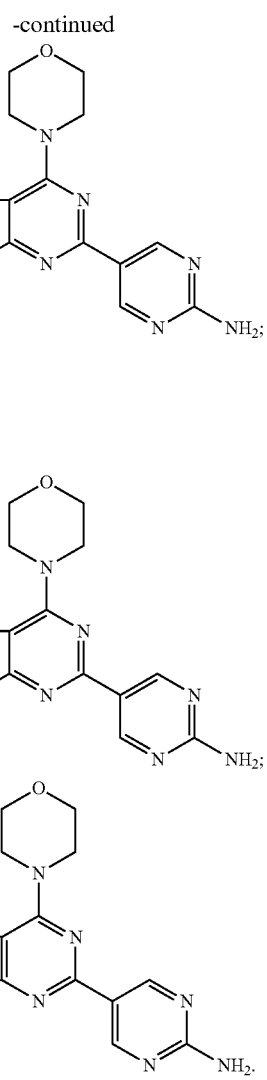
8. The method of claim 7 wherein the compound of Formula I is:
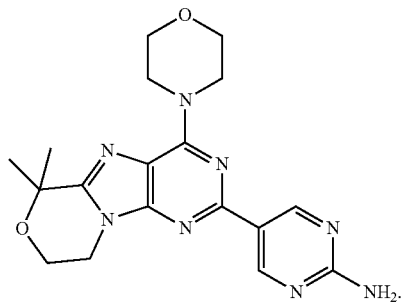
* * * * *